United States Patent
Rahdert et al.

(10) Patent No.: US 12,239,533 B2
(45) Date of Patent: Mar. 4, 2025

(54) DEVICE, METHOD AND SYSTEM FOR RESHAPING A HEART VALVE ANNULUS

(71) Applicant: MVRX, INC., San Mateo, CA (US)

(72) Inventors: David A. Rahdert, San Mateo, CA (US); Richard T. Childs, San Mateo, CA (US); David R. Tholfsen, San Leandro, CA (US); Patrick P. Wu, San Carlos, CA (US)

(73) Assignee: MVRx, Inc., San Mateo, CA (US)

( * ) Notice: Subject to any disclaimer, the term of this patent is extended or adjusted under 35 U.S.C. 154(b) by 382 days.

(21) Appl. No.: 17/544,696

(22) Filed: Dec. 7, 2021

(65) Prior Publication Data
US 2022/0175530 A1    Jun. 9, 2022

Related U.S. Application Data

(60) Provisional application No. 63/122,415, filed on Dec. 7, 2020.

(51) Int. Cl.
*A61B 17/34* (2006.01)
*A61F 2/24* (2006.01)
(Continued)

(52) U.S. Cl.
CPC ......... *A61F 2/2466* (2013.01); *A61M 25/003* (2013.01); *A61M 25/007* (2013.01);
(Continued)

(58) Field of Classification Search
CPC .................. A61F 2/2466; A61F 2/2487; A61F 2002/30079; A61F 2210/009;
(Continued)

(56) References Cited

U.S. PATENT DOCUMENTS 4,838,879 A  *  6/1989  Tanabe ............... A61B 6/12
                                                                604/529
5,570,671 A      11/1996  Hickey
(Continued)

FOREIGN PATENT DOCUMENTS

EP        2 929 859 A1    10/2015
WO    WO 2014/191924 A1   12/2014
(Continued)

OTHER PUBLICATIONS

PCT International Search Report and Written Opinion in International Application No. PCT/US2021/062182, dated Apr. 1, 2022, 10 pages.
(Continued)

*Primary Examiner* — Kelly J Bekker
*Assistant Examiner* — Lindsey R. Rivers
(74) *Attorney, Agent, or Firm* — DLA Piper LLP (US)

(57) ABSTRACT

Delivery systems, methods and associated devices to facilitate delivery and deployment of a heart implant. Such delivery systems and methods of delivery include use of a pair of magnetic catheters, including an anchor delivery catheter carrying an anchor, which can be stacked with or can be axially offset from the magnetic head. Such systems further include use of a puncturing guidewire advanceable through the magnetic head of the anchor delivery catheter to establish access to a chamber of a heart and which is attached to a bridging element such that continued advancement of the guidewire draws a bridging element attached to the first anchor across the chamber of the heart while the bridging element remains covered by the magnetically coupled catheters. Methods and devices herein also allow for cutting and removal of a bridge element of a deployed heart implant.

34 Claims, 56 Drawing Sheets

(51) Int. Cl.
*A61M 25/00* (2006.01)
*A61M 25/01* (2006.01)
*A61M 25/06* (2006.01)

(52) U.S. Cl.
CPC .... *A61M 25/0082* (2013.01); *A61M 25/0108* (2013.01); *A61M 25/0127* (2013.01); *A61M 25/0136* (2013.01); *A61M 25/0662* (2013.01); *A61B 17/34* (2013.01); *A61B 17/3468* (2013.01); *A61F 2220/0008* (2013.01); *A61M 2025/0004* (2013.01); *A61M 2025/0095* (2013.01)

(58) Field of Classification Search
CPC ............... A61B 17/34; A61B 17/3468; A61B 2017/00876; A61M 25/007; A61M 25/0108; A61M 25/0127; A61M 2025/0095; A61M 2025/09175
See application file for complete search history.

(56) References Cited

U.S. PATENT DOCUMENTS

| | | | |
|---|---|---|---|
| 5,830,224 | A | 11/1998 | Cohn et al. |
| 10,799,354 | B2 | 10/2020 | Machold et al. |
| 10,828,042 | B2 | 11/2020 | Goldfarb et al. |
| 2002/0183838 | A1 | 12/2002 | Liddicoat et al. |
| 2006/0106279 | A1 | 5/2006 | Machold et al. |
| 2006/0241656 | A1 | 10/2006 | Starksen et al. |
| 2007/0080188 | A1 | 4/2007 | Spence et al. |
| 2008/0091059 | A1 | 4/2008 | Machold et al. |
| 2008/0091264 | A1* | 4/2008 | Machold ............... A61M 25/09 623/2.1 |
| 2009/0036872 | A1 | 2/2009 | Fitzgerald et al. |
| 2010/0298930 | A1 | 11/2010 | Orlov |
| 2014/0276335 | A1 | 9/2014 | Pate |
| 2016/0067043 | A1 | 3/2016 | Machold et al. |
| 2018/0333162 | A1* | 11/2018 | Saab ................. A61M 25/0108 |
| 2019/0038410 | A1* | 2/2019 | Machold ............... A61F 2/2451 |
| 2020/0222168 | A1 | 7/2020 | Laeseke et al. |
| 2020/0238058 | A1 | 7/2020 | Narayan et al. |

FOREIGN PATENT DOCUMENTS

| | | |
|---|---|---|
| WO | WO 2018/189593 A2 | 10/2018 |
| WO | WO 2019/028471 | 2/2019 |

OTHER PUBLICATIONS

PCT International Search Report and Written Opinion in International Application No. PCT/US2021/062173, dated Apr. 1, 2022, 11 pages.

PCT International Search Report and Written Opinion in International Application No. PCT/US2021/062198, dated Mar. 9, 2022, 10 pages.

EP Extended Search Report in European Application No. 21904245.4, dated Oct. 4, 2024, 8 pages.

EP Supplementary Search Report in European Application No. 21904241.3, dated Sep. 25, 2024, 15 pages.

EP Supplementary Search Report in European Application No. 21904235.5, dated Sep. 26, 2024, 15 pages.

* cited by examiner

2.

CROSSING WIRE PUNCTUER TISSUE, ADVANCES INTO CHANNEL OF GCV MAGNET CATHETER

3.

PUSHER TUBE PUSHER T-BAR TBAR CROSSET TISSUE, ADVANCER INTO GCV, CHANNEL OF GCV-ME

DEVICE, METHOD AND SYSTEM FOR RESHAPING A HEART VALVE ANNULUS

CROSS-REFERENCE TO RELATED APPLICATION(S)

This application claims benefit of priority under 35 U.S.C. § 119 (e) of U.S. Provisional Patent Application Ser. No. 63/122,415, filed Dec. 7, 2020. The disclosure of the prior application is considered part of and is incorporated by reference in the disclosure of this application.

BACKGROUND OF THE INVENTION

Field of the Invention

The present invention relates generally to medical device and procedures, and more particularly to a system, device and method for delivering a heart implant to treat a cardiac disorder, such as mitral valve regurgitation.

Background Information

Treatments for mitral valve regurgitation are widely varied, encompassing both replacement valves, as well as a number of approaches that facilitate repair and reshaping of the valve by use of an implant. While many such approaches rely on intravascular delivery of an implant, these often utilize a system of multiple catheters that are repeatedly exchanged, which is an often complex and time-consuming process. To appreciate the difficulties and challenges associated with delivery and deployment of an implant within the human heart, it is useful to understand various aspects of the anatomy of the heart as well as conventional methods of deploying an implant for treatment of mitral valve regurgitation.

The Anatomy of a Healthy Heart

As can be seen in FIG. 2A, the human heart is a double-sided (left and right side), self-adjusting pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side: the right and left atria, and the right and left ventricles. The atriums are the blood-receiving chambers, which pump blood into the ventricles. The ventricles are the blood-discharging chambers. A wall composed of fibrous and muscular parts, called the interatrial septum separates the right and left atriums (see FIGS. 2B-2D). An anatomic landmark on the interatrial septum is an oval, thumbprint sized depression called the oval fossa, or fossa ovalis (FO), shown in FIG. 2C, which is a remnant of the oval foramen and its valve in the fetus and thus is free of any vital structures such as valve structure, blood vessels and conduction pathways. The synchronous pumping actions of the left and right sides of the heart constitute the cardiac cycle. The cycle begins with a period of ventricular relaxation, called ventricular diastole. The cycle ends with a period of ventricular contraction, called ventricular systole. The heart has four valves (see FIGS. 2B and 2C) that ensure that blood does not flow in the wrong direction during the cardiac cycle: that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (ventricular filling), the aortic and pulmonary valves are closed to prevent back flow from the arteries into the ventricles.

Shortly thereafter, the tricuspid and mitral valves open, as shown in FIG. 2B, to allow flow from the atriums into the corresponding ventricles. Shortly after ventricular systole (ventricular emptying) begins, the tricuspid and mitral valves close, as shown in FIG. 2C, to prevent back flow from the ventricles into the corresponding atriums, and the aortic and pulmonary valves open to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

As FIGS. 2B-2C show; the anterior (A) portion of the mitral valve annulus is intimate with the non-coronary leaflet of the aortic valve. Notably, the mitral valve annulus is near other critical heart structures, such as the circumflex branch of the left coronary artery (which supplies the left atrium, a variable amount of the left ventricle, and in many people the SA node) and the AV node (which, with the SA node, coordinates the cardiac cycle). In the vicinity of the posterior (P) mitral valve annulus is the coronary sinus and its tributaries. These vessels drain the areas of the heart supplied by the left coronary artery. The coronary sinus and its tributaries receive approximately 85% of coronary venous blood. The coronary sinus empties into the posterior of the right atrium, anterior and inferior to the fossa ovalis, as can be seen FIG. 2C. A tributary of the coronary sinus is called the great cardiac vein, which courses parallel to the majority of the posterior mitral valve annulus, and is superior to the posterior mitral valve annulus by an average distance of about 9.64+/−3.15 millimeters.

Characteristics and Causes of Mitral Valve Dysfunction

When the left ventricle contracts after filling with blood from the left atrium, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaptation occurs near the plane of the mitral annulus. The blood continues to be pressurized in the left ventricle until it is ejected into the aorta. Contraction of the papillary muscles is simultaneous with the contraction of the ventricle and serves to keep healthy valve leaflets tightly shut at peak contraction pressures exerted by the ventricle.

In a healthy heart (shown in FIGS. 2E-2F), the dimensions of the mitral valve annulus create an anatomic shape and tension such that the leaflets coapt, forming a tight junction, at peak contraction pressures. Where the leaflets coapt at the opposing medial (CM) and lateral (CL) sides of the annulus are called the leaflet commissures. Valve malfunction can result from the chordae tendineae (the chords) becoming stretched, and in some cases tearing. When a chord tears, the result is a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease. Regardless of the cause, mitral valve dysfunction can occur when the leaflets do not coapt at peak contraction pressures, as shown in FIG. 2G. In such cases, the coaptation line of the two leaflets is not tight at ventricular systole. As a result, an undesired back flow of blood from the left ventricle into the left atrium can occur, commonly known as mitral regurgitation. This has two important consequences. First, blood flowing back into the atrium may cause high atrial pressure and reduce the flow of blood into the left atrium from the lungs. As blood backs up into the pulmonary system, fluid leaks into the lungs and causes pulmonary edema. Second, the blood volume going to the atrium reduces volume of blood going forward into the aorta causing low cardiac output. Excess blood in the atrium over-fills the ventricle during each cardiac cycle and causes volume overload in the left ventricle.

Mitral regurgitation is categorized into two main types: i) organic or structural; and ii) functional. Organic mitral regurgitation results from a structurally abnormal valve component that causes a valve leaflet to leak during systole. Functional mitral regurgitation results from annulus dilation due to primary congestive heart failure, which is itself generally surgically untreatable, and not due to a cause like severe irreversible ischemia or primary valvular heart disease. Organic mitral regurgitation is seen when a disruption of the seal occurs at the free leading edge of the leaflet due to a ruptured chord or papillary muscle making the leaflet flail; or if the leaflet tissue is redundant, the valves may prolapse the level at which coaptation occurs higher into the atrium with further prolapse opening the valve higher in the atrium during ventricular systole. Functional mitral regurgitation occurs as a result of dilation of heart and mitral annulus secondary to heart failure, most often as a result of coronary artery disease or idiopathic dilated cardiomyopathy. Comparing a healthy annulus to an unhealthy annulus, the unhealthy annulus is dilated and, in particular, the anterior-to-posterior distance along the minor axis (line P-A) is increased. As a result, the shape and tension defined by the annulus becomes less oval and more round. This condition is called dilation. When the annulus is dilated, the shape and tension conducive for coaptation at peak contraction pressures progressively deteriorate.

Prior Treatment Modalities

It is reported that twenty-five percent of the six million Americans who will have congestive heart failure will have functional mitral regurgitation to some degree. This constitutes the 1.5 million people with functional mitral regurgitation. In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

By interrupting the cycle of progressive functional mitral regurgitation, it has been shown in surgical patients that survival is increased and in fact forward ejection fraction increases in many patients. The problem with surgical therapy is the significant insult it imposes on these chronically ill patients with high morbidity and mortality rates associated with surgical repair.

Currently, patient selection criteria for mitral valve surgery are very selective and typically performed only on patients having normal ventricular function, generally good health, a predicted lifespan of greater than 3 to 5 years, NYHA Class III or IV symptoms, and at least Grade 3 regurgitation. Patients that do not meet these requirements, typically older patients in poor health, are not good candidates for surgical procedures, especially open surgical procedures. Such patients benefit greatly from shorter, less invasive surgical procedures that improve valve function. However, such patients could benefit from further improvements in minimally invasive surgical procedures to deploy such valve treatment and repair implants, systems, reducing the complexity of delivery systems and duration of the procedures, as well as consistency, reliability and ease of use.

Thus, there is a need for further improvements that reduce the complexity of such delivery systems and improved methods of delivery that reduce the duration of the procedures, and improve the consistency, reliability and ease of use for the clinician in the deployment of heart implants for treatment of mitral valve regurgitation.

SUMMARY OF THE INVENTION

The present invention provides systems, methods and associated devices for delivery and deployment of heart implants for reshaping a heart valve annulus for treatment of a heart disorder, such as mitral valve regurgitation.

Accordingly, in one embodiment, the invention provides a system for delivering a heart implant. The system includes first and second magnetic catheters. The first catheter has a proximal end and a distal end and includes: i) a first lumen extending through a length of the first catheter: ii) a first magnet disposed along a distal portion of the first catheter, wherein the first magnet includes a first magnetic pole and a second magnetic pole; and iii) a first guide channel disposed in the distal portion of the first catheter and extending along a first longitudinal axis, the first guide channel being coextensive with the first lumen and having a first side hole located proximal along the distal portion of the first catheter relative to the first magnetic pole. The second catheter has a proximal end and a distal end and includes: i) a second lumen extending through the length of the second catheter: ii) a second magnet disposed at the distal end of the second catheter, wherein the second magnet includes a third magnetic pole and a fourth magnetic pole; and iii) a second guide channel disposed at the distal end of the second catheter and extending along a second longitudinal axis, the second guide channel being coextensive with the second lumen and having a second side hole adjacent the second magnet. In some aspects, the first side hole and the second side hole are aligned in a plane parallel to the first longitudinal axis and the second longitudinal axis, and the second side hole is oriented distal along the distal portion of the first catheter relative to the first side hole, when the first magnet and the second magnet are magnetically coupled.

In another embodiment, the invention provides a method of performing a surgical procedure on a subject using the system of the invention. The method includes: inserting, through a first vascular access site, the first catheter of the system of the invention, and advancing the first catheter to a first location in or proximate a heart of the subject: inserting the second catheter of the system of the invention through a second vascular access site and advancing the second catheter to a second location in or proximate the heart, the first and second locations being separated by a tissue wall of the heart: positioning the first catheter and the second catheter such that the first magnet and the second magnet magnetically couple across the tissue wall; and penetrating the tissue wall with a penetrating member advanced through the first catheter, across the tissue wall and through the second catheter while the first and second catheters are magnetically coupled, thereby performing a surgical procedure on the subject. In some aspects, the method further includes determining the depth of insertion of the first and/or second catheter via the radiopaque markers disposed along the respective lengths of the catheters before magnetic coupling of the first magnet and the second magnet. In some aspects, the method further includes advancing a posterior anchor and a bridging element coupled at a first end of the bridging element to the posterior anchor to the first location from the first vascular access site while the first magnet and second magnet are magnetically coupled, advancing a second end of the bridging element through the penetrated tissue wall and into the second catheter, and advancing an anterior anchor along the bridging element from the second vascular access site and deploying the anterior anchor at a third location in the heart, the bridging element spanning across a chamber of the heart.

In another embodiment, the invention provides a method of performing a surgical procedure on a subject using the system of the invention. The includes: inserting, through a first vascular access site, the first catheter of the system of the invention, and advancing the first catheter to a first location in or proximate a heart of the subject: inserting the second catheter of the system of the invention through a second vascular access site and advancing the second catheter to a second location in or proximate the heart, the first and second locations being separated by a tissue wall of the heart: positioning the first catheter and the second catheter such that the first magnet and the second magnet magnetically couple across the tissue wall; and penetrating the tissue wall with a penetrating member advanced through the first catheter or the second catheter and across the tissue wall while the first and second catheters are magnetically coupled, thereby performing a surgical procedure on the subject.

In yet another embodiment, the invention provides a method of treating mitral valve regurgitation in a subject by reshaping a heart chamber of the subject. The method includes: inserting, through a first vascular access site, the first catheter of the system of the invention, and advancing the first catheter to a first location in or proximate a heart of the subject: inserting the second catheter of the system of the invention through a second vascular access site and advancing the second catheter to a second location in or proximate the heart, the first and second locations being separated by a tissue wall of the heart: positioning the first catheter and the second catheter such that the first magnet and the second magnet magnetically couple across the tissue wall: penetrating the tissue wall with a penetrating member advanced through the first catheter, across the tissue wall and through the second catheter while the first and second catheters are magnetically coupled: advancing a posterior anchor and a bridging element coupled at a first end of the bridging element to the posterior anchor to the first location from the first vascular access site while the first magnet and second magnet are magnetically coupled, advancing a second end of the bridging element through the penetrated tissue wall and into the second catheter: advancing an anterior anchor along the bridging element from the second vascular access site and deploying the anterior anchor at a third location in the heart, the bridging element spanning across a chamber of the heart; and shortening a length of the bridging element thereby reshaping the chamber of the heart and coupling the second end of the bridging element to the deployed anterior anchor while the chamber of the heart is reshaped so that the chamber of the heart remains reshaped, thereby treating mitral valve regurgitation in the subject. In some aspects, the method further includes determining the depth of insertion of the first and/or second catheter via the radiopaque markers disposed along the respective lengths of the catheters before magnetic coupling of the first magnet and the second magnet.

In another embodiment, the invention provides a method of treating mitral valve regurgitation in a subject by reshaping a heart chamber of the subject. The method includes: inserting, through a first vascular access site, the first catheter of the system of the invention, and advancing the first catheter to a first location in or proximate a heart of the subject: inserting the second catheter of the system of the invention through a second vascular access site and advancing the second catheter to a second location in or proximate the heart, the first and second locations being separated by a tissue wall of the heart: positioning the first catheter and the second catheter such that the first magnet and the second magnet magnetically couple across the tissue wall: penetrating the tissue wall with a penetrating member advanced through the first catheter or the second catheter and across the tissue wall while the first and second catheters are magnetically coupled: advancing a posterior anchor and a bridging element coupled at a first end of the bridging element to the posterior anchor to the first location while the first magnet and second magnet are magnetically coupled: advancing a second end of the bridging element through the penetrated tissue wall when the posterior anchor is advanced through the first catheter: advancing an anterior anchor along the bridging element and deploying the anterior anchor at a third location in the heart, the bridging element spanning across a chamber of the heart; and shortening a length of the bridging element thereby reshaping the chamber of the heart and coupling the second end of the bridging element to the deployed anterior anchor while the chamber of the heart is reshaped so that the chamber of the heart remains reshaped, thereby treating mitral valve regurgitation in the subject.

In another embodiment, the invention provides a method of treating mitral valve regurgitation in a subject by reshaping a heart chamber of the subject. The method includes: inserting, through a first vascular access site, the first catheter of the system of the invention, and advancing the first catheter to a first location in or proximate a heart of the subject: inserting the second catheter of the system of the invention through a second vascular access site and advancing the second catheter to a second location in or proximate the heart, the first and second locations being separated by a tissue wall of the heart: positioning the first catheter and the second catheter such that the first magnet and the second magnet magnetically couple across the tissue wall: penetrating the tissue wall with a penetrating member advanced through the second catheter and across the tissue wall while the first and second catheters are magnetically coupled: advancing a posterior anchor and a bridging element coupled at a first end of the bridging element to the posterior anchor to the first location while the first magnet and second magnet are magnetically coupled: advancing an anterior anchor along the bridging element and deploying the anterior anchor at a third location in the heart, the bridging element spanning across a chamber of the heart; and shortening a length of the bridging element thereby reshaping the chamber of the heart and coupling the second end of the bridging element to the deployed anterior anchor while the chamber of the heart is reshaped so that the chamber of the heart remains reshaped, thereby treating mitral valve regurgitation in the subject.

In still another embodiment, the invention provides a catheter system for measuring insertion depth of a catheter within an anatomical vessel. The catheter system includes: an elongated overtube having a lumen, a proximal end, a distal end, and an expandable member disposed at the distal end of the catheter: a catheter slidably disposed within the lumen of the of the overtube; and a depth measurement mechanism. In various aspects, the catheter includes a proximal end, a distal end, and a handle disposed at the proximal end of the catheter. In various aspects, the depth measurement mechanism is slidably coupled to the handle at a proximal end of the mechanism and coupled to the overtube at a distal end of the mechanism, wherein the mechanism is configured to measure movement of the catheter along the lumen of the overtube when the distal end of the catheter is advanced distal to the distal end of the overtube when the expandable member is inflated. In some aspects, the catheter of the system is the first catheter of the invention.

In another embodiment, the invention provides a method for measuring insertion depth within an anatomical vessel. The method includes advancing the catheter system of the invention into an anatomical vessel. The inflation member is then expanded so that the overtube remains stationary within the vessel. The method further includes advancing the distal end of the catheter distal to the distal end of the overtube and measuring via the measurement mechanism a distance the distal end of the catheter is advanced distal to the distal end of the overtube, thereby measuring insertion depth of the catheter within the anatomical vessel.

In yet another embodiment, the invention provides a method of treating mitral valve regurgitation in a subject by reshaping a heart chamber of the subject. The method includes: inserting, through a first vascular access site, the catheter system of the invention including an overtube, and advancing the overtube and the first catheter of the system of the invention along the vascular access: inflating the expandable member so that the overtube remain stationary in the vascular access: advancing the first catheter to a first location in or proximate a heart of the subject, wherein the first location is determined by measuring a depth of insertion via the measuring mechanism: inserting the second catheter of the system of the invention through a second vascular access site and advancing the second catheter to a second location in or proximate the heart, the first and second locations being separated by a tissue wall of the heart: positioning the first catheter and the second catheter such that the first magnet and the second magnet magnetically couple across the tissue wall: penetrating the tissue wall with a penetrating member advanced through the first catheter or the second catheter across the tissue wall while the first and second catheters are magnetically coupled: advancing a posterior anchor and a bridging element coupled at a first end of the bridging element to the posterior anchor to the first location while the first magnet and second magnet are magnetically coupled, advancing a second end of the bridging element through the penetrated tissue wall and into the second catheter when the posterior anchor is advanced through the first catheter: advancing an anterior anchor along the bridging element and deploying the anterior anchor at a third location in the heart, the bridging element spanning across a chamber of the heart; and shortening a length of the bridging element thereby reshaping the chamber of the heart and coupling the second end of the bridging element to the deployed anterior anchor while the chamber of the heart is reshaped so that the chamber of the heart remains reshaped, thereby treating mitral valve regurgitation in the subject.

In still another embodiment, the invention provides a method of treating mitral valve regurgitation in a subject by reshaping a heart chamber of the subject. The method includes: inserting, through a first vascular access site, the catheter system of the invention including an overtube, and advancing the overtube and the first catheter of the system of the invention along the vascular access: inflating the expandable member so that the overtube remain stationary in the vascular access: advancing the first catheter to a first location in or proximate a heart of the subject, wherein the first location is determined by measuring a depth of insertion via the measuring mechanism; inserting the second catheter of the system of the invention through a second vascular access site and advancing the second catheter to a second location in or proximate the heart, the first and second locations being separated by a tissue wall of the heart: positioning the first catheter and the second catheter such that the first magnet and the second magnet magnetically couple across the tissue wall: penetrating the tissue wall with a penetrating member advanced through the second catheter across the tissue wall while the first and second catheters are magnetically coupled: advancing a posterior anchor and a bridging element coupled at a first end of the bridging element to the posterior anchor to the first location while the first magnet and second magnet are magnetically coupled: advancing an anterior anchor along the bridging element and deploying the anterior anchor at a third location in the heart, the bridging element spanning across a chamber of the heart; and shortening a length of the bridging element thereby reshaping the chamber of the heart and coupling the second end of the bridging element to the deployed anterior anchor while the chamber of the heart is reshaped so that the chamber of the heart remains reshaped, thereby treating mitral valve regurgitation in the subject.

DETAILED DESCRIPTION OF THE INVENTION

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
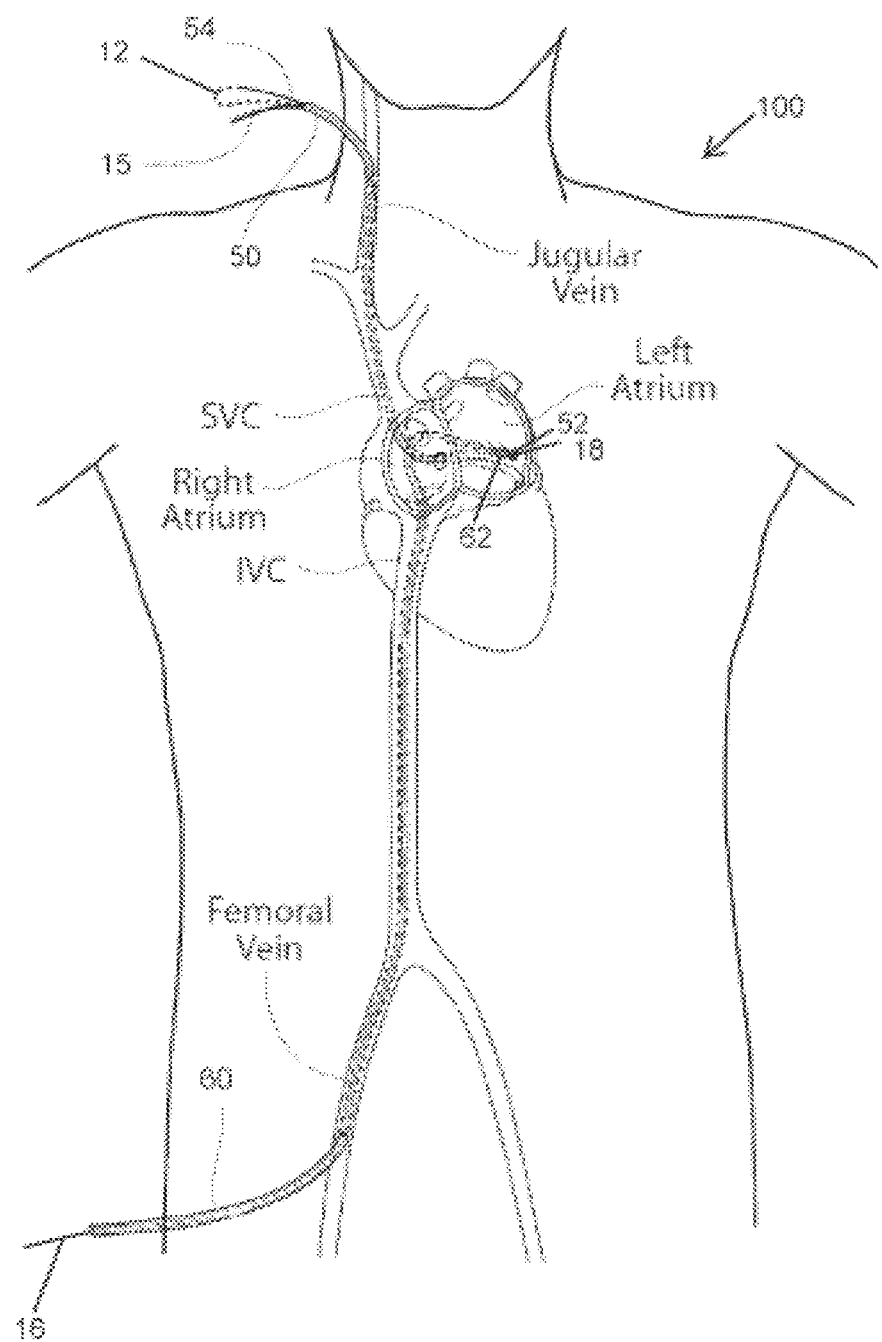
FIG. 1 depicts an overview of a catheter system for intravascular delivery of a heart implant for treatment of mitral regurgitation, in accordance with embodiments of the invention.
Figure 13:
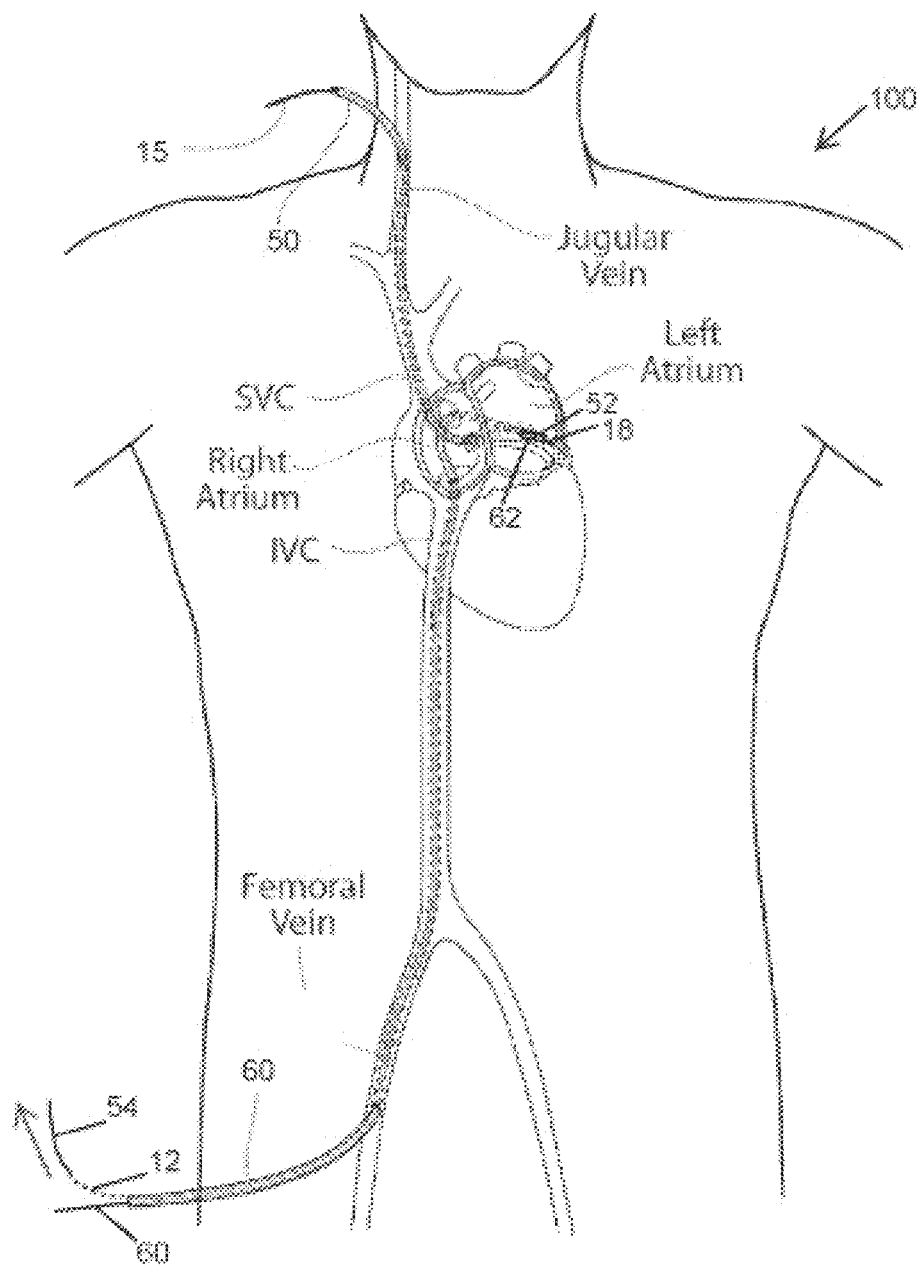
FIG. 13 shows a catheter-based delivery system for deployment of an implant system in which a bridging element attached to an anchor has been fed from a first vascular access point to a second vascular access point while first and second catheters are magnetically coupled, in accordance with aspects of the invention.

FIG. 1 shows an example embodiment of a catheter-based delivery system in accordance with aspects of the invention. The delivery system utilizes a pair of magnetic catheters that are advanced from separate vascular access points and magnetically coupled across a tissue within the heart. The pair of catheters include a great cardiac vein (GCV) anchor delivery catheter 50 which is introduced from the jugular vein and advanced along a superior vena cava (SVC) approach to the GCV, and a left atrial (LA) catheter 60, which is introduced at the femoral vein and introduced along an inferior vena cava (IVC) approach, across the inter-atrial septum and into the left atrium. Each catheter includes a magnetic head along a distal portion thereof (magnetic head 52 of catheter 50 and magnetic head 62 of catheter 60) such that when magnetically coupled, the catheters provide a stable region to facilitate penetration of a tissue wall between the LA and GCV and subsequent advancement of the puncturing guidewire 54 through the GCV catheter 50 and into the LA catheter 60. Notably, a trailing end of the puncturing guidewire 54 is attached to one end of a bridging element 12 (for example, suture), the other end of which is attached to posterior anchor 18 disposed on the distal portion of GCV catheter 50. Such a configuration allows the bridging element 12 to be advanced across the left atrium by advancing the puncturing guidewire 54 through the LA catheter 60 to exit from the femoral vein, while the magnetic heads remain magnetically coupled to each other, as shown in FIG. 13. As can be understood by referring to FIG. 13, the penetrating guidewire 54 has a length greater than the combined length of the catheters such that the guidewire 54 can be manually advanced externally from one vascular access point until the guidewire 54 exits the other vascular access point due to the stiffness of the guidewire 54. The guidewire 54 can be further retracted after exiting so as to pull the attached bridging element through the vascular path until the bridging element also exits the same vascular access point. Performing this process while the GCV catheter 50 and LA catheter 60 are magnetically coupled provides improved stability during the process and, more importantly, covers the puncturing guidewire 54 and bridging element 12 while being pulled across the delicate tissues of the heart. The benefits of such a configuration, as compared to conventional delivery approaches, include improved safety for the patient, single operator deployment, significantly reduced duration of the deployment procedure and reduced delivery device lengths and cost of goods. The advantages of such an approach in deploying the implant can be understood further by referred to the following figures, which describe the implant and associated components in more detail as well as conventional approaches of delivery and deploying such implants.

Heart Implants for Treatment/Repair of a Heart Valve Annulus

Implant Structure

Figure 3A:
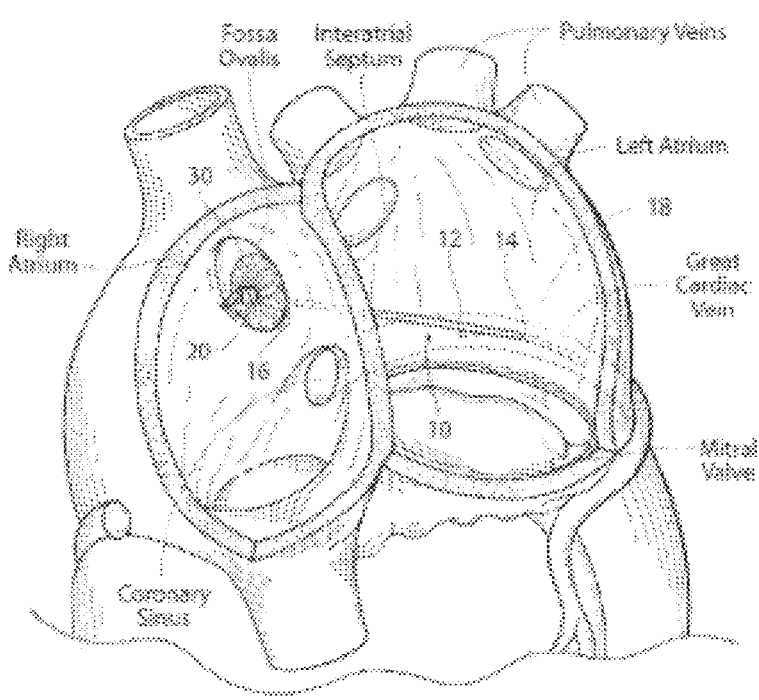
FIG. 3A is an anatomic anterior perspective view of the left and right atriums, with portions broken away and in section to show the presence of an implant system with an inter-atrial bridging element that spans the mitral valve annulus between a posterior anchor positioned in the great cardiac vein and an anterior anchor within the inter-atrial septum, which is suitable for delivery with catheter systems and delivery methods of the invention.
Figure 3B:
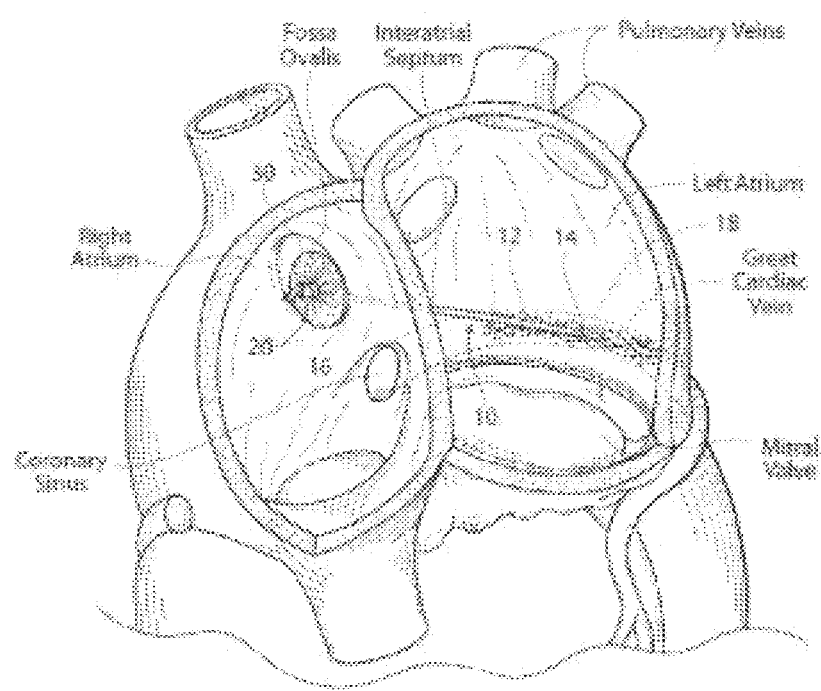
FIG. 3B is an anatomic anterior perspective view of the left and right atriums, with portions broken away and in section to show the presence of an implant system with an inter-atrial bridging element that spans the mitral valve annulus between a posterior anchor positioned in the great cardiac vein and an anterior anchor within the inter-atrial septum, which is suitable for delivery with catheter systems and delivery methods of the invention.

FIGS. 3A-3B show embodiments of an implant 10 that is sized and configured to extend across the left atrium in generally an anterior-to-posterior direction, spanning the mitral valve annulus. The implant 10 comprises a spanning region or bridging element 12 having a posterior anchor region 14 and an anterior anchor region 16.

The posterior anchor region 14 is sized and configured to allow the bridging element 12 to be placed in a region of atrial tissue above the posterior mitral valve annulus. This region is preferred, because it generally presents more tissue mass for obtaining purchase of the posterior anchor region 14 than in a tissue region at or adjacent to the posterior mitral annulus. Engagement of tissue at this supra-annular location also may reduce risk of injury to the circumflex coronary artery. In a small percentage of cases, the circumflex coronary artery may pass over and medial to the great cardiac vein on the left atrial aspect of the great cardiac vein, coming to lie between the great cardiac vein and endocardium of the left atrium. However, since the forces in the posterior anchor region are directed upward and inward relative to the left atrium and not in a constricting manner along the long axis of the great cardiac vein, the likelihood of circumflex artery compression is less compared to other technologies in this field that do constrict the tissue of the great cardiac vein. Nevertheless, should a coronary angiography reveal circumflex artery stenosis, the symmetrically shaped posterior anchor may be replaced by an asymmetrically shaped anchor, such as where one limb of a T-shaped member is shorter than the other, thus avoiding compression of the crossing point of the circumflex artery. The asymmetric form may also be selected first based on a pre-placement angiogram.

An asymmetric posterior anchor may be utilized for other reasons as well. The asymmetric posterior anchor may be selected where a patient is found to have a severely stenotic distal great cardiac vein, where the asymmetric anchor better serves to avoid obstruction of that vessel. In addition, an asymmetric posterior anchor may be chosen for its use in selecting application of forces differentially and preferentially on different points along the posterior mitral annulus to optimize treatment, for example, in cases of malformed or asymmetrical mitral valves.

The anterior anchor region 16 is sized and configured to allow the bridging element 12 to be placed, upon passing into the right atrium through the septum, adjacent tissue in or near the right atrium. For example, as is shown in FIGS. 3A-3B, the anterior anchor region 16 may be adjacent or abutting a region of fibrous tissue in the interatrial septum. As shown, the anchor site 16 is desirably superior to the anterior mitral annulus at about the same elevation or higher than the elevation of the posterior anchor region 14. In the illustrated embodiment, the anterior anchor region 16 is adjacent to or near the inferior rim of the fossa ovalis.

Alternatively, the anterior anchor region 16 can be located at a more superior position in the septum, for example, at or near the superior rim of the fossa ovalis. The anterior anchor region 16 can also be located in a more superior or inferior position in the septum, away from the fossa ovalis, provided that the anchor site does not harm the tissue in the region.

Alternatively, the anterior anchor region 16, upon passing through the septum into the right atrium, may be positioned within or otherwise extend to one or more additional anchors situated in surrounding tissues or along surrounding areas, such as within the superior vena cava (SVC) or the inferior vena cava (IVC).

Figure 2A:
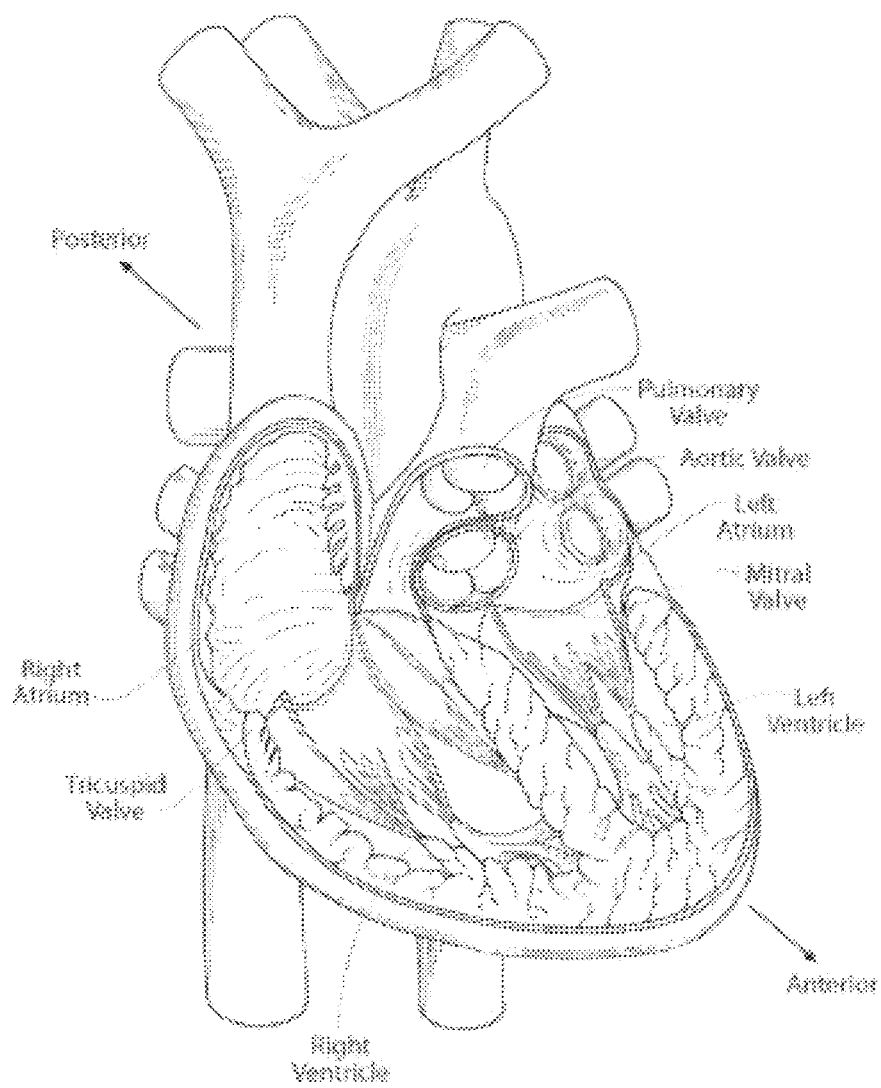
FIG. 2A is an anatomic anterior view of a human heart, with portions broken away and in section to view the interior heart chambers and adjacent structures.
Figure 2B:
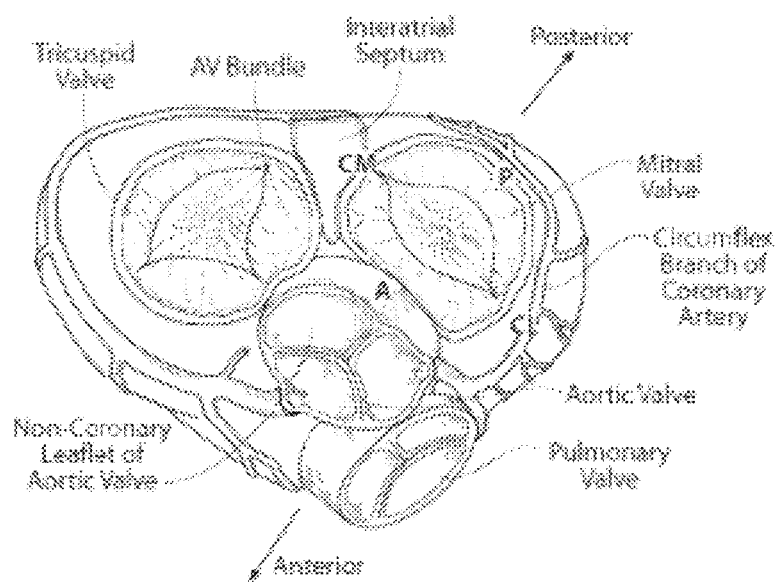
FIG. 2B is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.
Figure 2C:
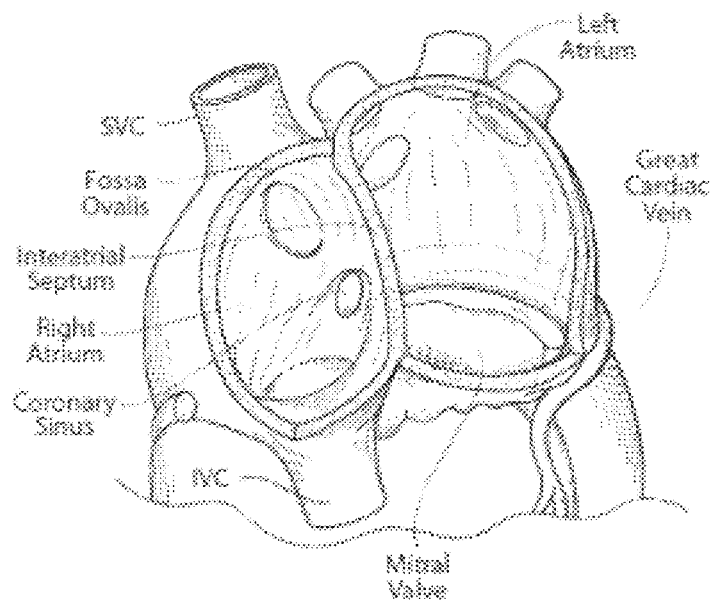
FIG. 2C is an anatomic superior view of a section of the human heart shown in FIG. 2B, with the tricuspid and mitral valves closed and the aortic and pulmonary valves opened during ventricular systole (ventricular emptying) of the cardiac cycle.
Figure 2D:
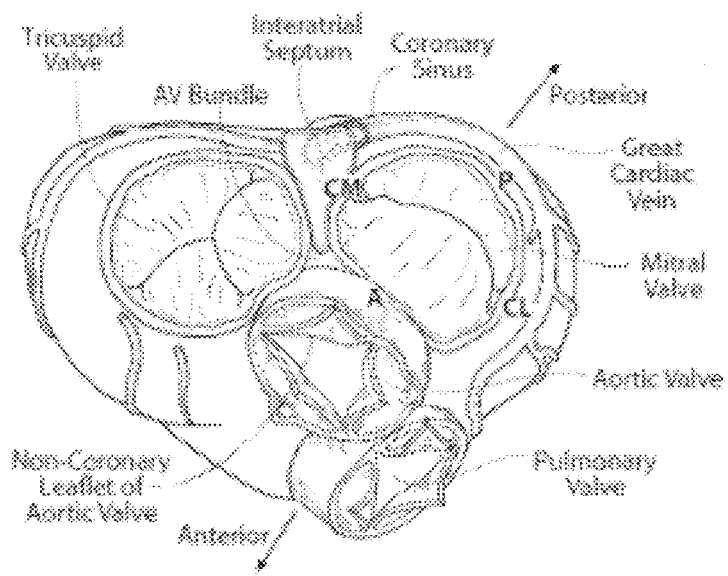
FIG. 2D is an anatomic anterior perspective view of the left and right atriums, with portions broken away and in section to show the interior of the heart chambers and associated structures, such as the fossa ovalis, coronary sinus, and the great cardiac vein.
Figure 2E:
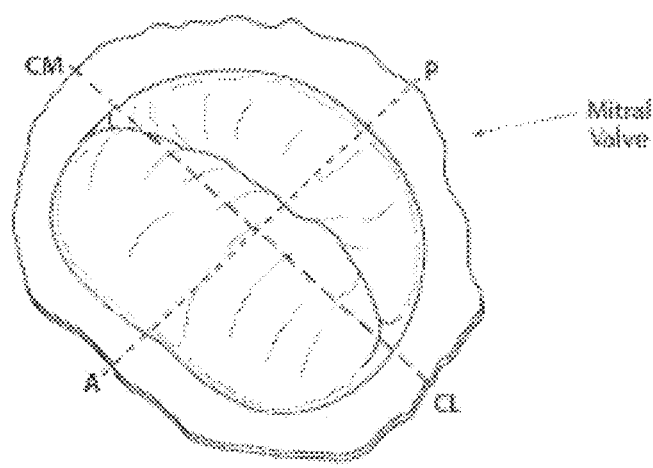
FIG. 2E is a superior view of a healthy mitral valve, with the leaflets closed and coapting at peak contraction pressures during ventricular systole.
Figure 2F:
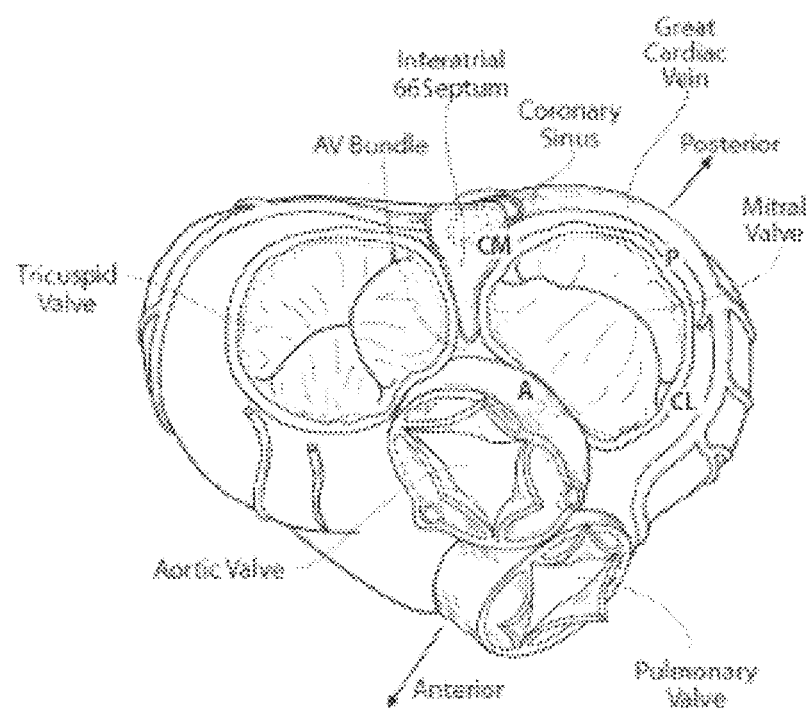
FIG. 2F is an anatomic superior view of a section of the human heart, with the normal mitral valve shown in FIG. 2E closed during ventricular systole (ventricular emptying) of the cardiac cycle.
Figure 2G:
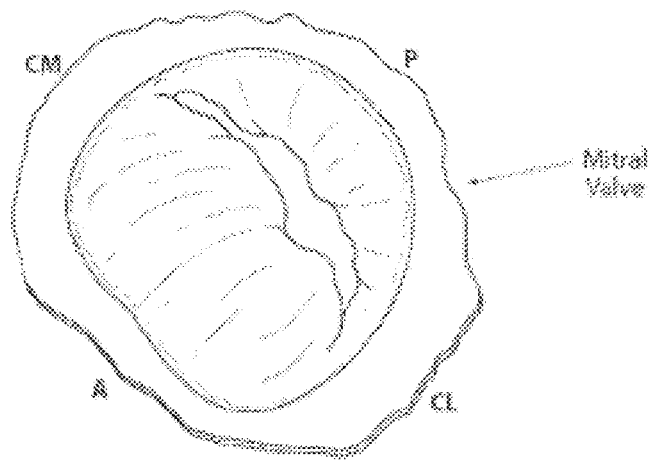
FIG. 2G is a superior view of a dysfunctional mitral valve, with the leaflets failing to coapt during peak contraction pressures during ventricular systole, leading to mitral regurgitation.

In use, the spanning region or bridging element 12 can be placed into tension between the two anchor regions 14 and 16. The implant 10 thereby serves to apply a direct mechanical force generally in a posterior to anterior direction across the left atrium. The direct mechanical force can serve to shorten the minor axis (along line P-A in FIG. 2E) of the annulus. In doing so, the implant 10 can also reactively reshape the annulus along its major axis (line CM-CL in FIG. 2E) and/or reactively reshape other surrounding anatomic structures. It should be appreciated, however, the presence of the implant 10 can serve to stabilize tissue adjacent the heart valve annulus, without affecting the length of the minor or major axes.

It should also be appreciated that, when situated in other valve structures, the axes affected may not be the "major" and "minor" axes, due to the surrounding anatomy. In addition, in order to be therapeutic, the implant 10 may only need to reshape the annulus during a portion of the heart cycle, such as during late diastole and early systole when the heart is most full of blood at the onset of ventricular systolic contraction, when most of the mitral valve leakage occurs. For example, the implant 10 may be sized to restrict outward displacement of the annulus during late ventricular diastolic relaxation as the annulus dilates.

The mechanical force applied by the implant 10 across the left atrium can restore to the heart valve annulus and leaflets a more normal anatomic shape and tension. The more normal anatomic shape and tension are conducive to coaptation of the leaflets during late ventricular diastole and early ventricular systole, which, in turn, reduces mitral regurgitation.

In its most basic form, the implant 10 is made from a biocompatible metallic or polymer material, or a metallic or polymer material that is suitably coated, impregnated, or otherwise treated with a material to impart biocompatibility, or a combination of such materials. The material is also desirably radiopaque or incorporates radiopaque features to facilitate fluoroscopic visualization.

In some embodiments, the implant 10, or at least a portion thereof, can be formed by bending, shaping, joining, machining, molding, or extrusion of a metallic or polymer wire form structure, which can have flexible or rigid, or inelastic or elastic mechanical properties, or combinations thereof. In other embodiments, the implant 10, or at least a portion thereof, can be formed from metallic or polymer thread-like or suture material. Materials from which the implant 10 can be formed include, but are not limited to, stainless steel, Nitinol, titanium, silicone, plated metals, Elgiloy™, NP55, and NP57.

In any of the implants described herein, the bridging member can be formed of a substantially inelastic material, such as a thread-like or suture material.

The Posterior Anchor Region

The posterior anchor region 14 is sized and configured to be located within or at the left atrium at a supra-annular position, for example, positioned within or near the left atrium wall above the posterior mitral annulus.

In the illustrated embodiment, the posterior anchor region 14 is shown to be located generally at the level of the great cardiac vein, which travels adjacent to and parallel to the majority of the posterior mitral valve annulus. This extension of the coronary sinus can provide a strong and reliable fluoroscopic landmark when a radiopaque device is placed within it or contrast dye is injected into it. As previously described, securing the bridging element 12 at this supra-annular location also lessens the risk of encroachment of and risk of injury to the circumflex coronary artery compared to procedures applied to the mitral annulus directly. Furthermore, the supra-annular position assures no contact with the valve leaflets therefore allowing for coaptation and reduces the risk of mechanical damage.

The great cardiac vein also provides a site where relatively thin, non-fibrous atrial tissue can be readily augmented and consolidated. To enhance hold or purchase of the posterior anchor region 14 in what is essentially non-fibrous heart tissue, and to improve distribution of the forces applied by the implant 10, the posterior anchor region 14 may include a posterior anchor 18 placed within the great cardiac vein and abutting venous tissue. This makes possible the securing of the posterior anchor region 14 in a non-fibrous portion of the heart in a manner that can nevertheless sustain appreciable hold or purchase on that tissue for a substantial period of time, without dehiscence, expressed in a clinically relevant timeframe.

The Anterior Anchor Region

The anterior anchor region is sized and configured to allow the bridging element 12 to remain firmly in position adjacent or near the fibrous tissue and the surrounding tissues in the right atrium side of the atrial septum. The fibrous tissue in this region provides superior mechanical strength and integrity compared with muscle and can better resist a device pulling through. The septum is the most fibrous tissue structure in its own extent in the heart.

Surgically handled, it is usually one of the only heart tissues into which sutures actually can be placed and can be expected to hold without pledgets or deep grasps into muscle tissue, where the latter are required.

As shown in FIGS. 3A-3B, the anterior anchor region 16 passes through the septal wall at a supra-annular location above the plane of the anterior mitral valve annulus. The supra-annular distance on the anterior side can be generally at or above the supra-annular distance on the posterior side. The anterior anchor region 16 is shown at or near the inferior rim of the fossa ovalis, although other more inferior or more superior sites can be used within or outside the fossa ovalis, taking into account the need to prevent harm to the septal tissue and surrounding structures.

By locating the bridging element 12 at this supra-annular level within the right atrium, which is fully outside the left atrium and spaced well above the anterior mitral annulus, the implant 10 avoids the impracticalities of endovascular attachment at or adjacent to the anterior mitral annulus, where there is just a very thin rim of annulus tissue that is bounded anteriorly by the anterior leaflet, inferiorly by the aortic outflow tract, and medially by the atrioventricular node of the conduction system. The anterior mitral annulus is where the non-coronary leaflet of the aortic valve attaches to the mitral annulus through the central fibrous body. Anterior location of the implant 10 in the supra-annular level within the right atrium (either in the septum or in a vena cava) avoids encroachment of and risk of injury to both the aortic valve and the AV node.

Figure 5A:
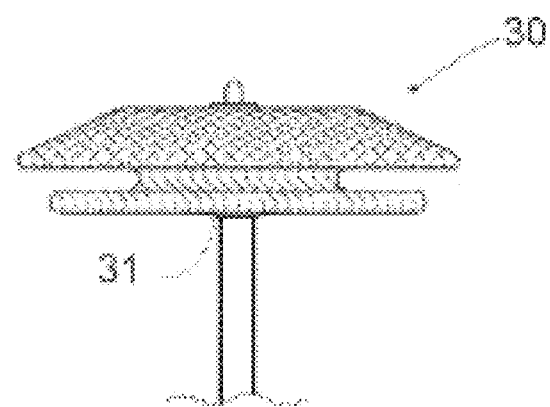
FIG. 5A shows a detailed view of an example anterior anchor of the implant that is suitable for anchoring within the patent fossa ovalis of the inter-atrial septum.

The purchase of the anterior anchor region 16 in fibrous septal tissue is desirably enhanced by a septal member 30 or an anterior anchor 20, or a combination of both. FIGS. 3A and 3B show the anterior anchor region including a septal member 30. The septal member 30 may be an expandable device and also may be a commercially available device such as a septal occluder, for example, Amplatzer® PFO Occluder (see FIGS. 5A-5B). The septal member 30 preferably mechanically amplifies the hold or purchase of the anterior anchor region 16 in the fibrous tissue site. The septal member 30 also desirably increases reliance, at least partly, on neighboring anatomic structures of the septum to make firm the position of the implant 10. In addition, the septal member 30 may also serve to plug or occlude the small aperture that was created in the fossa ovalis or surrounding area during the implantation procedure.

Anticipating that pinpoint pulling forces will be applied by the anterior anchor region 16 to the septum, the forces acting on the septal member 30 should be spread over a moderate area, without causing impingement on valve, vessels or conduction tissues. With the pulling or tensioning forces being transmitted down to the annulus, shortening of the minor axis is achieved. A flexurally stiff septal member is preferred because it will tend to cause less focal narrowing in the direction of bridge element tension of the left atrium as tension on the bridging element is increased. The septal member 30 should also have a low profile configuration and highly washable surfaces to diminish thrombus formation for devices deployed inside the heart. The septal member may also have a collapsed configuration and a deployed configuration. The septal member 30 may also include a hub 31 (see FIGS. 5A and 5B) to allow attachment of the anchor 20. A septal brace may also be used in combination with the septal member 30 and anterior anchor 20 to distribute forces uniformly along the septum. Alternatively, devices in the IVC or the SVC can be used as anchor sites, instead of confined to the septum.

Location of the posterior and anterior anchor regions 14 and 16 having radiopaque bridge locks and well demarcated fluoroscopic landmarks respectively at the supra-annular tissue sites just described, not only provides freedom from key vital structure damage or local impingement, for example, to the circumflex artery, AV node, and the left coronary and noncoronary cusps of the aortic valve: but the supra-annular focused sites are also not reliant on purchase between tissue and direct tension-loaded penetrating/biting/holding tissue attachment mechanisms. Instead, physical structures and force distribution mechanisms such as stents, T-shaped members, and septal members can be used, which better accommodate the attachment or abutment of mechanical levers and bridge locks, and through which potential tissue tearing forces can be better distributed. Further, the anchor sites 14, 16 do not require the operator to use complex imaging. Adjustment of implant position after or during implantation is also facilitated, free of these constraints. The anchor sites 14, 16 also make possible full intra-atrial retrieval of the implant 10 by endovascularly snaring and then cutting the bridging element 12 at either side of the left atrial wall, from which it emerges.

Orientation of the Bridging Element

In the embodiments shown in FIGS. 3A-3B, the implant 10 is shown to span the left atrium beginning at a posterior point of focus superior to the approximate mid-point of the mitral valve annulus, and proceeding in an anterior direction in a generally straight path directly to the region of anterior focus in the septum. The spanning region or bridging element 12 of the implant 10 may be preformed or otherwise configured to extend in this essentially straight path above the plane of the valve, without significant deviation in elevation toward or away from the plane of the annulus, other than as dictated by any difference in elevation between the posterior and anterior regions of placement. It is appreciated that such implants can include bridging member with lateral or medial deviations and/or superior or inferior deviations and can include bridging members that are rigid or semi-rigid and/or substantially fixed in length.

Posterior and Anterior Anchors

Figure 4A:
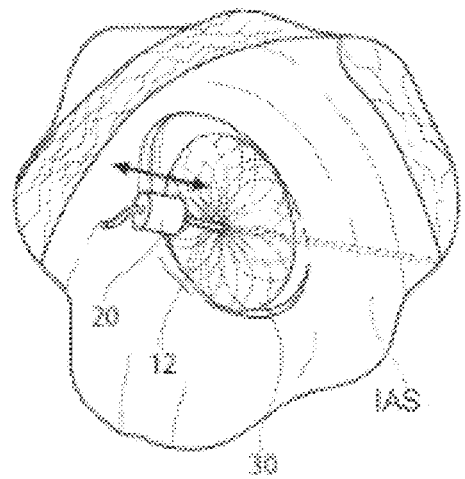
FIG. 4A is a detailed view showing an anterior anchor deployed within the fossa ovalis of the inter-atrial septum and the posterior anchor deployed within the great cardiac vein.
Figure 4B:
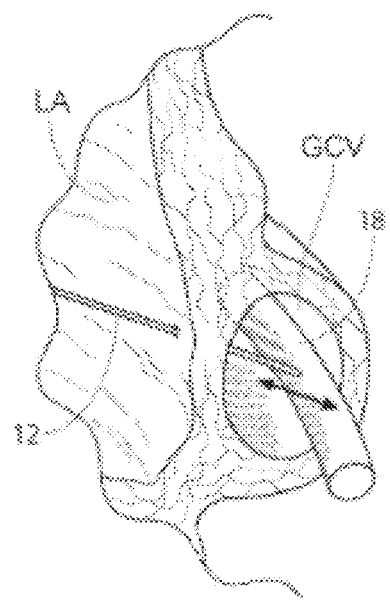
FIG. 4B as a detailed view showing an anterior anchor deployed within the fossa ovalis of the inter-atrial septum and the posterior anchor deployed within the great cardiac vein.

It is to be appreciated that an anchor as described herein, including a posterior or anterior anchor, describes an apparatus that may releasably hold the bridging element 12 in a tensioned state. As can be seen in FIGS. 4A-4B, anchors 20 and 18 respectively are shown releasably secured to the bridging element 12, allowing the anchor structure to move back and forth independent of the inter-atrial septum and inner wall of the great cardiac vein during a portion of the cardiac cycle when the tension force may be reduced or becomes zero.

Alternative embodiments are also described, all of which may provide this function. It is also to be appreciated that the general descriptions of posterior and anterior anchors are non-limiting to the anchor function, for example, a posterior anchor may be used anterior, and an anterior anchor may be used posterior.

When the bridging element is in an abutting relationship to a septal member (for example, anterior anchor) or a T-shaped member (for example, posterior anchor), for example, the anchor allows the bridging element to move freely within or around the septal member or T-shaped member, for example, the bridging element is not connected to the septal member or T-shaped member. In this configuration, the bridging element is held in tension by the locking bridge stop, whereby the septal member or T-shaped member serves to distribute the force applied by the bridging element across a larger surface area. Alternatively, the anchor may be mechanically connected to the septal member or T-shaped member, for example, when the bridge stop is positioned over and secured to the septal member hub. In this configuration, the bridging element is fixed relative to the septal member position and is not free to move about the septal member.

Figure 6A:
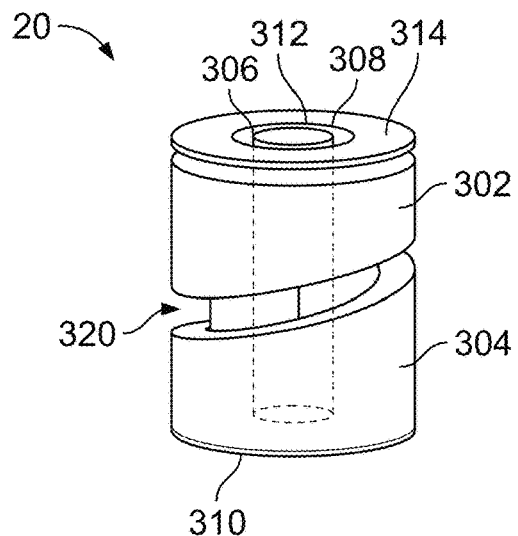
FIG. 6A shows an example locking bridge stop for locking the bridging element relative the anterior anchor of the implant.
Figure 6B:
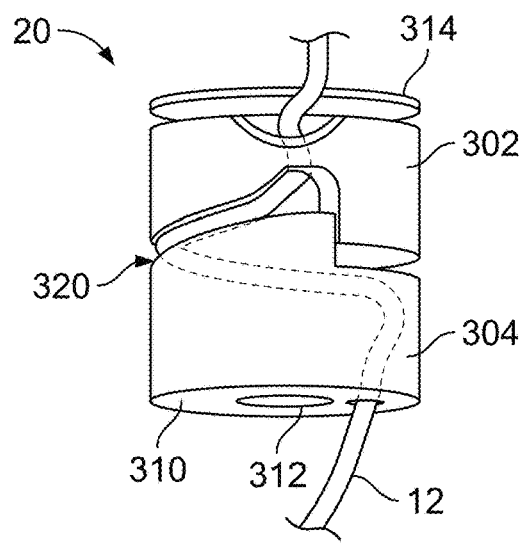
FIG. 6B shows an example locking bridge stop for locking the bridging element relative the anterior anchor of the implant.

FIGS. 6A-6B show perspectives views of an example locking bridge stop 20 in accordance with the present invention. Each bridge stop 20 preferably includes a fixed upper body 302 and a movable lower body 304. Alternatively, the upper body 302 may be movable and the lower body 304 may be fixed. The upper body 302 and lower body 304 are positioned circumjacent a tubular shaped rivet 306. The upper body 302 and lower body 304 are preferably held in position by the rivet head 308 and a base plate 310. The rivet 306 and base plate 310 includes a predetermined inner diameter 312, sized so as to allow the bridge stop 300 to be installed over a guidewire. A spring, such as a spring washer 314, or also known in the mechanical art as a Belleville Spring, is positioned circumjacent the rivet 306 and between the rivet head 308 and the upper body 302, and applies an upward force on the lower body 304. The lower body 304 is movable between a bridge unlocked position (see FIG. 6A), and a bridge locked position (see FIG. 6B). In the bridge unlocked position, the lower body 304 and the upper body 302 are not in contacting communication, creating a groove 320 between the upper body 302 and lower body 304. In the bridge locked position, the axial force of the spring washer 314 urges the lower body 304 into contacting, or near contacting communication with the upper body 302, whereby the bridging element 12, which has been positioned within the groove 320, is locked in place by the axial force of the lower body 304 being applied to the upper body 302. In use, the bridging element 12 is positioned within the groove 320 while the lower body 304 is maintained in the bridge unlocked position 316. The bridge stop 300 is positioned against the septal member 30 and the bridging element 12 is adjusted to proper tension. The lower body 304 is then allowed to move toward the upper body 302, thereby fixing the position of the bridge stop 300 on the bridging element 12. While this example depicts a particular locking bridge stop design, it is appreciated that any suitable lock could be used, including any of the types described in U.S. Patent Application Publication No. 2017/0055969.

Figure 7A:
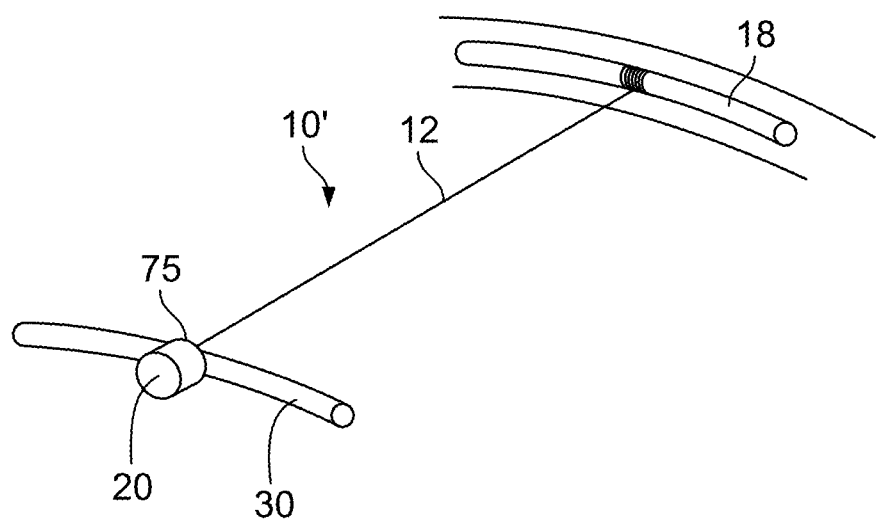
FIG. 7A shows an alternative example of a heart implant suitable for intravascular delivery, in accordance with aspects of the invention.
Figure 7B:
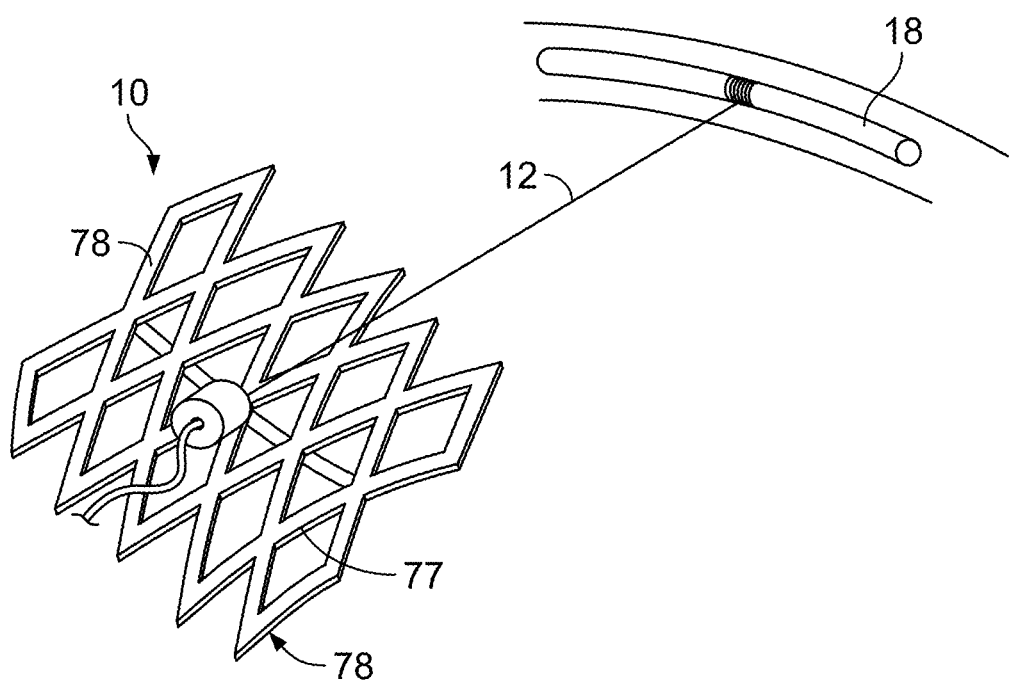
FIG. 7B shows an alternative example of a heart implant suitable for intravascular delivery, in accordance with aspects of the invention.

FIGS. 7A-7B show alternative heart implants suitable for delivery with the methods and delivery systems described herein. FIG. 7A shows an implant 10' having a T-shaped posterior anchor 18 in the great cardiac vein and T-shaped anterior anchor 70. The anterior T-shaped bridge stop 75 may be of a construction of any of the T-shaped bridge stop embodiments described. The T-shaped member 75 includes a lumen 75 extending through the T-shaped member 75 perpendicular to the length of the T-shaped member. The bridging element 12 may be secured by a free floating bridge stop as previously described. FIG. 7B shows an implant 10" having a T-shaped posterior anchor 18 in the great cardiac vein and a lattice style anterior anchor 76. The lattice 77 is positioned on the septal wall at or near the fossa ovalis. Optionally, the lattice 77 may include a reinforcement strut 78 to distribute the bridging element 12 tension forces over a greater area on the septal wall. The anterior lattice style bridge stop 76 may be packed in a deployment catheter with the bridging element 12 passing through its center. The lattice 77 is preferably self-expanding and may be deployed by a plunger. The bridging element 12 may be secured by a free floating bridge stop as previously described. It is appreciated that various other such implants could be devised that utilized the same concepts as in the above described implants for delivery and deployment with the systems and methods described herein.

Figure 8A:
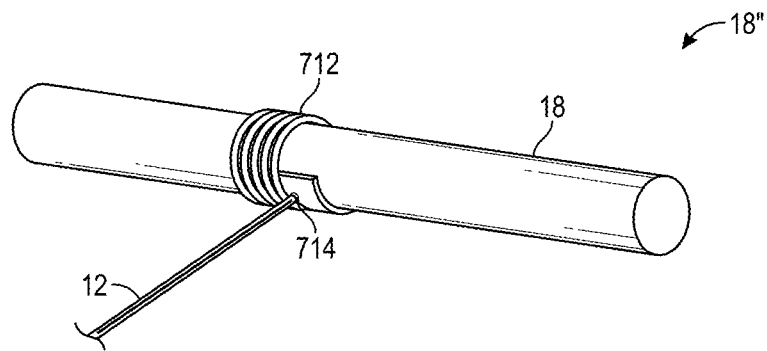
FIG. 8A shows an alternative example of posterior anchors attached to a bridging element for an implant suitable for intravascular delivery, in accordance with aspects of the invention.
Figure 8B:
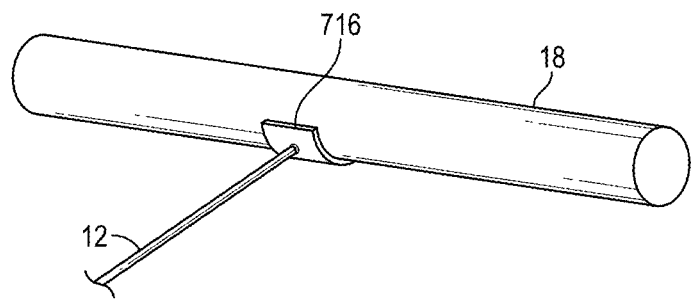
FIG. 8B shows an alternative example of posterior anchors attached to a bridging element for an implant suitable for intravascular delivery, in accordance with aspects of the invention.

FIGS. 8A-8B show alternative methods of connecting the bridging element 12 to a T-shaped posterior anchor. FIG. 8A shows a T-shaped member 18 where the bridging element 12 is wound around a central portion of the T-shaped member. The bridging element 12 may be secured by adhesive 712, knot, or a securing band placed over the bridging element 12, for example. Alternatively, the bridging element 12 may first be threaded through a lumen 714 extending through the T-shaped posterior anchor 18 perpendicular the length of the T-shaped member. The bridging element 12 may then be wound around the T-shaped member, and secured by adhesive 712, securing band, or knot, for example. FIG. 8B shows a T-shaped member 18 where the bridging element 12 is welded or forged to a plate 716. The plate 716 may then be embedded within the T-shaped member 710, or alternatively, secured to the T-shaped member 710 by gluing or welding, for example. It is appreciated that various other couplings could be used to secure the bridging element 12 and posterior anchor 18 and facilitate delivery with the systems and methods described herein.

Figure 9A:
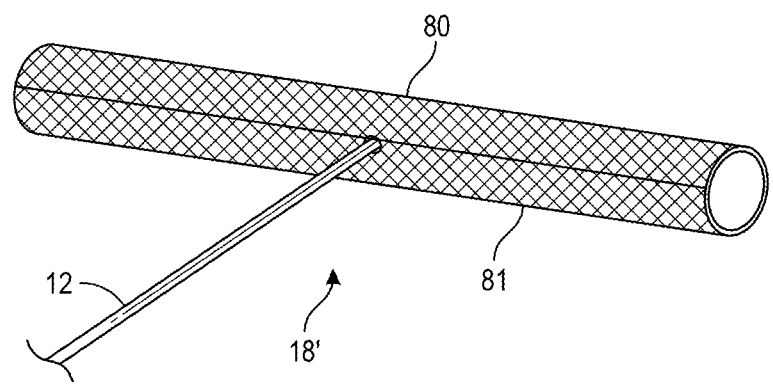
FIG. 9A shows an alternative example of a posterior anchor for a heart implant suitable for intravascular delivery, in accordance with aspects of the invention.
Figure 9B:
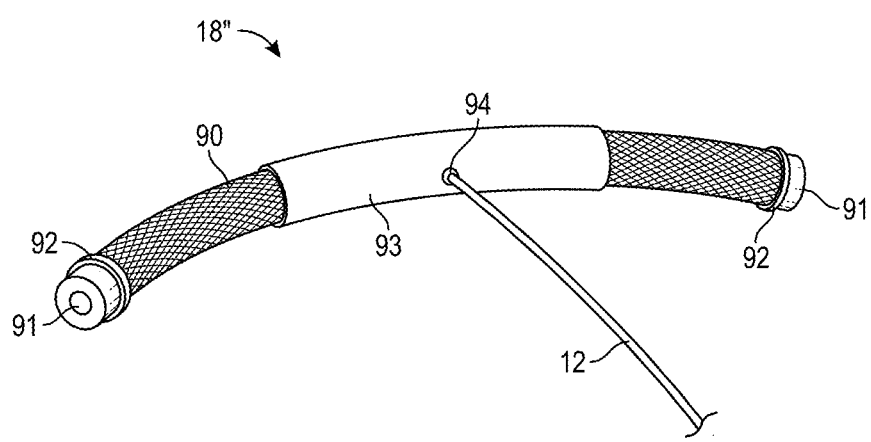
FIG. 9B shows an alternative example of a posterior anchor for a heart implant suitable for intravascular delivery, in accordance with aspects of the invention.

FIGS. 9A-9B depict alternative anchors suitable for use as posterior anchors within a heart implant in accordance with the invention. FIG. 9A is a perspective view of a T-shaped anchor 18' that includes an intravascular stent 80 and, optionally, a reinforcing strut 81. The stent 80 may be a balloon expandable or self-expanding stent. As previously described, the T-shaped anchor 18' is preferably connected to a predetermined length of the bridging element 12. The bridging element 12 may be held within, on, or around the T-shaped bridge stop 80 through the use of any of the bridge locks as previously described, or may be connected to the T-shaped anchor 18 by way of tying, welding, or gluing, for example, or any combination. FIG. 9B depicts a T-shaped anchor 18" that includes a flexible tube 90 having a predetermined length, for example, three to eight centimeters, and an inner diameter 91 sized to allow at least a guidewire to pass through. The tube 90 is preferably braided, but may be solid as well, and may also be coated with a polymer material. Each end of the tube 90 preferably includes a radiopaque marker 92 to aid in locating and positioning the T-shaped anchor. The tube 90 also preferably includes atraumatic ends to protect the vessel walls. The tube may be flexurally curved or preshaped so as to generally conform to the curved shape of the great cardiac vein or interatrial septum and be less traumatic to surrounding tissue. A reinforcing center tube 93 may also be included to add stiffness to the anchor and aids in preventing egress of the anchor from the great cardiac vein and left atrium wall. The bridging element 12 extends through a central hole 94 in an interior side of the reinforcing center tube 93. Each of the anchors described can be straight or curvilinear in shape, or flexile so as to accommodate an anatomy. It is appreciated that various other type of anchors could be used a posterior anchor 18 attached to bridging element 12 for delivery and deployment with the systems and methods described herein.

General Methods of Delivery and Implantation

The implant systems 10 described herein lend themselves to implantation in a heart valve annulus in various ways. Preferably, the implants 10 are implanted using catheter-based technology via a peripheral venous access site, such as in the femoral or jugular vein (via the IVC or SVC) under image guidance, or trans-arterial retrograde approaches to the left atrium through the aorta from the femoral artery also under image guidance. As previously described, the implants 10 comprise independent components that are assembled within the body to form an implant, and delivered and assembled from an exterior to the body through interaction of multiple catheters.

Conventional Delivery Approach

FIGS. 10A-12D show deployment of an implant 10 of the type shown in FIGS. 3A-3B by a percutaneous, catheter-based procedure, under image guidance using conventional methods into the femoral or jugular vein, or typically, a combination of both, such as any of those described in U.S. Patent Application Publication No. 2017/0055969.

Figure 10A:
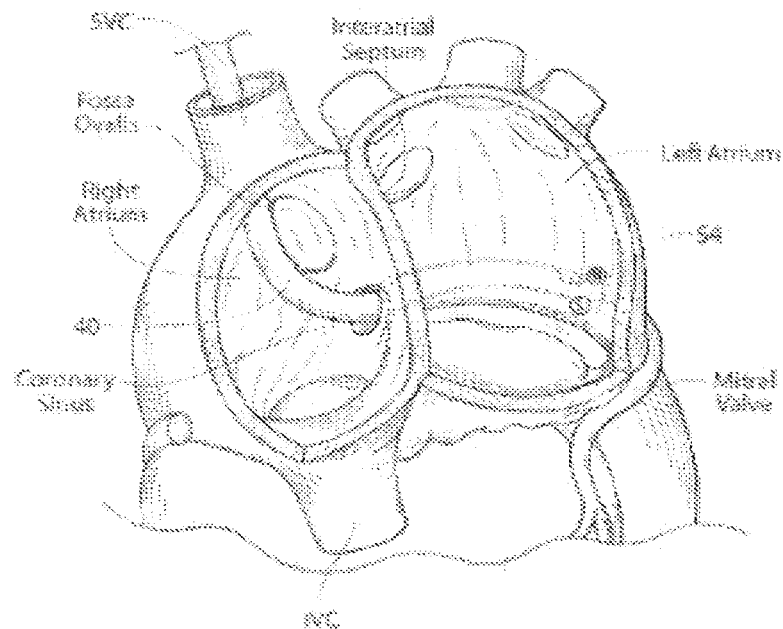
FIG. 10A shows various components and steps of deploying an implant system with a catheter-based delivery system.
Figure 10B:
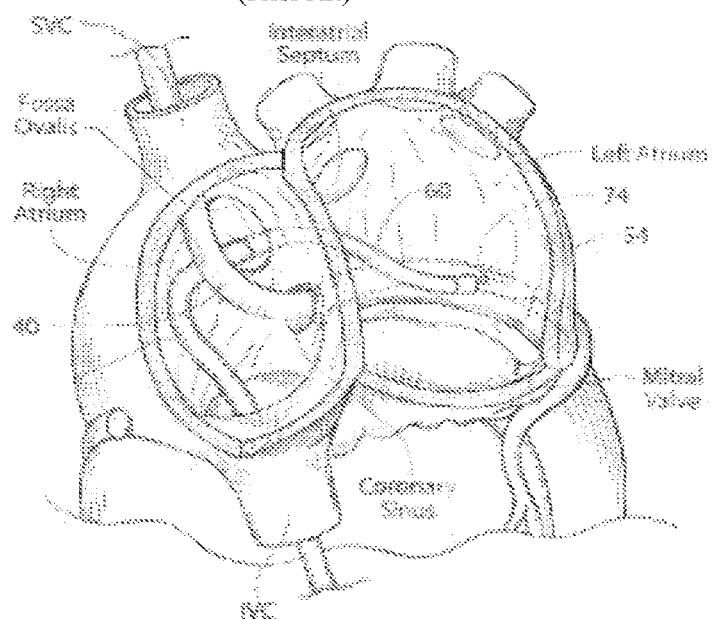
FIG. 10B shows various components and steps of deploying an implant system with a catheter-based delivery system.

Percutaneous vascular access is achieved by conventional methods into the femoral or jugular vein, or typically, a combination of both. As shown in FIG. 10A, under image guidance, a first catheter, or GCV catheter 40, is advanced into the great cardiac vein from a superior vena cava (SVC) route accessed from a neck vein (for example, jugular vein) along a GCV guidewire 54. As shown in FIG. 10B, the LA catheter 60 is advanced from the right atrium via an inferior vena cava (IVC) accessed from a femoral vein, through the septum, typically at or near the fossa ovalis, and into the left atrium. The septal wall at the fossa ovalis is punctured with a trans-septal needle and a LA guidewire 74 is advanced through the septum into the left atrium. Typically a large bore (12-16 French) hemostasis sheath with a "Mullins" shape is placed in the LA to act as a conduit for placement for subsequent devices to placed or removed from the LA without injuring the tissues along the pathway to or in the LA. The LA catheter 60 is then advanced into the left atrium athrough this sheath.

Figure 11A:
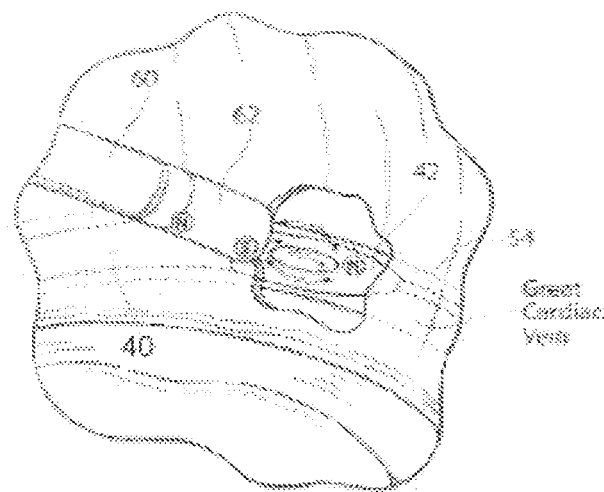
FIG. 11A shows various components and steps of deploying an implant system with a catheter-based delivery system.
Figure 11B:
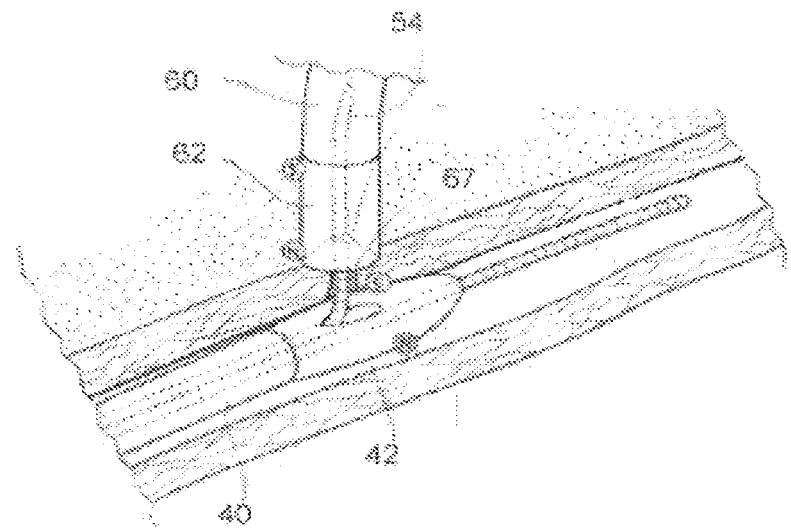
FIG. 11B shows various components and steps of deploying an implant system with a catheter-based delivery system.
Figure 11C:
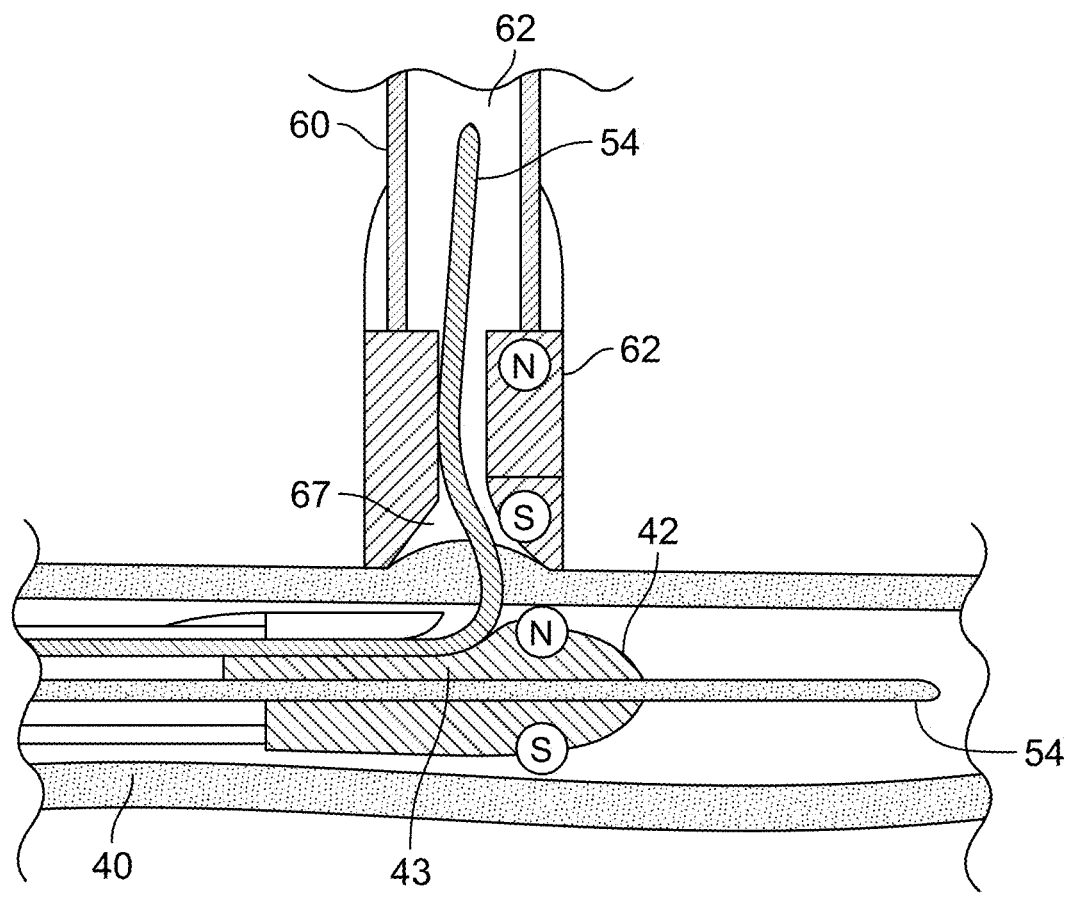
FIG. 11C shows various components and steps of deploying an implant system with a catheter-based delivery system.

Each of catheters 40, 60 include a magnetic head 42, 62, respectively, disposed along a distal portion thereof, the magnetic heads being configured to facilitate magnetic coupling when positioned at a desired orientation and position across a tissue wall between the left atrium and the great cardiac vein. As shown in FIGS. 11A-11B, LA catheter 60 includes distal magnetic head having a N-S magnetic poles arranged axially along the catheter, while the GCV catheter 40 includes distal magnetic head having N-S magnetic poles arranged laterally relative a longitudinal axis of the catheter. This arrangement facilitate a transverse or perpendicular magnetic coupling between the respective catheters, as shown in FIGS. 11B-11C so as to allow passage of a penetrating element or guidewire, typically from a channel within one magnetic head into a corresponding channel of the other magnetic head. In this approach, the penetrating element is a puncturing guidewire 54 with a sharpened distal end. Typically, the puncturing guidewire 54 is advanced through a curved channel 43 within the magnetic head 42 of the GCV catheter 40 and enters a funnel-shaped channel 67 of magnetic head 62 of LA catheter 60. While in this embodiment, the magnetic head of GCV catheter 40 has a single magnet, it is appreciated that various other embodiments can include a magnetic head having additional magnets oriented to facilitate a desired alignment, for example, a three-magnet head in which a center magnet has magnetic poles oriented laterally to an axis of the catheter between two magnets with poles oriented axially, such as that shown in U.S. Patent Application Publication No. 2017/0055969.

Figure 12A:
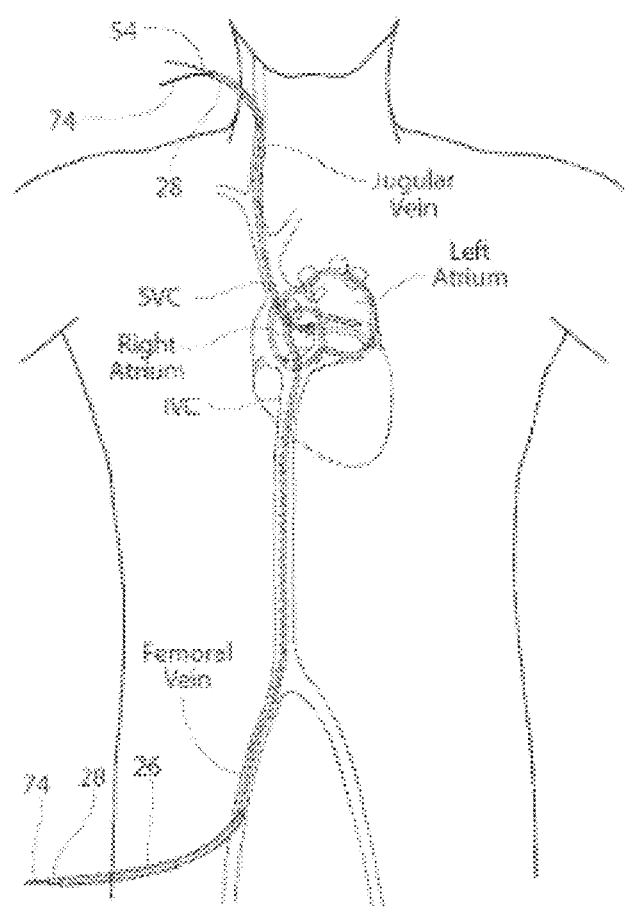
FIG. 12A shows various components and steps of deploying an implant system with a conventional catheter-based delivery system.
Figure 12B:
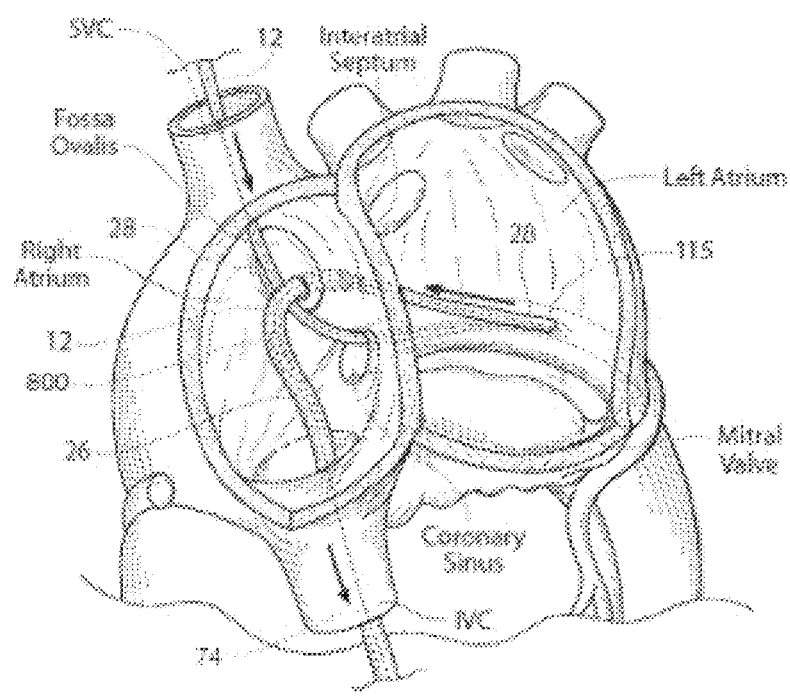
FIG. 12B shows various components and steps of deploying an implant system with a conventional catheter-based delivery system.
Figure 12C:
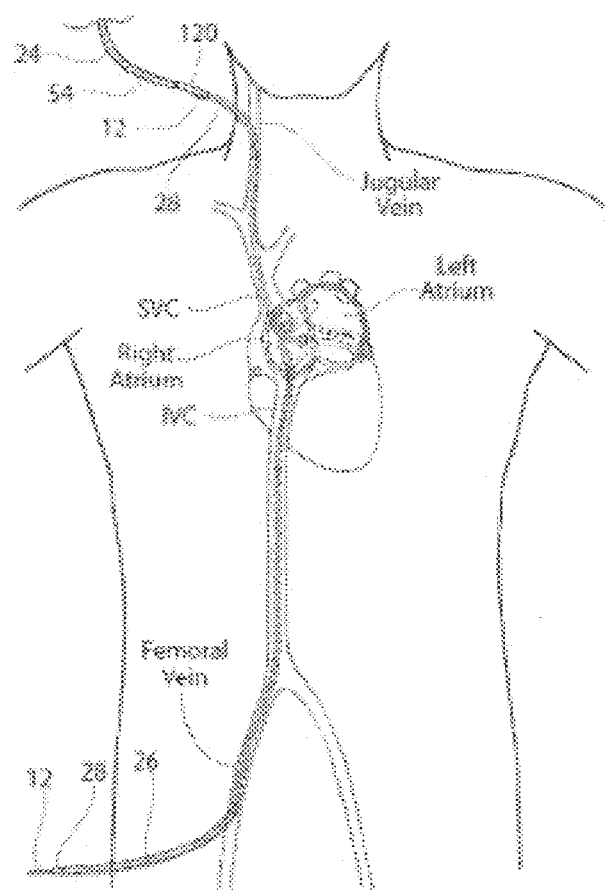
FIG. 12C shows various components and steps of deploying an implant system with a conventional catheter-based delivery system.
Figure 12D:
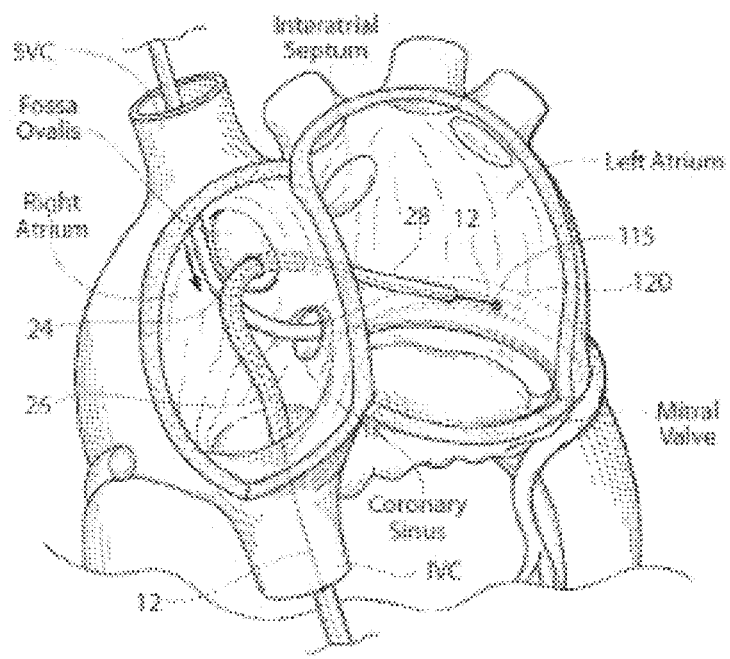
FIG. 12D shows various components and steps of deploying an implant system with a conventional catheter-based delivery system.

Next, as shown in FIG. 12A, the penetrating guidewire is advanced through the LA catheter 60 until it exits the femoral artery access point at the groin. The left atrium magnetic catheter A is then replaced by a very long exchange catheter 28, which is carefully pushed across the puncture site along the great cardiac vein to interface with the great cardiac vein magnetic catheter 40. The exchange catheter 28 is pushed simultaneously with removing the great cardiac vein magnetic catheter 40 to avoid exposing the puncturing wire to tissue. Exposure of the puncturing wire during this process could easily slice through tissue should the wire move or become tensioned during removal or replacement of one of the catheters. This process typically requires two operators, one operator pushes the exchange catheter while the other operator simultaneously removes the great cardiac vein magnetic catheter, often while utilizing visualization techniques to ensure the two catheters remain interfaced and the puncturing wire remains covered. Once the exchange catheter 28 is placed from neck to groin, the puncturing wire is removed and replaced with a left atrial extension guidewire 74, as shown in FIG. 12B.

Next, extension guidewire 74 is gently retracted, causing the bridging element 12 to follow through the vasculature structure. If the optional exchange catheter 28 is used (as shown in FIGS. 12A-12B), the extension guidewire 74 retracts through the lumen of the exchange catheter 28 without injuring tissues. The extension guidewire 74 is completely removed from the body at the femoral vein, leaving the bridging element 12 extending from exterior the body (preferably at the femoral sheath), through the vasculature structure, and again exiting at the superior vena cava sheath. The extension guidewire 74 may then be removed from the bridging element 12 by cutting or detaching the bridging element 12 at or near the interface coupling 800 between the bridging element 12 and extension guidewire 74. The anterior end of the extension guidewire 74 is attached to one end of the bridging element (for example, suture material) while the other end of the bridging element is attached to the posterior anchor, which is retained within a posterior anchor delivery catheter 115. As can be seen in FIG. 12B, the extension guidewire 74 is gently retracted, causing the bridging element 12 to follow into the exchange catheter 28 and through the vasculature structure.

Posterior anchor 120 disposed within deployment catheter 24 is connected to the trailing end of bridging element 12 extending from the superior vena cava. While a T-shaped anchor is shown here, it is appreciated that various other types of posterior anchors can be used (for example, stent, half-stent, and the like). The deployment catheter 24 is then positioned onto or over the GCV guidewire 54 and abutted against exchange catheter 28. The two-operator pushing and pulling process is repeated pushing the posterior anchor delivery catheter 115 while simultaneously removing the exchange catheter 28 so as to position the posterior anchor within the great cardiac vein and the bridging element extends across the left atrium.

Optionally, the bridging element 12 may be pulled from the femoral vein region, either individually, or in combination with the deployment catheter 24, to facilitate advancement of the posterior anchor 120 and bridging element into position in the great cardiac vein and across the left atrium. The GCV guidewire 54 is then retracted letting the T-shaped anchor 120 separate from the GCV guidewire 54 and deployment catheter 24. Preferably under image guidance, and once separation is confirmed, the bridging element 12 is gently pulled to position the T-shaped anchor 120 in abutment against the venous tissue within the great cardiac vein and centered over the GCV access lumen 115. The deployment catheter 24 and exchange catheter 28 may then be removed. The T-shaped anchor 120 with attached bridging element 12 remain within the great cardiac vein. The length of bridging element 12 extends from the posterior T-shaped anchor 120, through the left atrium, through the fossa ovalis, through the vasculature, and preferably remains accessible exterior the body. The bridging element 12 is now ready for the next step of establishing the anterior anchor region 16, as previously described and as shown in FIGS. 16C-16D.

Once the posterior anchor region 14, bridging element 12, and anterior anchor region 16 configured as previously described, a tension is placed on the bridging element 12. The implant 10 and associated regions may be allowed to settle for a predetermined amount of time, for example, five or more seconds. The mitral valve and mitral valve regurgitation are observed for desired therapeutic effects. The tension on the bridging element 12 may be adjusted until a desired result is achieved. The anchor 20 is then secured the bridging element 12 by use of a locking bridge stop 30 when the desired tension or measured length or degree of mitral regurgitation reduction is achieved.

Improved Methods of Delivery and Associated Catheter Systems

In one aspect, an improved anchor delivery catheter allows for delivery and deployment of the above-described implant with fewer catheters and improved ease of use as compared to the conventional approach described above. In some embodiments, the catheter systems includes an anchor delivery catheter having a distal magnet portion that facilitates access to a heart chamber from within an adjacent vasculature by passage of a penetrating guidewire to a magnetically couple catheters within the heart chamber. In some embodiments, the anchor delivery catheter is configured for delivery of the bridging element across the heart chamber (for example, left atrium), once access is achieved, and subsequent deployment of the anchor within the vasculature (for example, great cardiac vein). In some embodiments, the bridging element is attached to a trailing end of the penetrating guidewire while the other end is attached to the posterior anchor disposed on a distal portion of the delivery catheter. This allows the bridging element to be advanced through the penetration between the heart chamber and vasculature by continued advancement of the penetrating guidewire from one vascular access point (for example, jugular vein) to exit the body at the second vascular access point (for example, femoral vein).

In some embodiments, for example, as shown in FIG. 13, the above described anchor delivery is a GCV catheter 50 for delivery of the posterior anchor 18 within the GCV. Catheter 50 preferably includes a magnetic or ferromagnetic head 52 positioned along a distal portion of the catheter shaft. Optionally, a hub can be positioned on the proximal end. The catheter shaft may include a proximal section that is generally stiff to allow for torquability of the shaft, which can be of a solid or braided construction. The proximal section includes a predetermined length (for example, fifty centimeters or more), to allow positioning of the shaft within the vasculature structure. A distal section, along which the distal portion is defined, may be generally flexible to allow for steerability within the vasculature, for example, within the chamber or vasculature of the heart. The distal section can also be of a predetermined length (for example, ten centimeters or more) suitable for maneuvering within the heart. An inner diameter or lumen of the catheter shaft is preferably sized to allow passage of a GCV guidewire 15, and a penetrating guidewire as well as a bridging element. The GCV catheter 50 preferably includes a radiopaque marker to facilitate adjusting the catheter under image guidance to align with the LA catheter 60. The magnetic or ferromagnetic head 52 is preferably polarized to magnetically attract or couple the distal end of the LA catheter 60, as described previously. Magnetic head 52 includes a guide channel formed therein to facilitate passage of the penetrating guidewire through the channel and into a corresponding channel in the magnetic head of the LA catheter 60.

Similar to the GCV catheter 50 the LA catheter 60 preferably includes a magnetic or ferromagnetic head 62 positioned on a distal end thereof. The catheter shaft may include a proximal and distal sections similar to those of catheter 50 described above. The proximal section may be generally stiff to allow for torquability of the shaft, and may be of a solid or braided construction. The distal section includes a predetermined length, for example, ninety centimeters, to allow positioning of the shaft within the vasculature structure. The distal section may be generally flexible and anatomically shaped to allow for steerability through the fossa ovalis and into the left atrium. The distal section may also include a predetermined length, for example, ten centimeters. An inner diameter or lumen of the catheter shaft is preferably sized to allow passage of an LA guidewire 74, and additionally may accept the penetrating guidewire 54 passed from the GCV and subsequently the bridging element 12 attached thereto. The LA catheter 60 may also include a radiopaque marker to facilitate adjusting the catheter 60 under image guidance to align with the GCV catheter 50. The magnetic or ferromagnetic head 62 of the LA catheter 60 is polarized to magnetically attract or couple the distal end of the GCV catheter, for example, as shown in FIGS. 11A-11C. It is appreciated that the magnetic forces in the head 62 may be reversed, as long as attracting magnetic poles in the LA catheter 60 and the GCV catheter 50 are aligned.

While a particular configuration of magnetic heads is described above, it is appreciated that various other magnetic head configurations could be used, for example, of those any of these described in U.S. Patent Application Publication No. 2017/0055969. Detailed examples of such catheter configuration are described further in FIGS. 17-19.

Figure 27:
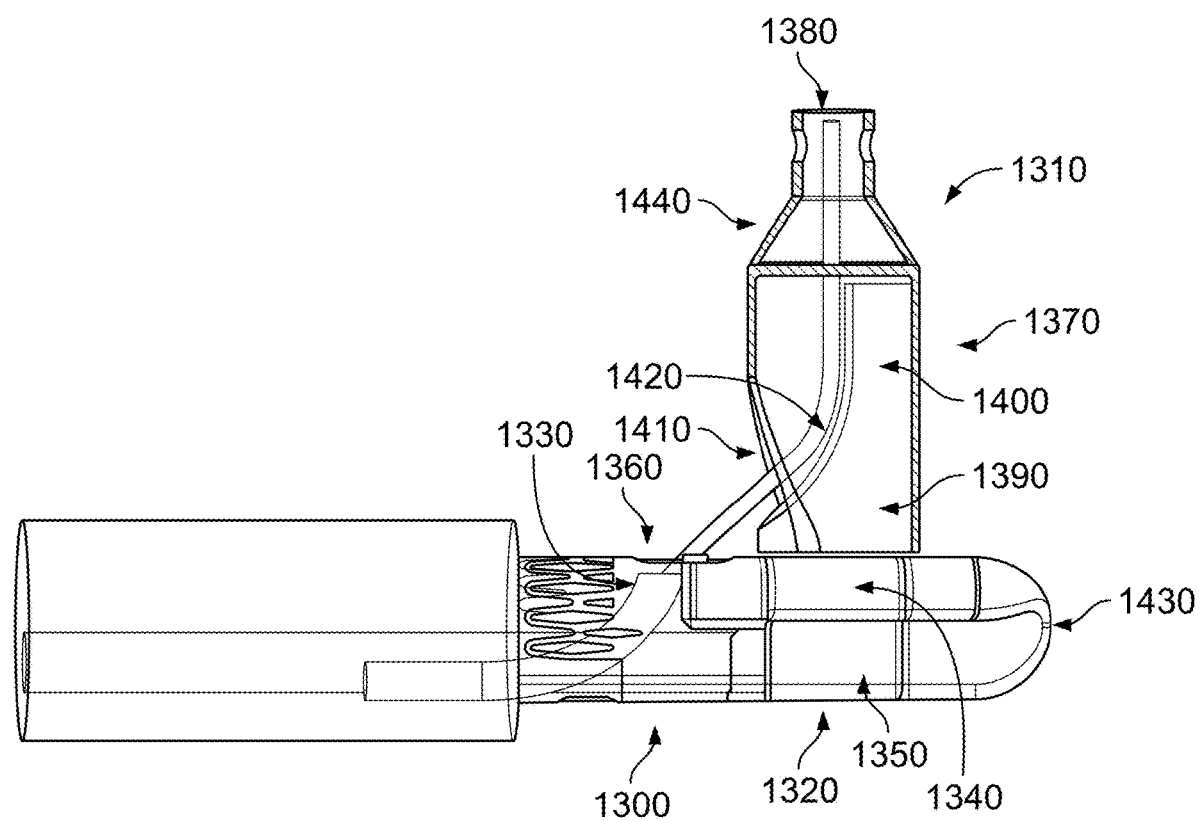
FIG. 27 shows a catheter-based delivery system for deployment of an implant system in which the first and second catheters are magnetically coupled at their respective distal ends, in accordance with aspects of the invention.
Figure 28:
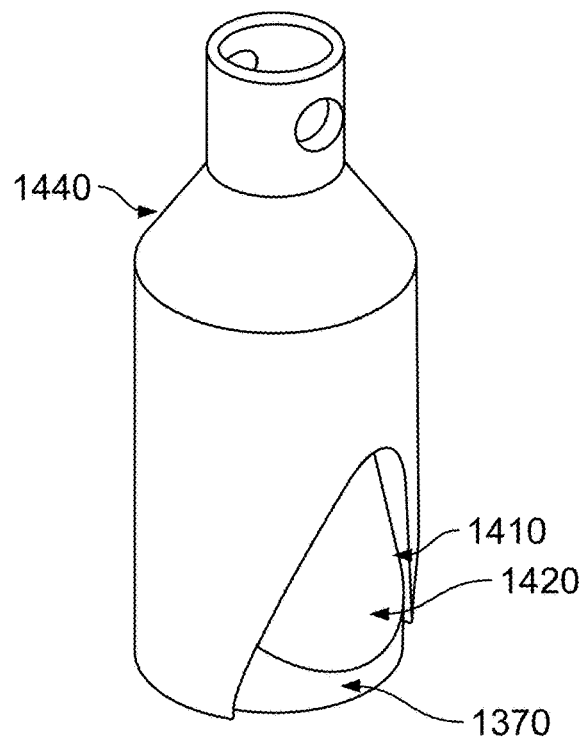
FIG. 28 shows a perspective view of the distal end of a catheter of FIG. 27, in accordance with aspects of the invention.

A system of the invention that includes catheters having another magnet head configuration is shown in FIG. 27. The design reduces the amount of steps the practitioner has to perform to align the magnets of the LA magnet catheter and the GCV catheter and improves visualization of the penetrating guidewire and catheter alignment during crossing of the wall of the left atrium.

With reference to FIG. 27, the system includes first and second magnetic catheters. FIG. 27 illustrates the distal regions of the first and second magnetic catheters and shows the magnet arrangement within their respective magnetic heads. The first catheter 1300, for advancement into the GVC, has a proximal end and a distal end (distal end shown in FIG. 27) and includes a first lumen extending through a length of the first catheter, a first magnet 1320 disposed along a distal portion of the first catheter, and a first guide channel 1330 disposed in the distal portion of the first catheter and extending along a first longitudinal axis. In various aspects, the first magnet 1320 includes a first magnetic pole 1340 and a second magnetic pole 1350. Additionally, the first guide channel 1330 is coextensive with the first lumen and has a first side hole 1360 located proximal along the distal portion of the first catheter relative to the first magnetic pole 1340.

The second catheter 1310, for advancement into the LA, has a proximal end and a distal end (distal end shown in FIG. 27) and includes a second lumen extending through the length of the second catheter, a second magnet 1370 disposed at the distal end of the second catheter, and a second guide channel 1380 disposed at the distal end of the second catheter and extending along a second longitudinal axis. In various aspects, the second magnet 1370 includes a third magnetic pole 1390 and a fourth magnetic pole 1400. Additionally, the second guide channel is coextensive with the second lumen and has a second side hole 1410 adjacent the second magnet 1370.

The first magnet 1320 and the second magnet 1370 are configured such that they automatically align the distal portions of the first catheter 1300 and the second catheter 1310 and magnetically couple with the distal portions of the first and second catheters being substantially perpendicular to one another (approximately 90 degrees with respect to one another) upon coupling (as shown in FIG. 27). As such, the first magnetic pole 1340 and the third magnetic pole 1390 are of opposite polarity and proximate each other upon magnetic coupling. For example, the first magnetic pole 1340 is of positive polarity and the third magnetic pole 1390 is of negative polarity. In this configuration, the first magnetic pole 1340 and the second magnetic pole 1350 are disposed perpendicular with respect to a longitudinal axis of the first guide channel 1330 and the third magnetic pole 1390 and the fourth magnetic pole 1400 are disposed parallel with respect to a longitudinal axis of the second guide channel 1380 with the third magnetic pole 1390 being distal to the fourth magnetic pole 1400 along the distal end of the second catheter 1310. It is appreciated that the magnetic forces in first magnet 1320 and the second magnet 1370 may be reversed, as long as attracting magnetic poles in the first catheter 1300 and the second catheter 1310 are aligned.

Figure 29:
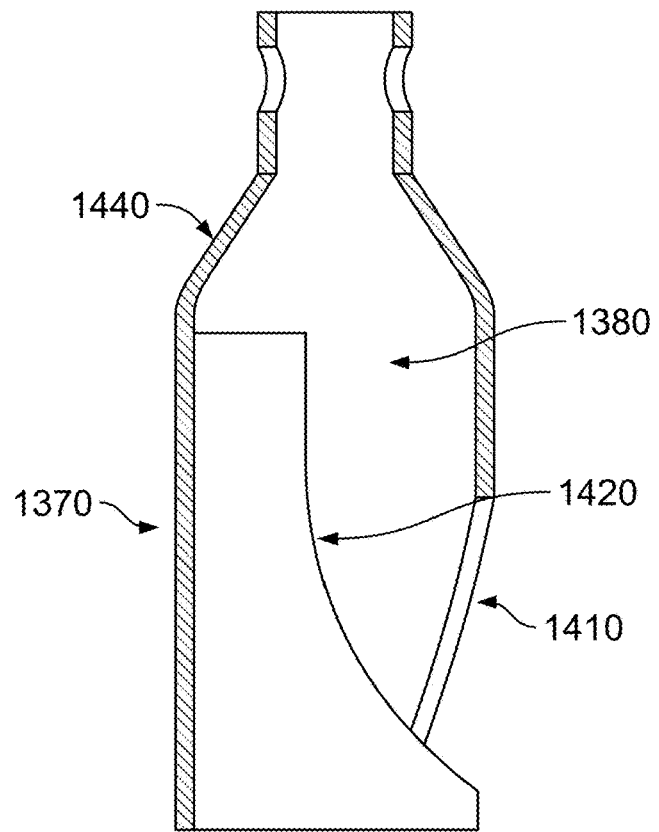
FIG. 29 shows cross-sectional view of the distal end of the catheter of FIG. 28, in accordance with aspects of the invention.

Upon magnetic coupling of the first magnet 1320 and the second magnet 1370, the first side hole 1360 and the second side hole 1410 are aligned in a plane parallel to a longitudinal axis of the first guide channel 1330 and a second longitudinal axis of the second guide channel 1380 such that an advancing crossing wire may traverse through the first guide channel 1330 and exit the first side hole 1360 and enter the second side hole 1410 and traverse the second guide channel 1380. Additionally, upon magnetic coupling, the second side hole 1410 is oriented distal along the distal portion of the first catheter relative to the first side hole 1360 as shown in FIG. 29. In this configuration the first side hole 1360 and the second side hole 1410 are substantially perpendicular with respect to one another.

As illustrated in FIGS. 27 and 29, to facilitate passage of a crossing wire from the first guide channel 1330 and through the second guide channel 1380, the second magnet 1370 includes a contoured recess having an arcuate or sloped surface 1420 oriented towards the second guide channel 1380 and defining a surface of the second guide channel 1380. In various aspects, the arcuate or sloped surface 1420 extends from a distal portion of the second magnet 1370 to a proximal portion of the second magnet.

It will be appreciated that this configuration works by allowing the magnet catheters to attach at a 90 degree angle. The magnet shape helps the penetrating guidewire to turn into the LA catheter shaft which is attached to 1380. The magnet polarity is defined such that the LA catheter magnet and the magnet 1320 of the GCV catheter will always attach as shown in FIG. 27.

In some aspects, one or more magnets of the catheters are coated in a smooth gold coating to reduce friction during crossing. In some aspects, the second magnet 1370 is coated with a friction reducing material, such as gold, to reduce friction during crossing.

In addition, in some aspects, the steering tube is designed and located so that the penetrating guidewire approaches magnet 1370 of the LA catheter at an angle to reduce the amount of friction in the system. Further, as discussed, the magnet 1370 has internal geometry to help guide the penetrating guidewire into the LA catheter shaft.

Figure 22A:
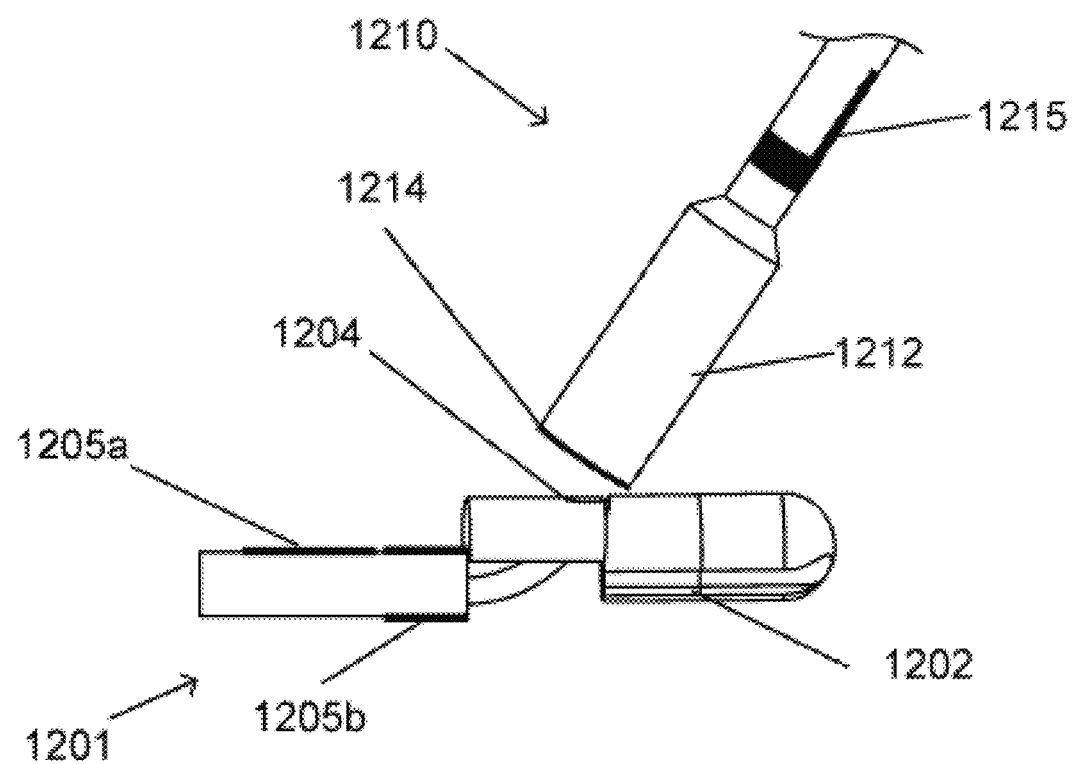
FIG. 22A depicts exemplary radiopaque markers to facilitate rotational alignment between the delivery catheters of the system, in accordance with aspects of the invention.

To facilitate visualization of the catheters during advancement and magnetic coupling, the first catheter 1300 and/or the second catheter 1310 may include one or more radiopaque markers disposed at their respective distal ends. As shown in FIG. 27, the first catheter 1300 includes a terminally disposed radiopaque marker 1430. The second catheter 1310 may also include a terminally disposed radiopaque marker. In some aspects, the distal portion of the second catheter 1310 includes a magnet housing 1440 which is constructed of a material that is translucent under fluoroscopy thereby allowing the crossing wire to be viewed and/or tracked during the crossing procedure. The first and second catheters may also include additional radiopaque markers as shown in FIG. 22A.

Figure 30:
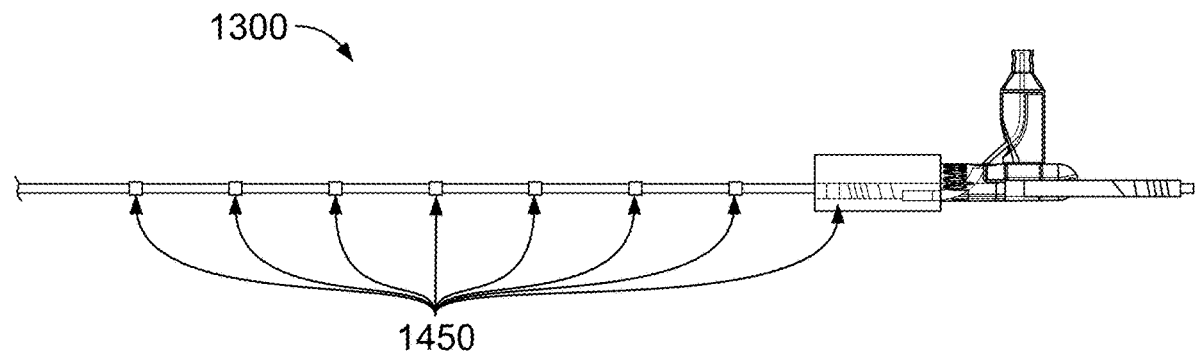
FIG. 30 shows a catheter of a catheter-based delivery system for deployment of an implant system in which the catheter includes radiopaque markers disposed along the length of the catheter for determining insertion depth, in accordance with aspects of the invention.

Additionally, in some aspects, the first and/or second catheter may include one or more radiopaque markers disposed along their respective lengths. For example, the first and/or second catheter may include a series of radiopaque markers disposed along their respective lengths at spaced intervals to allow the user to determine the depth of insertion of the respective catheter within the vasculature or bodily cavity. FIG. 30 illustrates the first catheter 1300 having a series of radiopaque markers 1450 disposed along the length of the catheter.

Further, in some aspects, the penetrating guidewire includes a nitinol wire with a Platinum/Iridium (PTIR) core to enhance the imaging of the wire and improve the practitioner's ability to see the wire at all times during a procedure.

Implantation Methods

Access to the vascular system is commonly provided through the use of introducers known in the art. A 16F or less hemostasis introducer sheath (not shown), for example, may be first positioned in the superior vena cava (SVC), providing access for the GCV catheter 50. Alternatively, the introducer may be positioned in the subclavian vein. A second 14F or less introducer sheath (not shown and described above) may then be positioned in the right femoral vein, providing access for the LA catheter 60. Access at both the SVC and the right femoral vein, for example, also allows the implantation methods to utilize a loop guidewire. For instance, in a procedure to be described later, a loop guidewire is generated by advancing a LA guidewire through the vasculature until it exits the body and extends external the body at both the superior vena cava sheath and femoral sheath. The LA guidewire may follow an intravascular path that extends at least from the superior vena cava sheath through the interatrial septum into the left atrium and from the left atrium through atrial tissue and through a great cardiac vein to the femoral sheath.

Figure 14A:
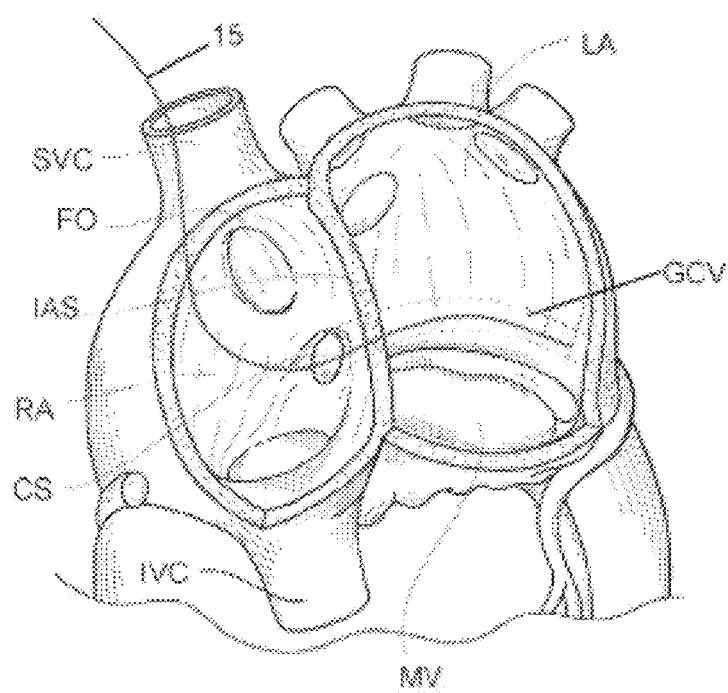
FIG. 14A illustrates a step of delivery and deployment of the implant system for treatment of mitral valve regurgitation, in accordance with aspects of the invention.

FIGS. 14A-16D illustrate a method of implantation utilizing a magnetic anchor delivery catheter in accordance with aspects of the invention. FIGS. 14A-14B depict positioning of the GCV anchor delivery catheter 50 within the great cardiac vein adjacent a posterior annulus of the mitral valve. First, as shown in FIG. 14A, under image guidance, the GCV guidewire 15 (for example, a 0.035 inch guidewire) for example, is advanced into the coronary sinus to the great cardiac vein along an SVC approach. Optionally, an injection of contrast with an angiographic catheter may be made into the left main artery from the aorta and an image taken of the left coronary system to evaluate the position of vital coronary arterial structures. An injection of contrast may also be made in the great cardiac vein in order to provide an image and a measurement. If the great cardiac vein is too small, the great cardiac vein may be dilated with a 5 to 12 millimeter balloon, for example, to midway the posterior leaflet.

Figure 14B:
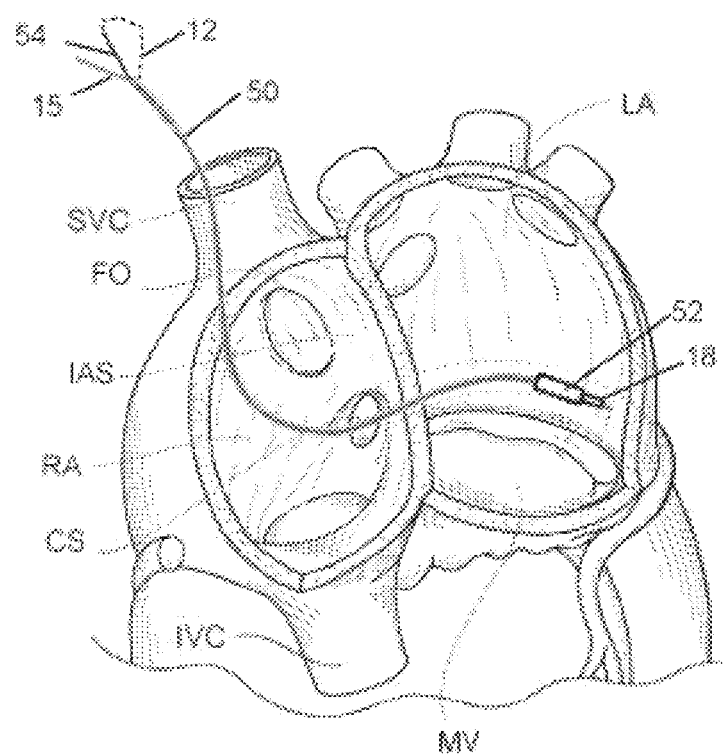
FIG. 14B illustrates a step of delivery and deployment of the implant system for treatment of mitral valve regurgitation, in accordance with aspects of the invention.

As shown in FIG. 14B, the GCV catheter 50 is advanced over the GCV guidewire 15 so that the distal magnetic head 52 and posterior anchor 18 are positioned at or near a desired location in the great cardiac vein, for example, near the center of the posterior leaflet or posterior mitral valve annulus. The desired position for the GCV catheter 50 may also be viewed as approximately 2 to 6 centimeters from the anterior intraventricular vein takeoff. Once the GCV catheter 50 is positioned, an injection may be made to confirm sufficient blood flow around the GCV catheter 50. If blood flow is low or non-existent, the GCV catheter 50 may be pulled back into the coronary sinus until needed.

Figure 14C:
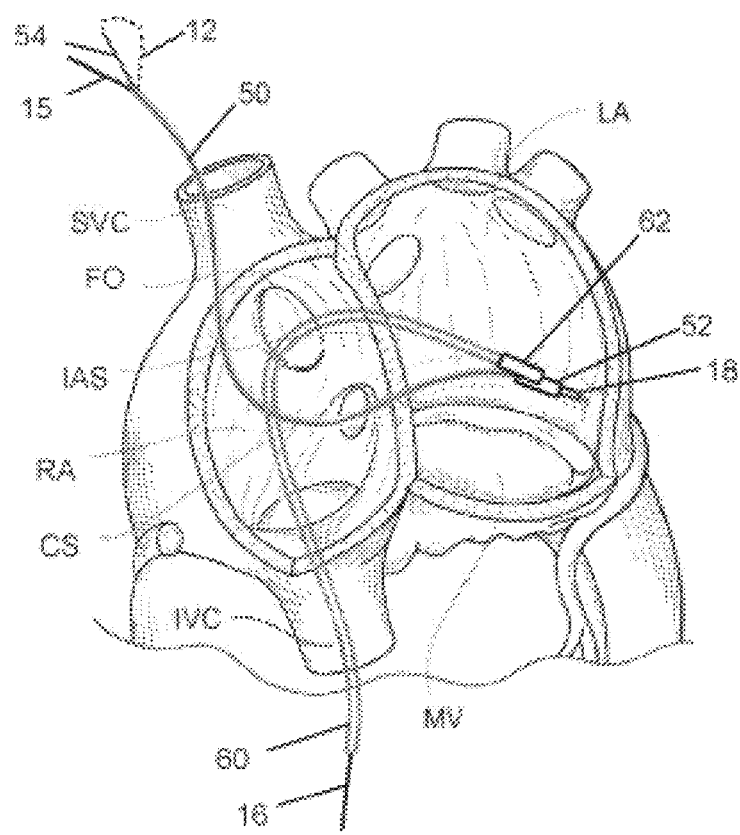
FIG. 14C illustrates a step of delivery and deployment of the implant system for treatment of mitral valve regurgitation, in accordance with aspects of the invention.

As shown in FIG. 14C, the LA catheter 60 is then deployed in the left atrium. From the femoral vein, under image guidance, the LA guidewire 16, a 0.035 inch guidewire for example, is advanced into the right atrium. A 7 Fr Mullins dilator with a trans-septal needle (not shown) can be deployed into the right atrium. An injection is made within the right atrium to locate the fossa ovalis on the septal wall. The septal wall at the fossa ovalis can be punctured with a trans-septal needle and the guidewire 16 is advanced into the left atrium. The trans-septal needle is then removed and the dilator is advanced into the left atrium. An injection is made to confirm position relative to the left ventricle. The Mullins system is removed and then replaced with a 12 Fr or other appropriately sized Mullins system. The 12 Fr Mullins system is positioned within the right atrium and extends a short distance into the left atrium and the LA catheter 60 is advanced into the left atrium. After advancement of the LA catheter 60 into the left atrium, a distal magnetic head 62 of the catheter is positioned in the region adjacent the great cardiac vein so as to magnetically couple with the magnetic head 52 of GCV magnetic catheter 50, for example, as shown in FIGS. 11A-11C, the magnetic heads automatically align the lumens of the LA catheter 60) and GCV catheter 50. Similarly, after advancement of the second magnetic catheter 1310 into the left atrium, a distal magnet 1370 of the catheter is positioned in the region adjacent the great cardiac vein so as to magnetically couple with the magnet 1320 of first magnetic catheter 1300, for example, as shown in FIG. 27. The magnets automatically align the lumens of the second LA catheter 1310 and first GCV catheter 1300. It will be appreciated that in various aspects, any methodology of the invention may employ any appropriately sized sheath system, such as 12 Fr, 14 Fr, and the like. In one aspect, a 14 Fr sheath system is used.

Figure 14D:
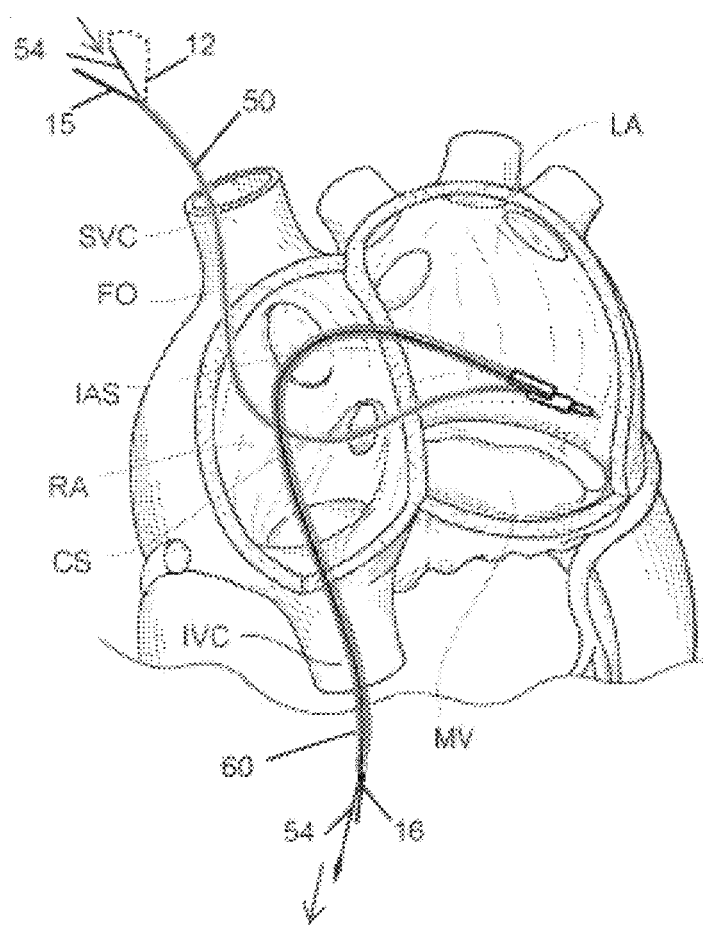
FIG. 14D illustrates a step of delivery and deployment of the implant system for treatment of mitral valve regurgitation, in accordance with aspects of the invention.

As shown in FIG. 14D, once magnetically coupled, puncturing guidewire 54 is advanced through GCV catheter 50 to penetrate the tissue wall between the great cardiac vein and the left atrium and enters a lumen of the magnetic head 62 of LA catheter 60. The operator continues to advance the puncturing guidewire 54 through a lumen of the LA catheter 60 until the guidewire exits the body (for example, at the groin). Since the trailing end of the puncturing guidewire is attached to the one end of the bridging element 12 (for example, suture), the other end of the bridging wire being attached to posterior anchor 18, once the puncturing guidewire 54 exits the proximal end of the LA catheter 60, the puncturing wire 54 can be pulled proximally from the LA catheter 60 thereby pulling the bridging element 12 through the GVC catheter 50, across the left atrium within the LA catheter 60 and through the vasculature to exit the body at the groin, all while the LA catheter 60 and the GVC catheter 50 remain magnetically coupled. This approach ensures the puncturing wire 54 and the bridging element 12 remain covered while the being drawn through the vasculature over the delicate tissues of the heart. This avoids cutting or slicing the tissue with the bridging element when pulled across the tissues and further avoids the laborious pushing and pulling procedure and use of an exchange catheter described in the conventional approach.

Figure 15A:
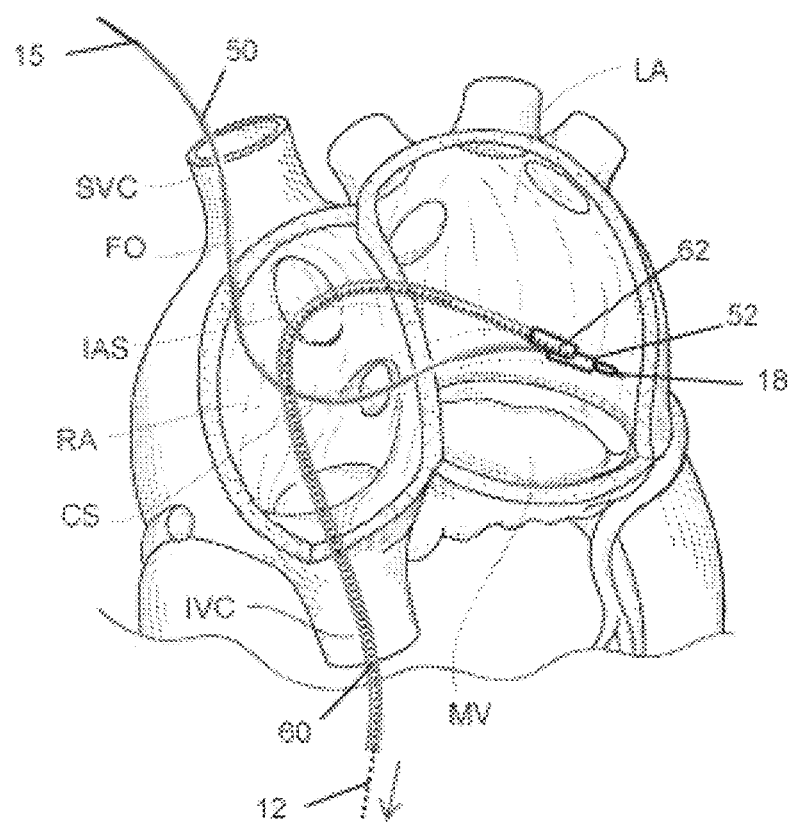
FIG. 15A illustrates a step of delivery and deployment of the implant system for treatment of mitral valve regurgitation, in accordance with aspects of the invention.
Figure 15B:
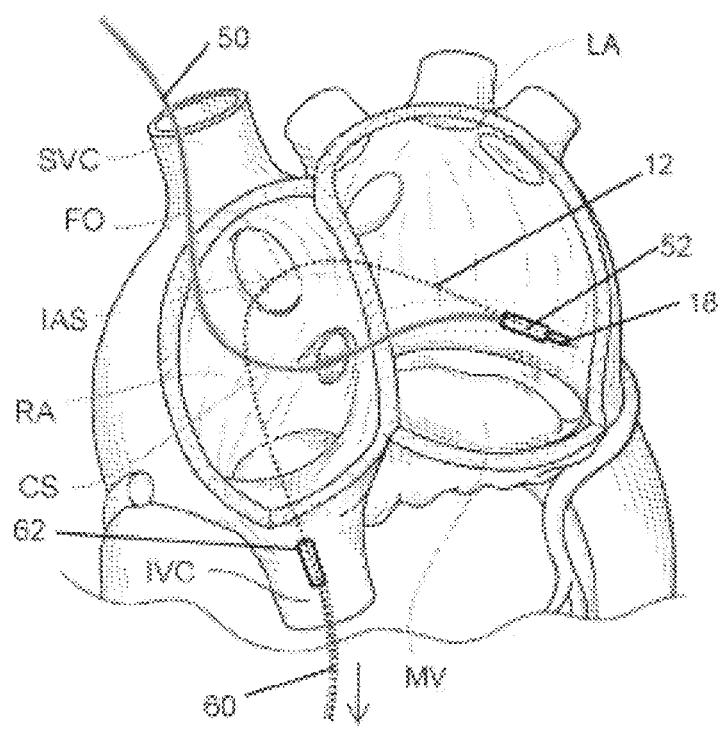
FIG. 15B illustrates a step of delivery and deployment of the implant system for treatment of mitral valve regurgitation, in accordance with aspects of the invention.

As shown in FIG. 15A, the bridging element 12 extends from the posterior anchor 18 disposed within the distal portion of the GCV catheter 50, spans the left atrium and extends through the LA catheter 60 and exits the body at the femoral vein. The operator can gently tug the bridging element 12 to remove any slack from the system and ensure it is properly positioned. In some embodiments, this action can also facilitate release of the posterior anchor 18 from the GCV delivery catheter 50. The LA catheter 60 can be decoupled from the GCV catheter 50 and withdrawn while the bridging element remains in place, as shown in FIG. 15B. Optionally, the LA catheter 60 can remain within the left atrium extending through the septum until the posterior anchor 18 is fully deployed.

Figure 15C:
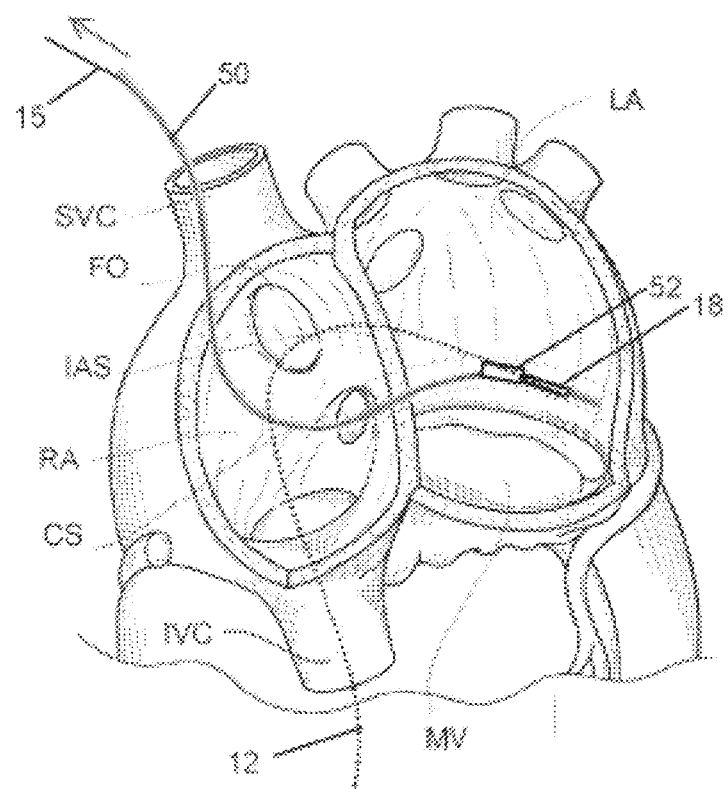
FIG. 15C illustrates a step of delivery and deployment of the implant system for treatment of mitral valve regurgitation, in accordance with aspects of the invention.

As shown in FIG. 15C, the GCV catheter 50 is adjusted, if needed, to position the posterior anchor 18 along the penetration for subsequent release from the catheter. The posterior anchor 18 can be released from the GCV delivery catheter 50 by proximally retracting the GCV guidewire 15 extending through the posterior anchor 18. Optionally, the catheter configuration can include a releasable coupling feature, such as a tether 903, that secures the posterior anchor 18 to the distal portion of GCV catheter 50 and extends from the proximally end so that an operator can proximally pull the tether to release the posterior anchor 18. The tether can be defined as a wire or suture that frictionally engages the posterior anchor in place at one end and extends proximally from the catheter at the other end, or as a tether loop that wraps around the posterior anchor and interfaces with a feature along the distal portion of the GCV catheter and both ends extend proximally from the catheter such that pulling the tether releases. It is appreciated that various types of releasable couplings could be used including any of those described in U.S. Patent Application Publication Nos. 20070265658 and 20120016456, incorporated herein by reference in their entireties.

Figure 15D:
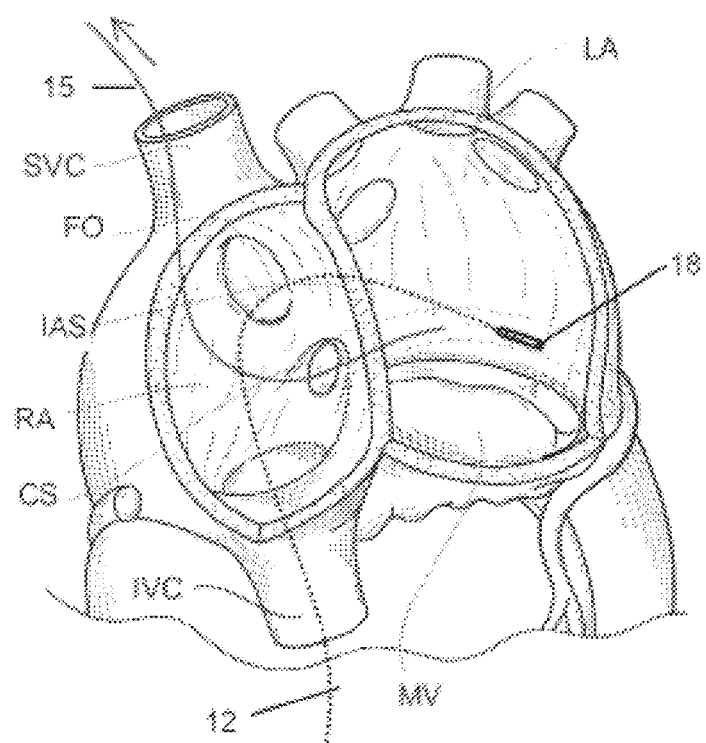
FIG. 15D illustrates a step of delivery and deployment of the implant system for treatment of mitral valve regurgitation, in accordance with aspects of the invention.

During the process, the GCV catheter 50 can be retracted slightly, particularly in embodiments where the posterior anchor 18 partly resides in a recessed portion of the magnetic head 52. In many cases of complete or partial removal of the GCV catheter, the guidewire is left inside the GCV anchor to allow for retrieval until very end of the procedure. While in this embodiment, the posterior anchor 18 is an elongate member, such as a T-bar anchor, it is appreciated that various other deployment steps could be used to facilitate deployment of other types of posterior anchors. For example, when the posterior anchor 18 is a scaffold or stent-like structure, any suitable means of deploying such structures could be used. For example, a constraining sheath partly disposed over a self-expanding scaffold can be retracted thereby releasing the scaffold from the magnetic head portion 52 or a balloon expandable scaffold, or otherwise releasable scaffold can be used. Once the posterior anchor 18 is deployed, the GCV catheter 50 and GCV guidewire can be removed, as shown in FIG. 15D.

Figure 5B:
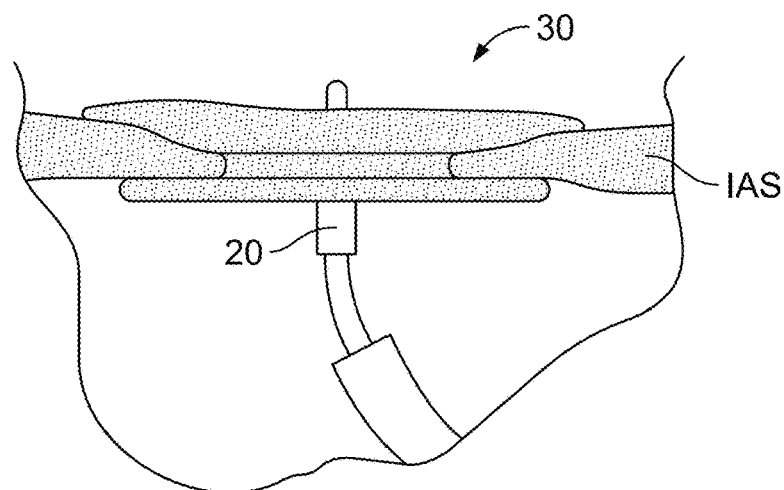
FIG. 5B shows a detailed view of an example anterior anchor of the implant that is suitable for anchoring within the patent fossa ovalis of the inter-atrial septum.
Figure 16A:
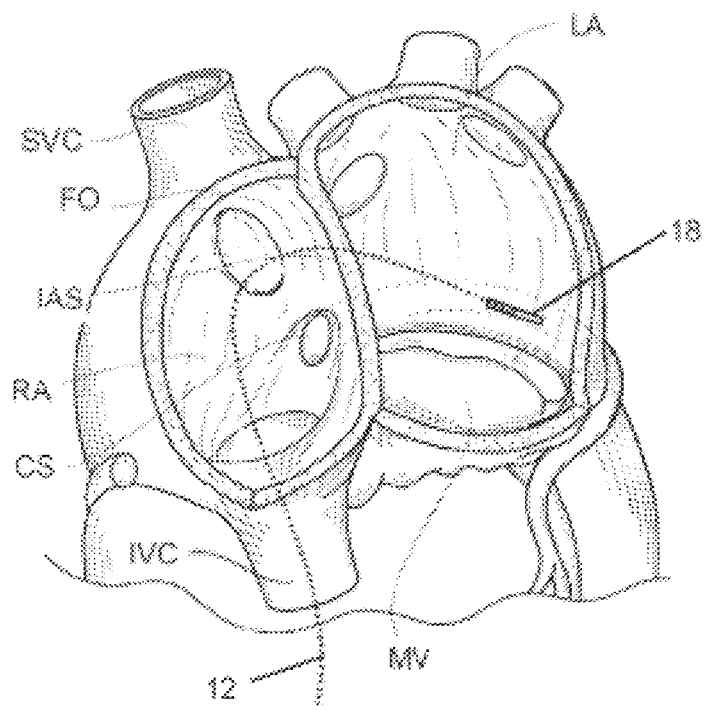
FIG. 16A illustrates a step of delivery and deployment of the implant system for treatment of mitral valve regurgitation, in accordance with aspects of the invention.
Figure 16B:
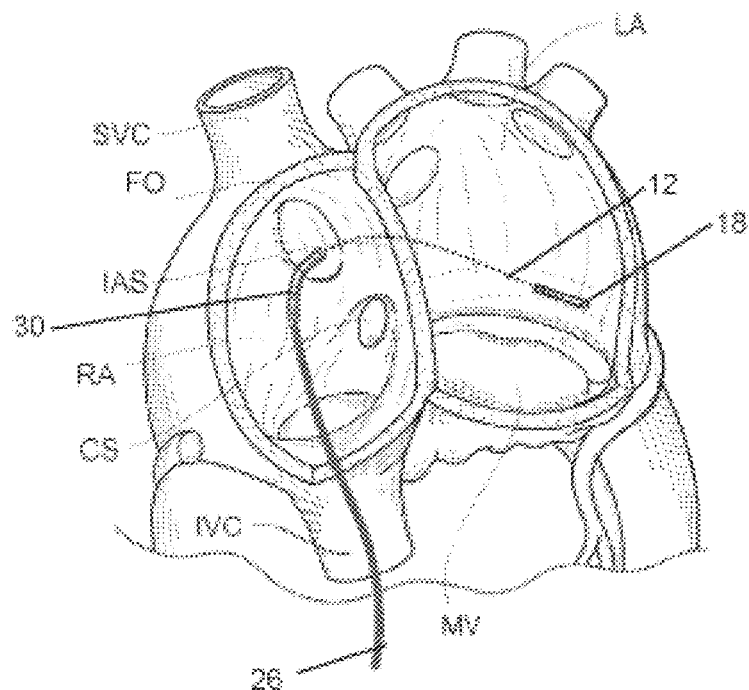
FIG. 16B illustrates a step of delivery and deployment of the implant system for treatment of mitral valve regurgitation, in accordance with aspects of the invention.
Figure 16C:
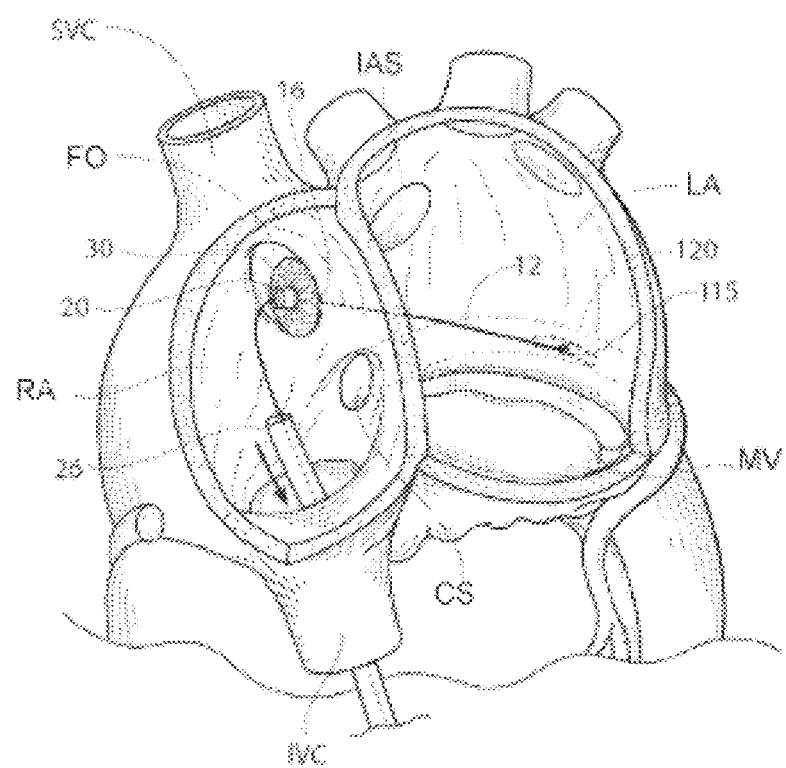
FIG. 16C illustrates a step of delivery and deployment of the implant system for treatment of mitral valve regurgitation, in accordance with aspects of the invention.
Figure 16D:
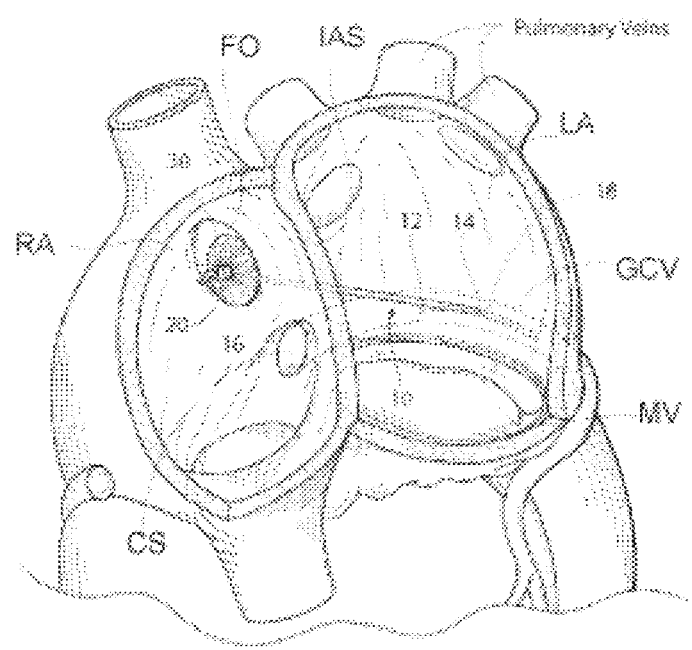
FIG. 16D illustrates a step of delivery and deployment of the implant system for treatment of mitral valve regurgitation, in accordance with aspects of the invention.

As shown in FIG. 16A, the posterior anchor 18 deployed within the great cardiac vein is attached to the bridging element 12 spanning the left atrium and extending through the vasculature along the IVC route to exit from the femoral vein at the groin. Since the bridging element 12 is not yet tensioned, there is little likelihood of cutting or damage to tissues at this point. Next, as shown in FIG. 16B, an anterior anchor delivery catheter 26 is advanced along the bridging element 12 with the anterior anchor mounted with the bridging element passing through its central hub the delivery catheter 26 having an anterior anchor 30, collapsed inside the delivery sheath, disposed in a distal portion thereof, the bridging element passing through its central hub. The collapsed anterior anchor is guided to the FO or other suitable location along the septal wall and deployed, such as shown in FIG. 5B.

As shown in FIG. 16C, the anterior anchor 30 is deployed along the septal wall with a proximal locking bridge stop 20 through the delivery sheath. The length of the bridging element 12 can then be incrementally adjusted and held in place by the bridge lock 20) upon each adjustment until observation of the heart pumping indicates improved valve function. The excess bridging element 12 can then be cut with a cutting element of the catheter, or by use of a separate cutting catheter advanced along the bridging element 12. The LA delivery catheter 60 can then be removed, leaving the fully deployed implant 10 in place within the heart, as shown in FIG. 16D.

In similar embodiments, the invention provides a method of performing a surgical procedure on a subject using the system of the invention as shown in FIG. 27. The method includes inserting, through a first vascular access site, the first catheter 1300, and advancing the first catheter 1300 to a first location in or proximate a heart of the subject. The second catheter 1310 is inserted through a second vascular access site and advanced to a second location in or proximate the heart, the first and second locations being separated by a tissue wall of the heart. The first catheter 1300 and the second catheter 1310 are positioned such that the first magnet 1320 and the second magnet 1370 magnetically couple across the tissue wall. The tissue wall is then penetrated with a penetrating member, such as a penetrating guidewire which is advanced through the first catheter 1300, across the tissue wall and through the second catheter 1310 while the first and second catheters are magnetically coupled. In some aspects, the method further includes determining the depth of insertion of the first and/or second catheter via radiopaque markers disposed along the respective lengths of the catheters (shown in FIG. 30) before magnetic coupling of the first magnet 1320 and the second magnet 1370. The method further includes advancing a posterior anchor and a bridging element coupled at a first end of the bridging element to the posterior anchor to the first location from the first vascular access site while the first magnet and second magnet are magnetically coupled, advancing a second end of the bridging element through the penetrated tissue wall and into the second catheter, and advancing an anterior anchor along the bridging element from the second vascular access site and deploying the anterior anchor at a third location in the heart, the bridging element spanning across a chamber of the heart as shown in FIGS. 16A-16D.

Figure 36:
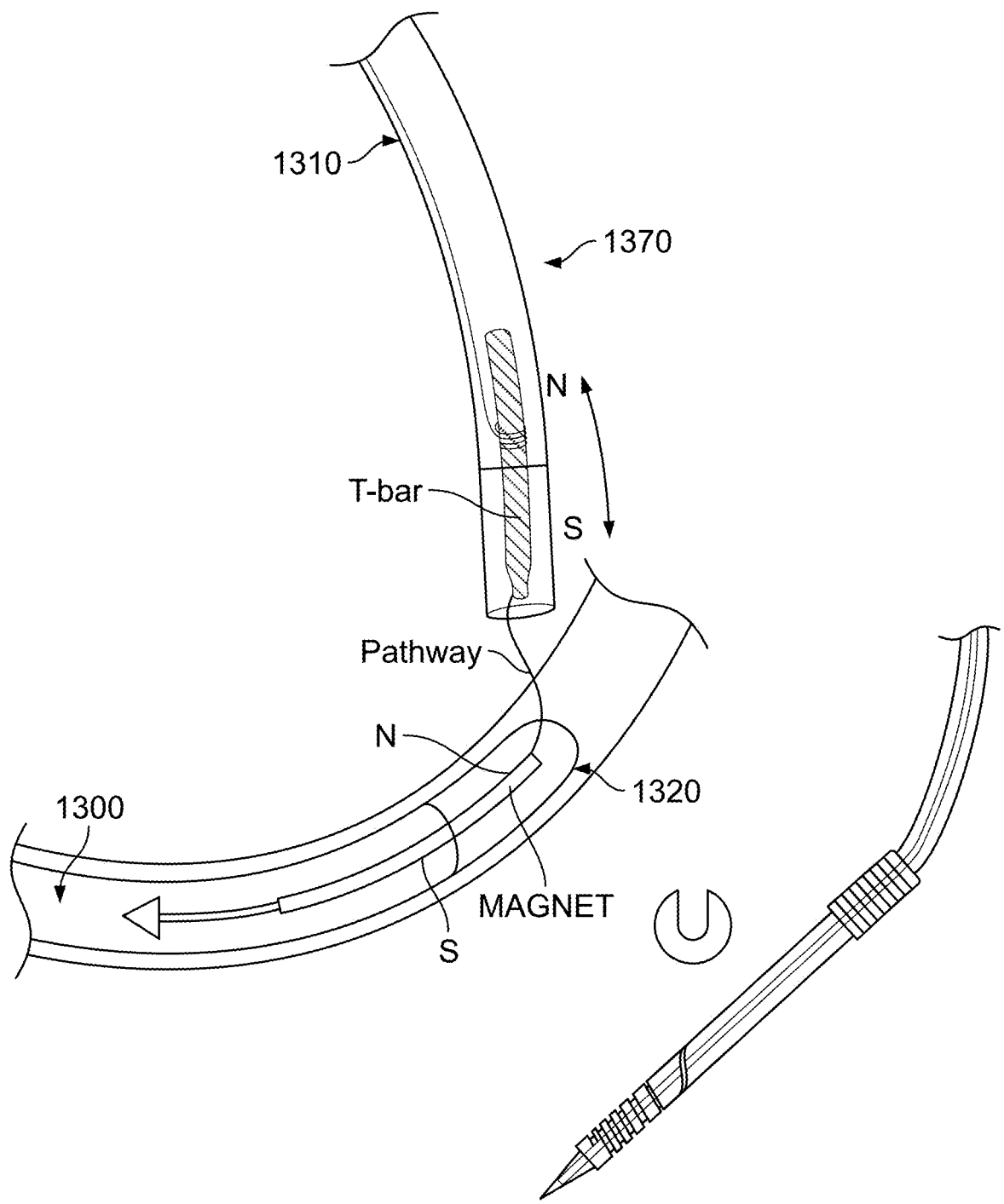
FIG. 36 shows the magnetic catheter system of the invention being used to advance the penetrating member, e.g., the crossing wire, from the left atrium into the GCV.

FIG. 36 illustrates use of the catheter system of the invention to advance the posterior anchor into the GCV via the left atrium. As shown in FIG. 36, as well as in FIGS. 37-45, in some aspects, the posterior anchor is delivered from the left atrium into the GCV. The GCV catheter, e.g., the first catheter, while inside the GCV, is hollowed out with a hollow open section facing toward the left atrium (concave toward left atrium). The posterior anchor is guided down the LA catheter, e.g., the second catheter, and crosses the tissue and is deposited into a trough of GCV catheter. A crossing wire is needed beforehand to facilitate tracking of the posterior anchor through the crossing hole in the LA wall.

Figure 37:
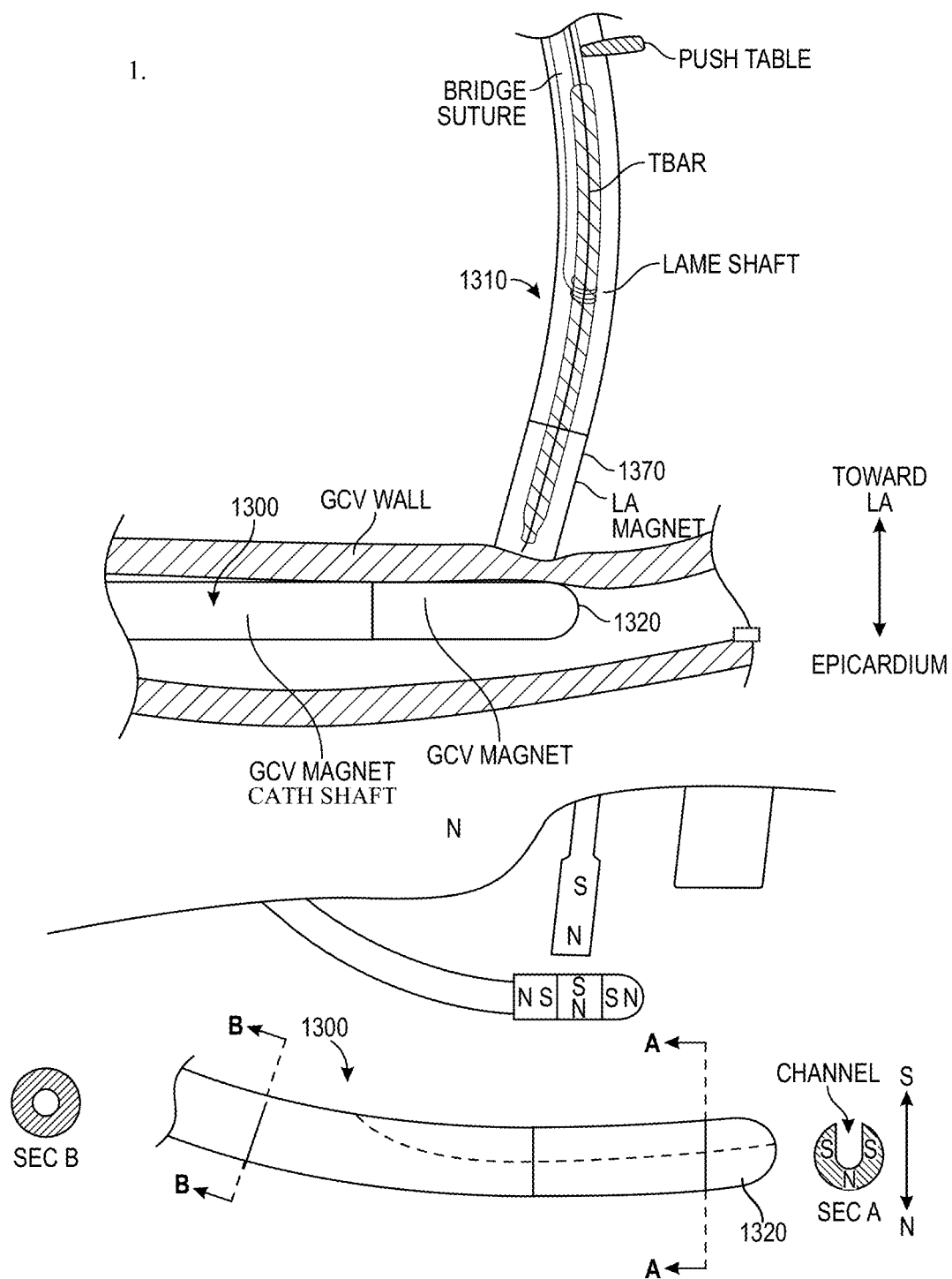
FIG. 37 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 38:
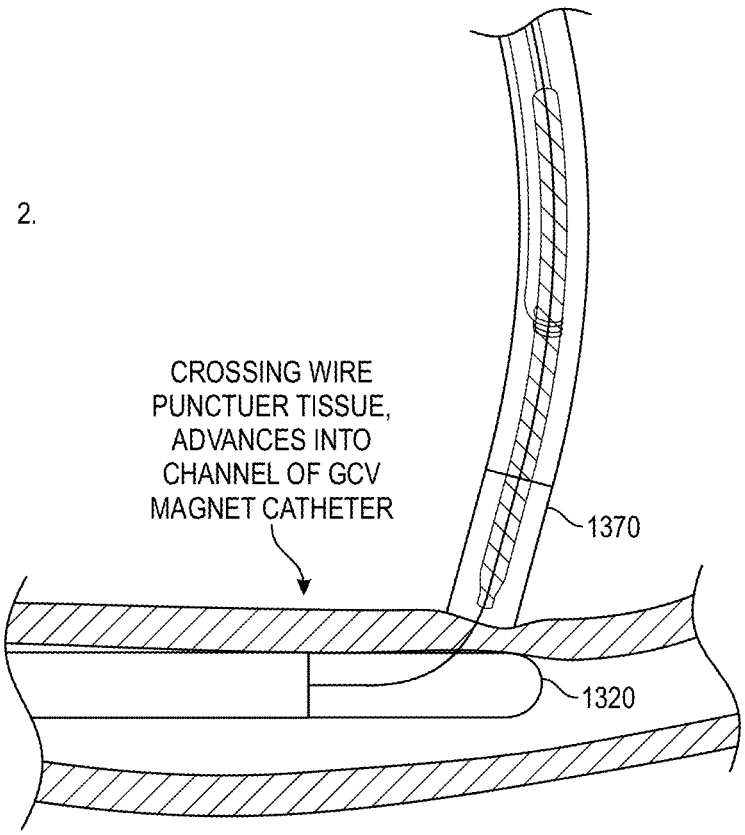
FIG. 38 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 39:
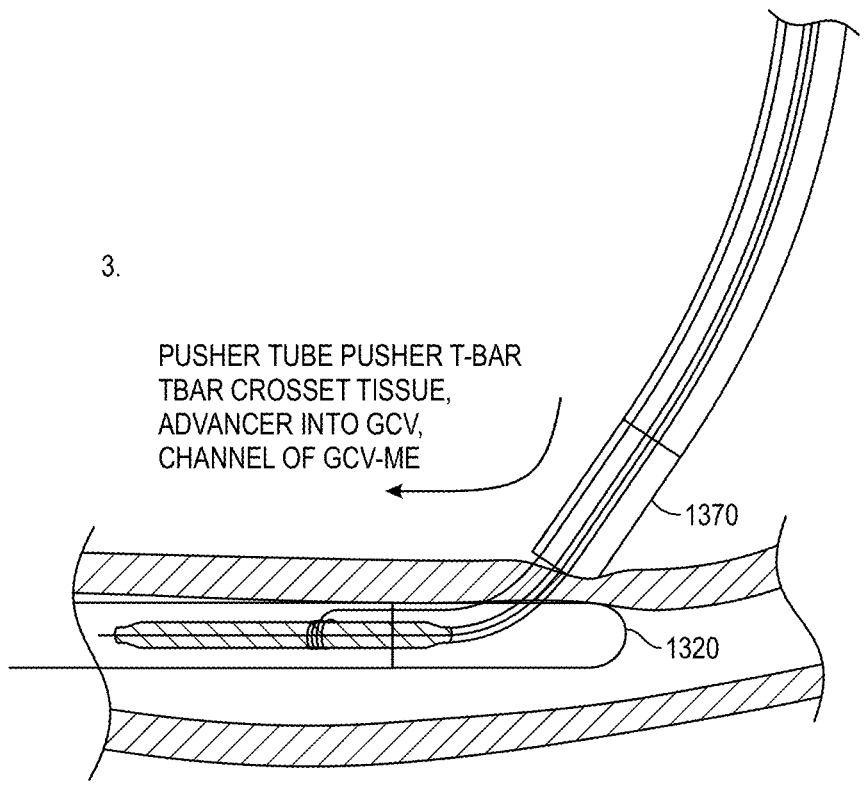
FIG. 39 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 40:
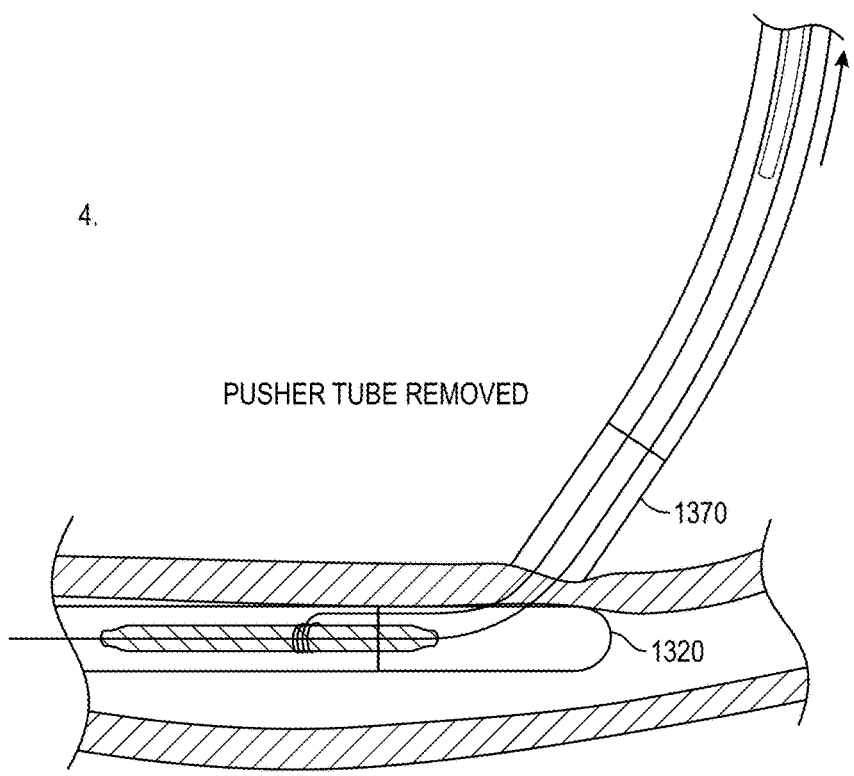
FIG. 40 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 41:
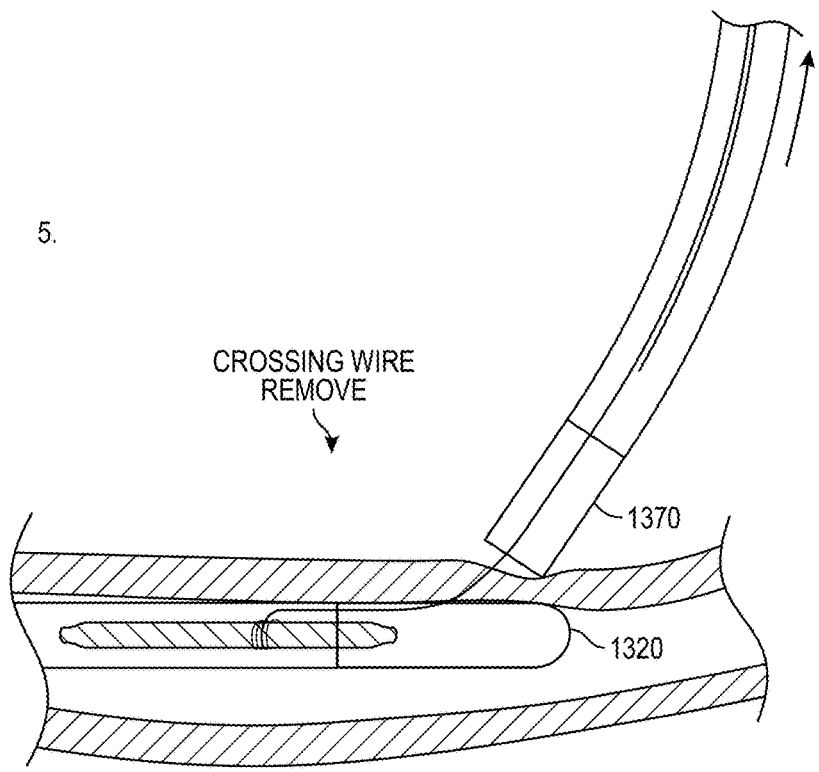
FIG. 41 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 42:
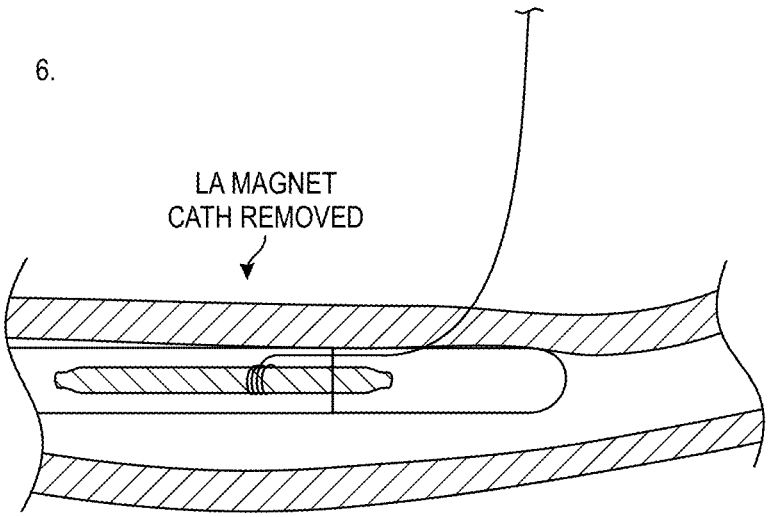
FIG. 42 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 43:
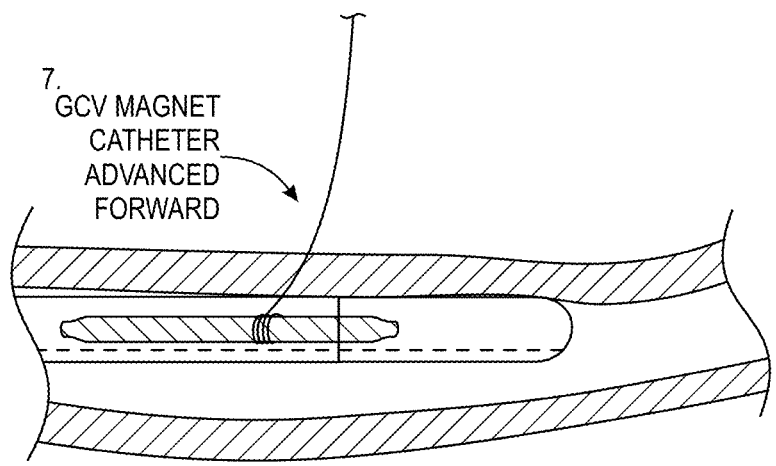
FIG. 43 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 44:
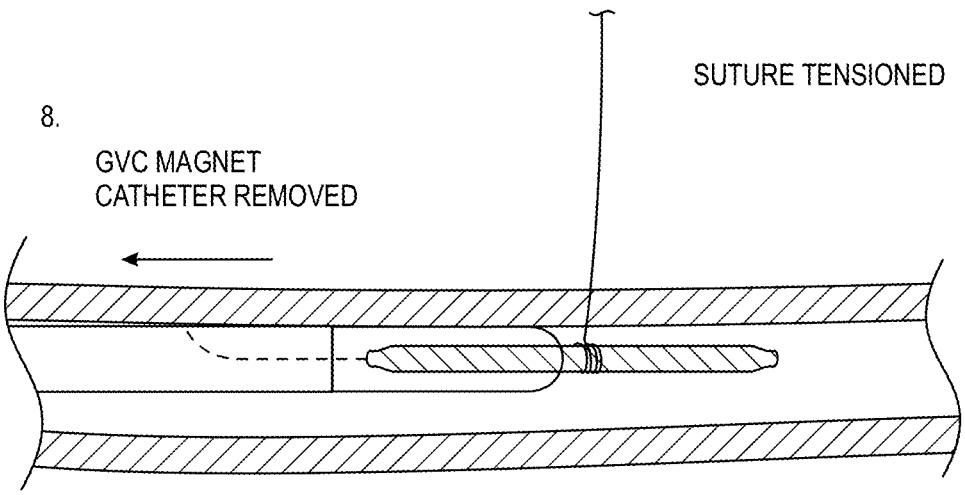
FIG. 44 illustrates portions of a procedure in which the magnetic catheter system of the invention is being used to advance the penetrating member, e.g., the crossing wire, from the left atrium into the GCV and advancing the posterior anchor into the GCV from the left atrium.
Figure 45:
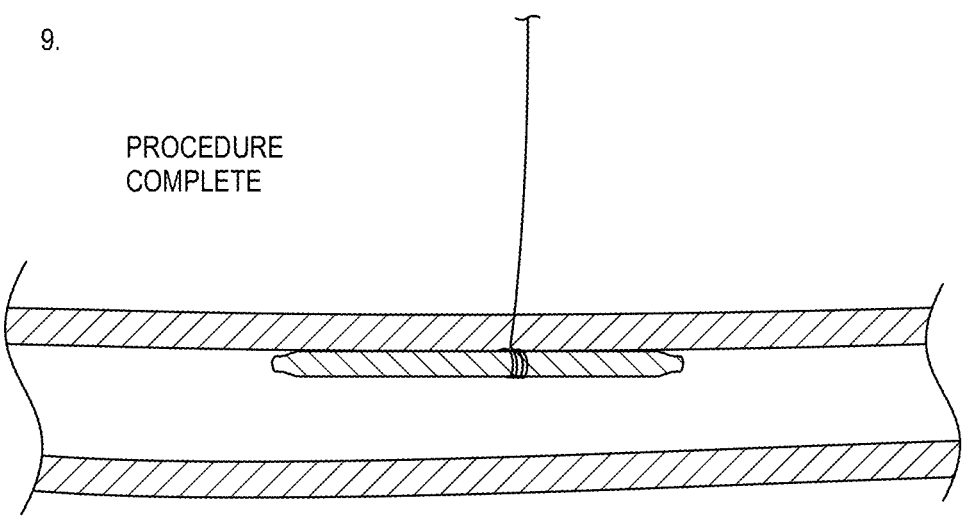
FIG. 45 illustrates portions of a procedure in which the magnetic catheter system of the invention is being used to advance the penetrating member, e.g., the crossing wire, from the left atrium into the GCV and advancing the posterior anchor into the GCV from the left atrium.

FIGS. 37-45 illustrate portions of a procedure in which the magnetic catheter system of the invention is being used to advance the penetrating member (e.g., the crossing wire), from the left atrium into the GCV and advancing the posterior anchor into the GCV from the left atrium. FIG. 37 shows the magnetics heads of the LA and GCV catheters being magnetically coupled with the GCV wall being sandwiched between the magnetic heads of the respective catheters. As shown in FIG. 38, the penetrating member, e.g., crossing wire, is advanced along the lumen of the LA catheter to puncture the GCV wall and then advanced into the magnetic channel of the GCV catheter within the GCV. Next, a pusher tube is used to advance the posterior T-bar anchor across the punctured tissue into the magnetic head of the GCV catheter as shown in FIG. 40. The crossing wire is then removed by withdrawal through the lumen of the LA catheter as shown in FIG. 41. The LA catheter is then removed as shown in FIG. 42 and the GCV catheter is advanced forward in the GCV to position the posterior T-bar anchor and suture bridge as shown in FIG. 43. The suture bridge is then tensioned and the GCV catheter withdrawn from the GCV thereby leaving the posterior T-bar anchor in the GCV to complete the implantation procedure as shown in FIGS. 44 and 45.

Figure 46:
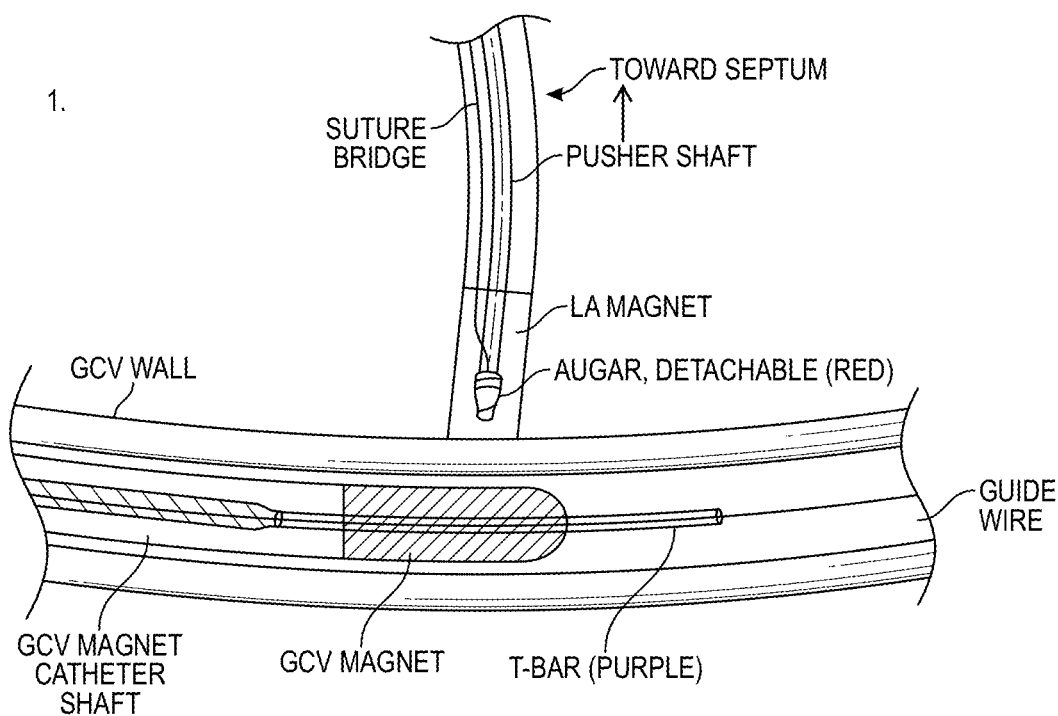
FIG. 46 illustrates portions of a procedure in which the magnetic catheter system of the invention is being used to advance a penetrating member (e.g., pusher shaft) having an auger tip attached to a suture bridge from the left atrium into the GCV to attach the auger tip and suture bridge to a posterior anchor positioned in the GCV.
Figure 47:
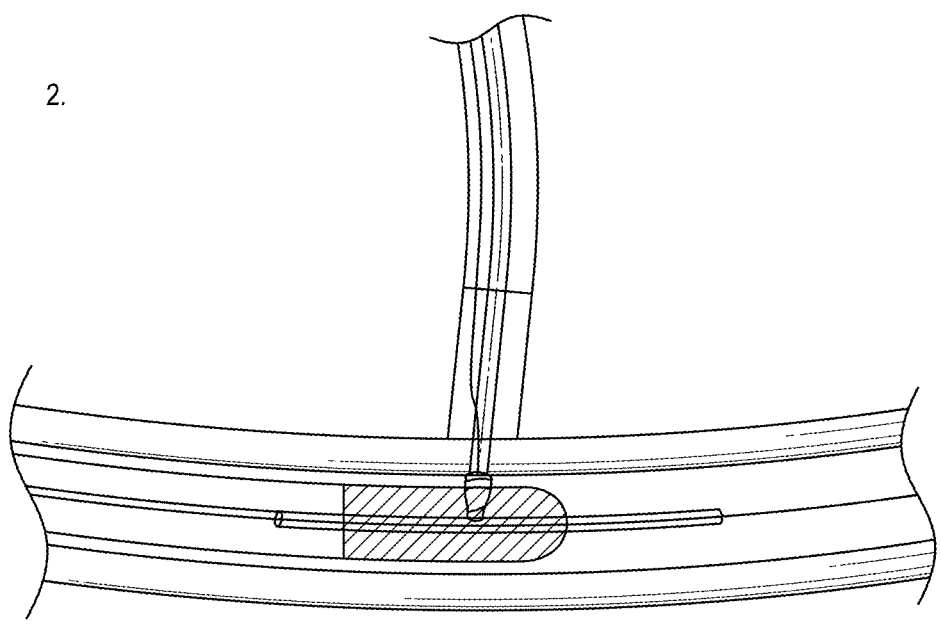
FIG. 47 illustrates portions of a procedure in which the magnetic catheter system of the invention is being used to advance a penetrating member (e.g., pusher shaft) having an auger tip attached to a suture bridge from the left atrium into the GCV to attach the auger tip and suture bridge to a posterior anchor positioned in the GCV.
Figure 48:
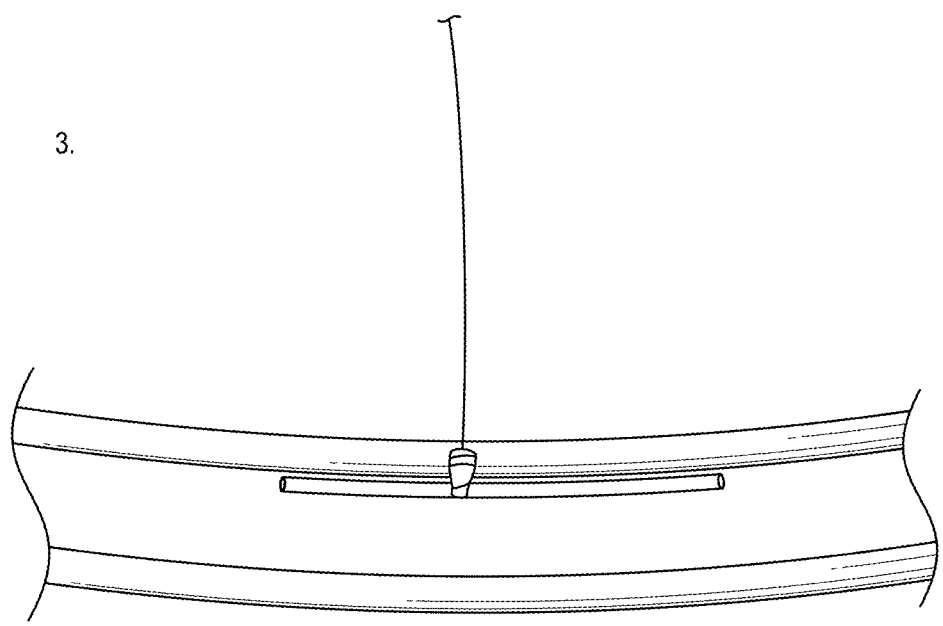
FIG. 48 illustrates portions of a procedure in which the magnetic catheter system of the invention is being used to advance a penetrating member (e.g., pusher shaft) having an auger tip attached to a suture bridge from the left atrium into the GCV to attach the auger tip and suture bridge to a posterior anchor positioned in the GCV.

With reference to FIGS. 46-48, in some aspects, the penetrating member goes from outside-in (from LA to GCV). As shown in FIG. 46, the posterior T-bar anchor is delivered to a target site in the GCV via the GCV catheter and the magnetic heads of the LA and GCV catheters are magnetically coupled.

In various aspects, the penetrating member is a pusher shaft that includes a detachable auger tip that is advanced from the left atrium side through the LA catheter. The detachable auger tip is also attached to a suture bridge. During implantation, the auger tip is advanced on the pusher shaft along the LA catheter and screwed through the left atrium wall and into the side of the posterior anchor which is sitting in a groove of the GCV catheter magnet, as shown in FIGS. 47 and 48. The pusher shaft is then detached from the auger tip and backed out of the LA catheter leaving behind the suture bridge which is attached to the posterior anchor via the auger tip. The LA catheter is then withdrawn and the GCV catheter is withdrawn with the posterior anchor being implanted. Due to the simplicity of crossing, multiple bridges may be easily deployed in a short time. Strong magnet pairing (high counter traction force) improves the ability of the penetrating guidewire to advance and screw into the posterior anchor. In some aspects, the posterior anchor itself has a side slot which the auger tip can connect with. Also, it is envisioned that the posterior anchor may be composed of a rubber, silicone, or polymeric material that the screw tip can easily screw into. Once the screw tip is connected to the posterior anchor, the control guidewire detaches from the screw tip, leaving behind the suture bridge.

As discussed herein, FIGS. 37-45 further illustrate use of the magnetic catheter system of the invention in a procedure including advancing the penetrating member, e.g., the crossing wire, from the left atrium into the GCV and advancing the posterior anchor into the GCV from the left atrium.

It will be appreciated that the magnetic catheter system of the present invention (depicted in FIGS. 37-45) provides an alternate means to deliver the posterior anchor to the GCV. In practice, the GCV magnet catheter, e.g., the first catheter, and the LA catheter, e.g., the second catheter, are delivered as discussed herein and a magnetic connection is made across the left atrial wall with an intended crossing/puncture site just over the P2 mitral leaflet. A penetrating member, e.g., crossing wire, is delivered from the LA magnet catheter and punctures toward/into the tip of the GCV magnet catheter. In some aspects, the GCV catheter is shaped so that it receives the crossing wire tip and is deflected proximally down the catheter shaft. A posterior anchor, such as a T-bar, is advanced down the crossing wire from the LA catheter. The crossing wire and T-bar may be co-axial with the magnets of the LA catheter in one aspect (magnet cross-section must allow), or they may be side-by-side. The T-bar distal end has a tapered tip so it may penetrate through the crossing hole, allowing the T-bar to be pushed through the hole. In some aspects, there is a pushing tube behind the T-bar, pushing it across the hole. Once the T-bar is through the hole, the pushing tube may be backed out and removed. The crossing wire is removed, either by backing it out from the femoral access or advancing the puncture end all the way to the jugular access site and then pulling the wire out from there. In the procedure, the GCV catheter is advanced forward (toward AIV) or a means is provided to advance the T-bar a small distance (about ½ a T-bar length) so that when the bridging element is tensioned from the septal side, the T-bar attachment point is directly under the crossing hole. The two magnetic catheters are then completely removed from the patient.

It will be appreciated that this system and procedure simplifies the way the posterior anchor is delivered as compared to conventional delivery methods. Notably, the need to deliver a loop of suture (requiring a cassette to feed out loop) is eliminated. Additionally, there is no need for a steering tube. Further, it will be appreciated that it is possible to deliver multiple posterior anchors using this procedure without the need to remove and replace the GCV catheter each time.

Catheter Configurations

As discussed previously, one purpose of some such delivery catheter configurations is to facilitate deployment of the posterior anchor while keeping the bridging element totally within the protection of the magnetically connected catheters by combining the magnets and keeping the posterior anchor on one delivery catheter in the great cardiac vein. Examples of such delivery catheter configurations are detailed below. It is appreciated that any of the aspects or features described in certain embodiments may be utilized in various other embodiments in accordance with the concepts described herein.

Figure 17:
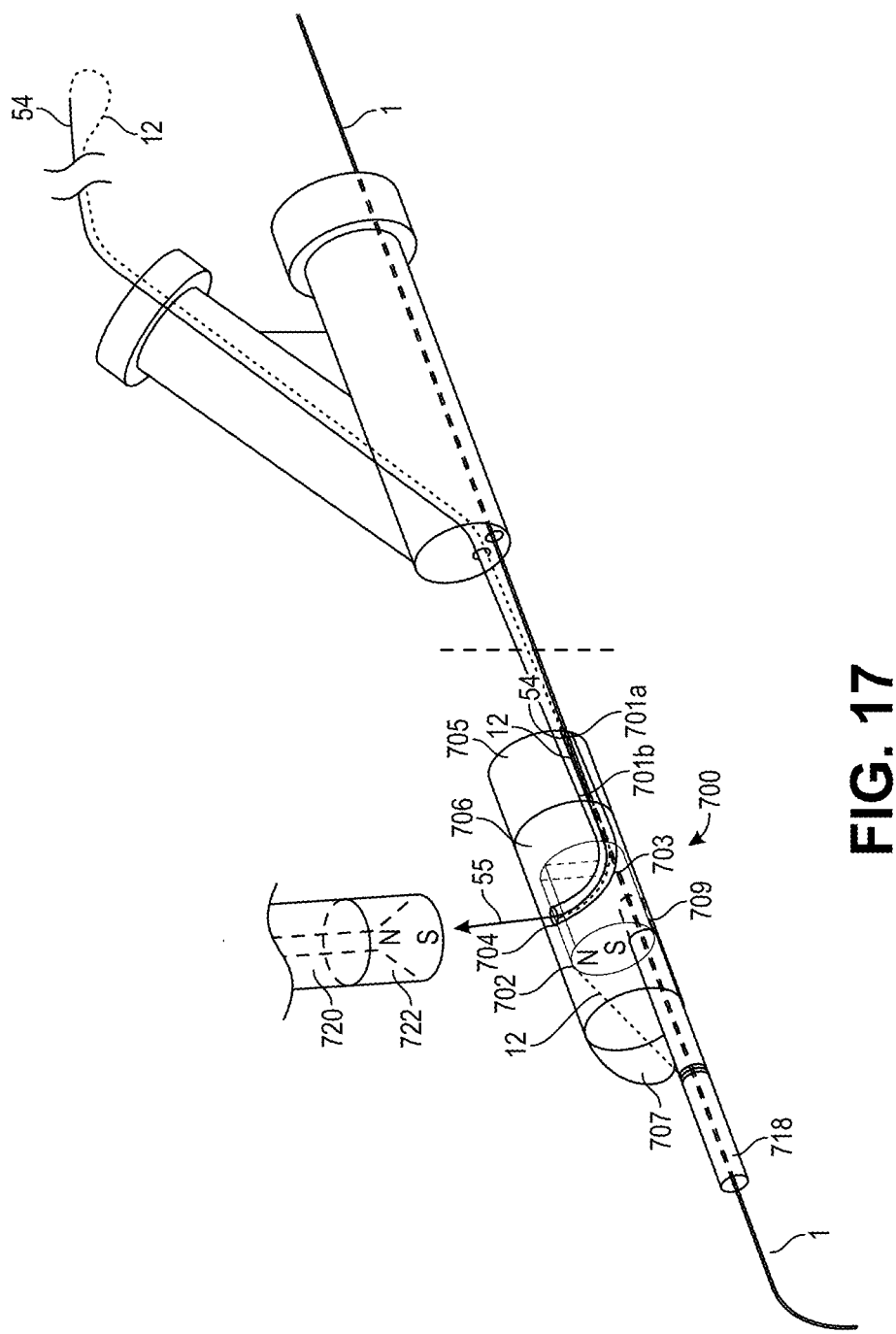
FIG. 17 illustrates an example of a catheter system for delivery and deployment of an implant system for treatment of mitral valve regurgitation, in accordance with aspects of the invention.
Figure 18:
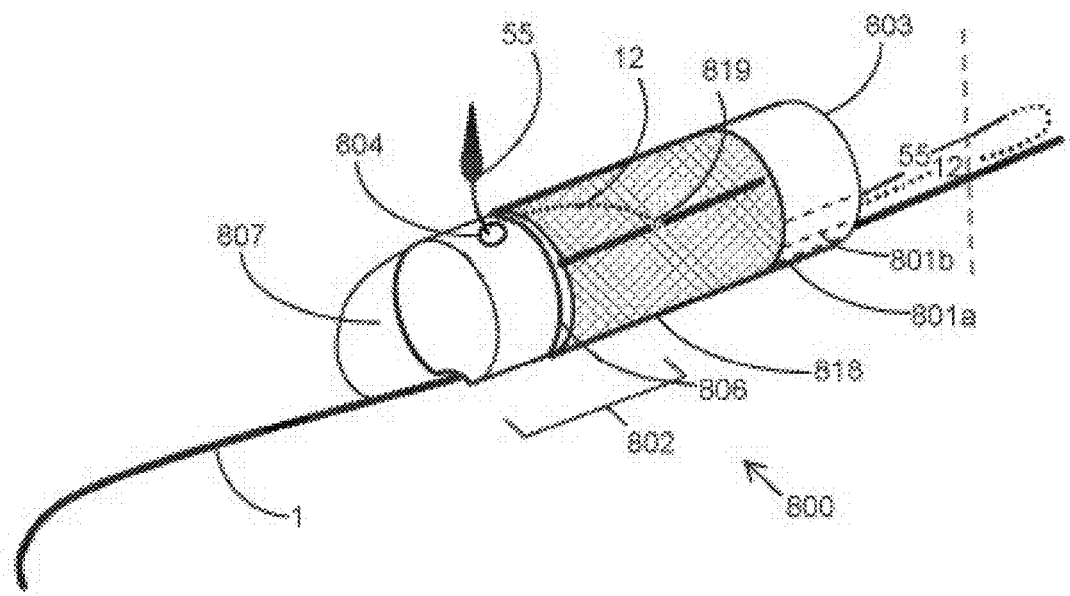
FIG. 18 illustrates an example of a catheter system for delivery and deployment of an implant system for treatment of mitral valve regurgitation in accordance with aspects of the invention.
Figure 19:
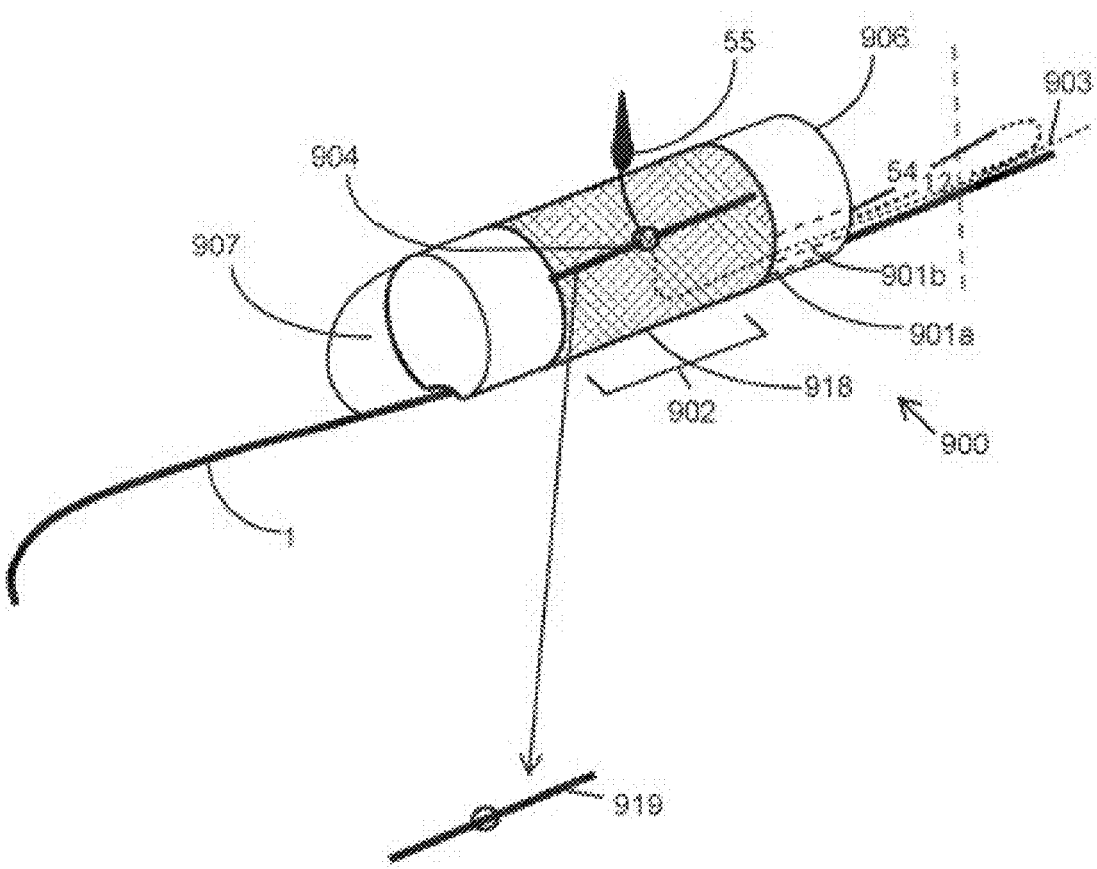
FIG. 19 illustrates an example of a catheter system for delivery and deployment of an implant system for treatment of mitral valve regurgitation, in accordance with aspects of the invention.

FIG. 17-19 show anchor delivery catheter configuration in accordance with aspects of the invention. In particular, the catheter configuration allows for magnetically coupling with a corresponding catheter to establish access within a heart chamber from adjacent vasculature and delivering a heart implant in accordance with aspect of the invention. These example delivery catheters are configured for use within a GCV catheter 50, within the example delivery and deployment methods depicted above. It is appreciated that the following catheter configurations can include any of the various aspect described herein (for example, length, materials, dimensions, and the like), but are not limited to the aspects described herein and could be configured as needed for a particular use or anatomy.

FIG. 17 shows a distal portion of a delivery catheter configuration 700 that includes a guidewire lumen 701a extending longitudinally to facilitate advancement of the catheter along a guidewire 1 positioned in the vasculature of the patient (for example, within the great cardiac vein when the catheter configuration is utilized in a GVC anchor delivery catheter). The catheter can further include a puncture wire lumen 701b dimensioned to allow passage of the puncture wire and subsequent passage of the bridging element 12 attached thereto. The catheter includes a magnetic head 702 configured to magnetically couple with a magnetic head 722 of a corresponding catheter 720 through a tissue wall therebetween. Magnetic head 702 is defined so that the magnetic poles of the magnetic head are disposed laterally relative a longitudinal axis of the catheter so as to couple in a perpendicular orientation with magnetic head 722 of magnetic catheter 720, in a similar fashion as in FIG. 11C. The magnetic head 702 further includes a guide channel 703 defined to steer puncturing guidewire 54 upward through an exit hole 704 on one side of the magnetic head 702 to direct the sharped distal tip 55 (for example, flat tip) of the puncturing guidewire 54 through the tissue wall and into the magnetic head 722 of catheter 720. The magnetic head 722 is defined with a central channel that is funnel-shaped so as to direct the puncturing wire 52 into the central channel. The dashed vertical line in FIGS. 17-19 represents the point at which the delivery catheter extends outside the body. In any of these embodiments, the guidewire 1 and bridging element 12 and puncturing wire 54 can extend through a Y-arm connector to facilitate independent manual control of the guidewire 1 and the puncturing wire 54/bridging element 12. (The catheter shaft extending between the distal end portion and the Y-arm connector is not shown). In such embodiments, the length of the puncturing wire 54 is greater than the sum of both magnetic catheters, and the length of bridging element 12 is at least long enough to extend from the posterior anchor to the second access site, so that when the puncturing wire is pulled from the second access site it pulls the bridging element out the second access site. In some embodiments, the bridging element (suture) may be long enough that it remains outside the first access site until it is pulled out of the second access site. This may be desired in the unlikely event that the suture becomes disconnected from the puncturing wire before the suture is pulled out the second access site so that the operator may retrieve it by pulling on the proximal portion still out of the body. In this instance it would need to be as long as the sum of the length of the second catheter 60 and twice the length of the delivery catheter 50 since it needs to switch back as described above. It is appreciated that while the delivery catheter configuration is shown in FIG. 17 extending from right to left, the end portion of the catheter would extend from left to right when viewed from a front of the patient, such as shown in FIG. 13.

Figure 20:
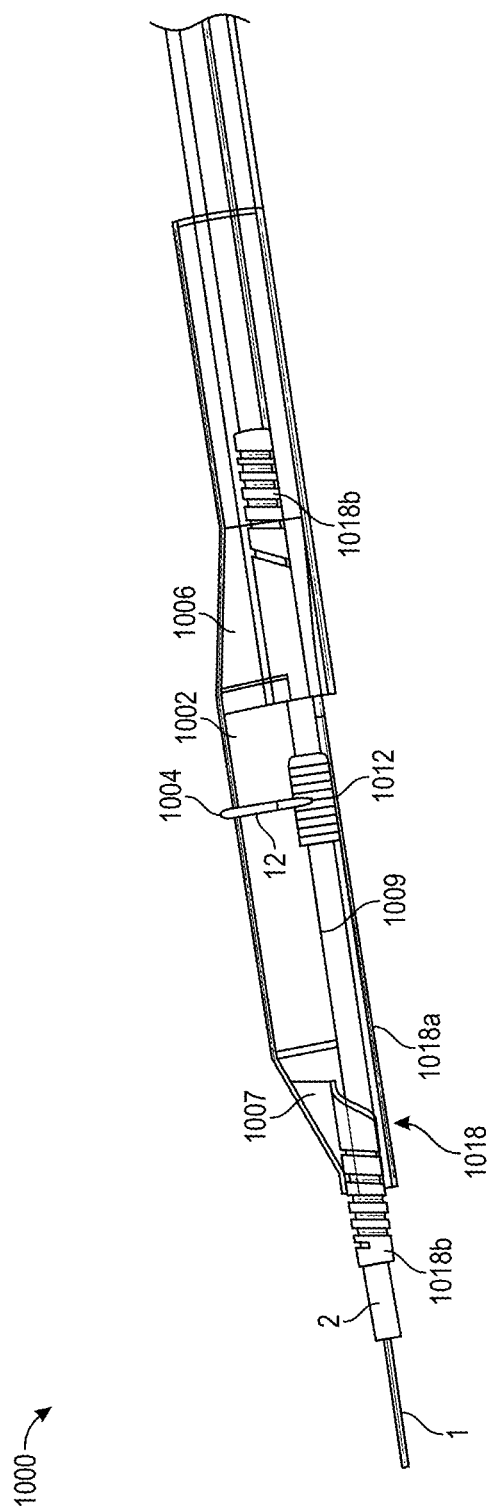
FIG. 20 illustrates an example of a catheter system for delivery and deployment of an implant system for treatment of mitral valve regurgitation, in accordance with aspects of the invention.
Figure 21:
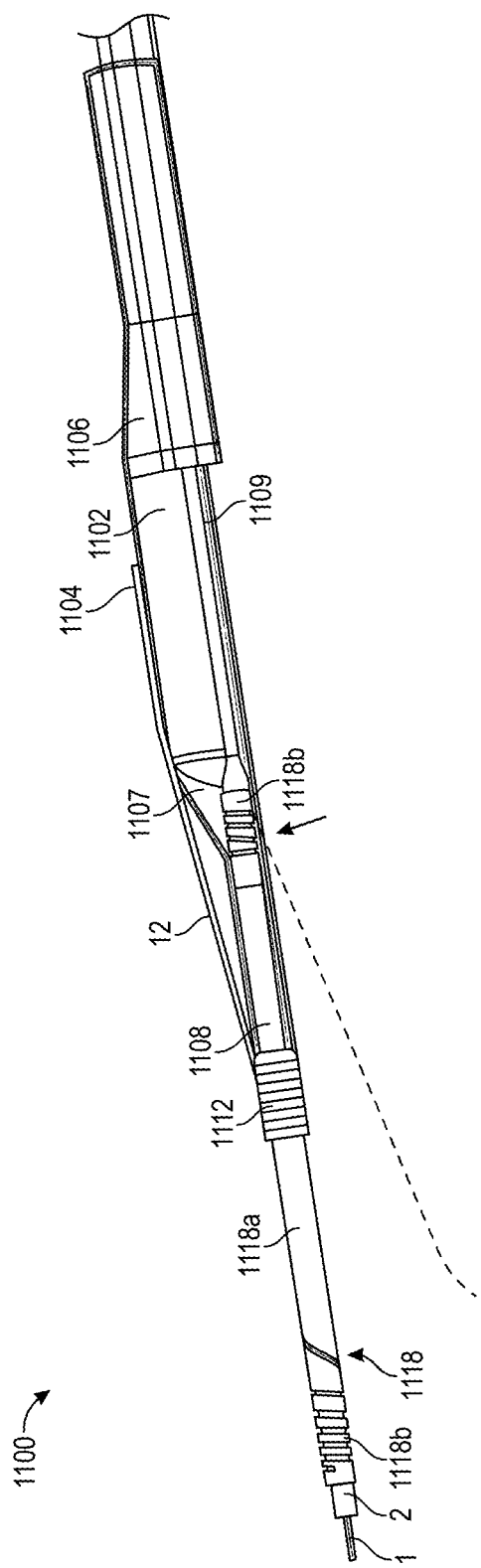
FIG. 21 illustrates an example of a catheter system for delivery and deployment of an implant system for treatment of mitral valve regurgitation, in accordance with aspects of the invention.

Catheter 700 includes a catheter shaft 705 along its length, which can be formed of any suitable material, to facilitate advancement of the catheter through the vasculature. As shown, the magnetic head 702 is formed with a notch or contoured recess in one side, which in this embodiment is opposite the exit hole 704, although could be located in any suitable location in embodiments. The notch, recess or groove 709 is configured to allow passage of the guidewire 1 and/or to receive at least a portion of posterior anchor 718. In this embodiment, posterior anchor 718 is defined as an elongate member having a longitudinal lumen through which the guidewire 1 extends. It is appreciated that a posterior anchor having a longitudinal lumen through which the guidewire 1 extends could be utilized in any of the embodiments described herein. It is further appreciated that the posterior anchor 718 could be positioned partly extending within a recess of the magnetic head, extending distally of the magnetic head (as shown) or proximally, or could extend proximally and proximally and distally of the magnetic head (as shown in FIG. 20) or could be disposed entirely proximal or entirely distal of the magnetic head (as shown in FIG. 21).

An outer jacket 706 covers the magnetic head 702 and includes an opening over exit hole 704 to allow passage of the penetrating guidewire 54 therethrough. Typically, the outer jacket 706 is formed for a flexible polymer material and is defined to form a smooth interface with the catheter shaft 705. The outer jackets helps maintain the magnetic head 702 within the catheter and may extend at least partly over the posterior anchor 718 to help retain the posterior anchor 718 during advancement of the catheter through the vasculature. Optionally, a polymeric rounded tip 707 can be provided on a distal end of the jacket to facilitate advancement of the catheter through the vasculature.

FIG. 18 shows a distal portion of a delivery catheter configuration 800 that includes a guidewire lumen 801 extending longitudinally to facilitate advancement of the catheter along a guidewire 1 positioned in the vasculature of the patient, within the great cardiac vein when the catheter configuration is utilized in a GVC anchor delivery catheter. The catheter can further include a puncture wire lumen 801b dimensioned to allow passage of the puncture wire 54 and subsequent passage of the bridging element 12 attached thereto. The catheter includes a magnetic head 802, contained within inner jacket 803, that is configured to magnetically couple with a magnetic head of another catheter on an opposite side of a tissue wall, as described in other embodiments. The magnetic head includes a guide channel (not shown) to direct the puncture guidewire 54 through exit hole 804 on one side of the magnetic head and into a lumen of the other catheter when magnetically coupled. The inner jacket 803 includes an opening over the exit hole 804 to allow passage of the distal sharpened end 55 (for example, flat tip) of puncturing guidewire 54. As shown, the posterior anchor 818 is defined as an expandable scaffold. Here, the expandable scaffold is self-expanding and constrained into the configuration shown by a constraining sheath 806 (shown as transparent for improved visibility of underlying components). Proximal retraction of the constraining sheath 806 allows the expandable scaffold posterior anchor 818 to expand and release from the inner jacket 803. The bridging element 12 is attached to the proximal end of the puncturing guidewire 54 and extends back through the catheter, out through exit hole 804 outside of the inner jacket to a reinforcing rib 819 on the posterior anchor 818 such that once the bridging element 12 is passed through the exit hole and across the heart chamber and the posterior anchor 818 is deployed, catheter 800 can be withdrawn from within the deployed posterior anchor 818 and the implantation process can proceed with deployment of the anterior anchor, as described above. In some embodiments, deployment may further entail laterally collapsing the scaffold by pulling of bridging element 12.

FIG. 19 shows a distal portion of a delivery catheter configuration 900 that includes a guidewire lumen 901a extending longitudinally to facilitate advancement of the catheter along a guidewire 1 positioned in the vasculature of the patient, within the great cardiac vein when the catheter configuration is utilized in a GVC anchor delivery catheter. The catheter can further include a puncture wire lumen 901b dimensioned to allow passage of the puncture wire 54 and the bridging member length extending to the preloaded posterior anchor, and in some embodiments the tether releasing wire. The catheter includes a magnetic head 902 (not shown) contained within an outer jacket 906, the magnetic head being configured to magnetically couple with a magnetic head of another catheter, as described above. The magnetic head includes a guide channel (not shown) to direct the puncture guidewire 54 through an exit hole 904 and into a lumen of the other catheter when magnetically coupled. The outer jacket 906 includes an opening over the exit hole 804 to allow passage of the distal sharpened end 55 of puncturing guidewire 54 through exit hole 904. As shown, the posterior anchor 918 is defined as a non-expandable scaffold. The scaffold can be secured in place by a releasable coupling, such as a suture or tether 903 that extends inside a lumen of the catheter to its proximal end, such that removal of the tether releases the scaffold. Release can be further facilitated by gently tugging the bridging element 12 advanced through the other magnetically coupled catheter. Catheter 900 can then be retracted and the implantation process can proceed with deployment of the anterior anchor, as described above. In some embodiments, deployment may further entail laterally collapsing the scaffold by pulling of the bridging element 12.

FIG. 20 shows a distal portion of a delivery catheter configuration 1000 having a magnetic head 1002 and a posterior anchor 1018 that is disposed over a guidewire 1 along which the catheter is advanced through the vasculature. In this embodiment, the posterior anchor 1018 is mounted within a groove 1009 defined within the magnetic head so as to be axially "stacked" and completely overlapping the magnetic head. The magnetic head includes with a side hole 1004 through which the penetrating guidewire can be advanced and from which the bridging element 12 extends and attaches to the posterior anchor 1018 at attachment feature 1012. The posterior anchor includes a central portion 1018a that is substantially rigid and that includes the attachment feature 1012 and strain relief portions 1018b on each end that allow flexure so that the distal portion of the catheter can have some flexibility to accommodate curvature of the vasculature through which it is advanced. In this embodiment, the system includes a reinforced guidewire lumen 2 (for example, braided or coiled wire lumen) to facilitate advancement of the posterior anchor and prevent kinking when advanced along a curved path. An outer jacket 1006 extends over the magnetic head and includes an opening over the exit hole 1004 and may include a distally tapered portion 1007 having an opening through which the posterior anchor 1018 can be deployed. Once the bridging element is delivered through a second catheter magnetically coupled to the delivery catheter, as described previously, the posterior anchor 1018 can be released by withdrawing the guidewire 1 and guidewire lumen 2, and can be further facilitated by gently tugging the bridging element 12 advanced through the other magnetically coupled catheter. In some embodiments, the posterior anchor 1118 can be further secured by a releaseable coupling feature and released by retracting a tether, as previously described.

Previously described non-stenting "hypo-tube" posterior anchor deployment catheters, with an internal lumen dedicated to a guidewire, have relied on the bridge attachment location on the anchor to the to be aligned and mounted on the delivery catheter at or very near the exit hole of the puncturing wire in the magnet. One perceived advantage of such delivery catheter designs is that the anchor is at or immediately adjacent the puncture site at the time of the puncture and does not have to be repositioned before release from the catheter. One draw back associated with such designs is the larger profile, bulk and increased stiffness of the staked catheter elements in this distal section. Such designs where the posterior anchor is mounted within or partly within the magnetic portion of the delivery catheter, while suitable, may not always be ideal because the ability to advance the distal portion of the delivery catheter, in curves and torque the catheter in small vasculature, particularly the great cardiac vein, is compromised. Another drawback is that in order to fit the anchor and maintain relatively reduced profile, some magnet bulk is removed over past designs, which reduces its magnetic strength. This in turn makes alignment with and attachment to the mating catheter more skill dependent and may require more catheter manipulation. In order to further reduce delivery profile and increase flexibility without loss of magnetic energy, some preferred embodiments of the delivery catheter utilize an anchor that is axially offset from the magnetic head along the longitudinal axis of the catheter, for example, as shown in FIG. 21.

FIG. 21 shows an exemplary delivery catheter configuration 1100 having a magnetic head 1102 and a posterior anchor 1 118 that is axially offset from the magnetic head 1102 along a longitudinal axis of the catheter so as to be non-overlapping with the magnetic head. The posterior anchor 1118 is disposed over a guidewire 1 along which the catheter is advanced through the vasculature. In this embodiment, the magnetic head 1102 includes a smaller groove 1109 defined within the magnetic head through which the guidewire lumen 2 extends. The magnetic head includes a side hole 1104 through which the penetrating guidewire can be advanced and from which the bridging element 12 extends and attaches to the posterior anchor 1118 at attachment feature 1112. The posterior anchor includes a central portion 1118a that is substantially rigid and that includes the attachment features 1112 and strain relief portions 1118b on each end that allow flexure so that the distal portion of the catheter can have some flexibility to accommodate curvature of the vasculature through which it is advanced. The strain relief portions 1118b are defined as helical cut portions in the elongate tube defining the posterior anchor 1118. In this embodiment, the system includes a reinforced guidewire lumen 2 (for example, braided or coiled wire lumen) to facilitate advancement of the posterior anchor and prevent kinking when advanced along a curved path. An outer jacket 1106 includes an opening over the exit hole 1104 and can include a distally tapered portion 1107 having an opening surrounding a proximal portion of posterior anchor 1118 and luminal extension 1108. Once the bridging element is pulled through the second catheter magnetically coupled to the delivery catheter, as described previously, the posterior anchor 1118 can be released by withdrawing the guidewire 1 and guidewire lumen 2, and can be further facilitated by gently tugging the bridging element 12 advanced through the other magnetically coupled catheter. In some embodiments, the posterior anchor 1118 can be further secured by a releaseable coupling feature, for example, a tether or tether loop that engages the posterior anchor to the distal portion of the catheter and that is released by retracting a tether, as previously described.

The primary feature that reduces profile and increases flexibility is the placement of the posterior anchor in front of the magnet and over a guidewire. This design leverages the natural flexural properties of the proximal of the two stress relieving atraumatic ends (for example, strain relief portions) of the posterior anchor design creating a bending point (see arrow in FIG. 21) allowing the distal portion to bend or flex relative the magnetic head portion (see dotted line) to better approximate the curve of a body lumen or vasculature, such as the GCV. Compared to the larger catheter magnet tip profile section described above in FIG. 20, the posterior anchor at the tip of the delivery catheter of FIG. 21 better approximates the natural reducing diameter of the vasculature as the catheter is delivered, advancing it distally.

Because the bending is concentrated to single point between to quasi-rigid sections, transitional construction features can be added to aid in its translational and rotational performance during placement and inhibit kinking at the joint or binding the guidewire. On the inner diameter, a reinforced guidewire lumen 2 (for example, a braided or coiled wire) that spans the full length of the catheter can be used to facilitate advancement of the posterior anchor. In some embodiments, the reinforced guidewire lumen is dimensioned to substantially fill the luminal space between the guidewire and posterior anchor. The outer flexible polymeric luminal extension 1108 around the anchor that ends at bridging element attachment point stepwise transitions bending of the distal portion of the catheter. On the outer diameter in front of the magnet the distally tapered portion 1107 can be defined as a flexible conical section to limit the amount of bending over the flex point and acts as a smooth transition against the vasculature wall mitigating disparate diameters of the magnetic head and posterior anchor cross-sections.

Both designs shown in FIGS. 20-21 allow the delivery of hollow posterior anchors within magnetically connected delivery catheters, largely without exposure of the suture bridge to tissue.

In some embodiments, a releasable coupling, such as a tether connected to the proximal end of the delivery catheter holds the posterior anchor in place during placement and releases the posterior anchor when in place. A stacked design with the posterior anchor partly or completely overlapping with the magnetic head has the advantage of one step location and delivery, but bulk and stiffness limit its distal excursion into smaller vasculature and the design can be more difficult to construct. An offset design with the posterior anchor being offset (for example, distal or proximal of the magnetic head) allows for passage deeper into the vessel, particularly smaller vasculature, and is easier to construct, however, it may warrant an additional repositioning step for anchor delivery after the initial crossing exposing a short section of suture with magnets unconnected.

In some embodiments, the catheter may include one or more radiopaque markers to help with translational and rotational alignment of the delivery catheter and facilitate magnetic connection to the mating catheter. It is desirable to align the side hole in the magnetic head of the first catheter with an opening in the second catheter before magnetic coupling as this allows for more consistent, robust magnetic coupling while minimizing skill dependent maneuvering of the catheters to align. In some embodiments, the catheter includes two radiopaque markers that are asymmetrical in shape and/or location relative the longitudinal axis of the respective catheter so as to indicate a rotational orientation of the catheter and facilitate alignment of a side hole opening in the magnetic head of the catheter with a corresponding lumen opening in a second catheter. For example, the one or more markers can include a first marker on a side of the catheter opposite the side hole and a second marker on the same side as the side hole, the second marker being different in relative location and/or size so as to be readily distinguished from the first marker and aid in determining rotational orientation. It is appreciated that these marker schemes can be used with any of the catheter embodiments described herein.

Figure 22B:
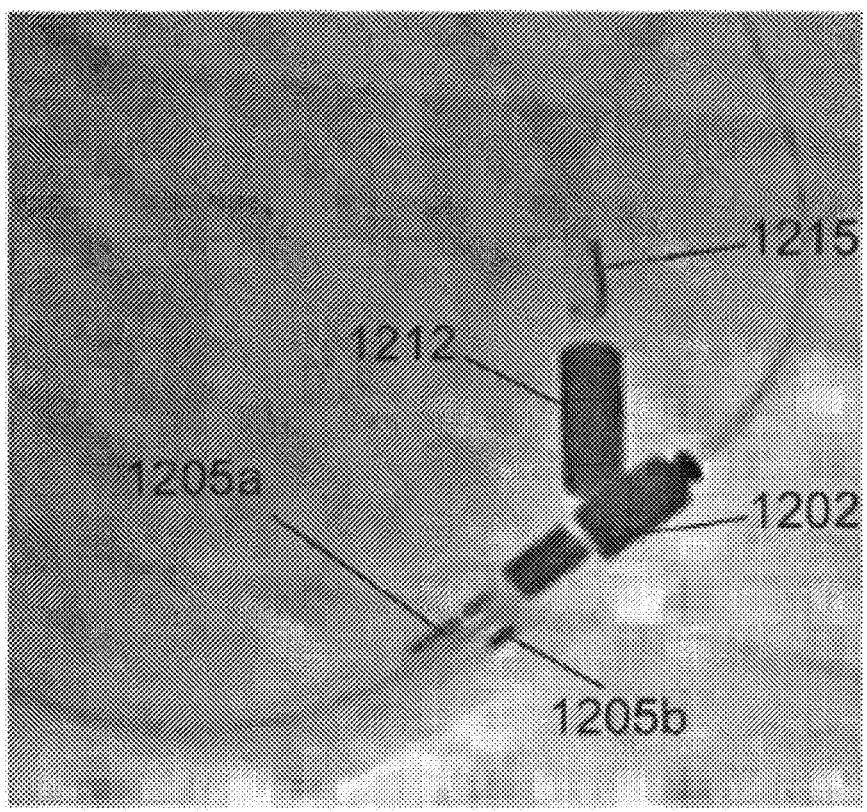
FIG. 22B depicts an image of a fluoroscopy visualization of the radiopaque markers depicted in FIG. 22A.

FIG. 22A depicts one such system having a first catheter 1201 and second catheter 1210, the first catheter 1201 having a magnetic head 1202 (for example, single, double or three piece magnet) with a side hole opening 1204 and the second catheter 1210) having a distal opening 1214 to be aligned with side hole opening 1204 for passage of the penetrating wire therethrough to establish access between the catheter. The first catheter includes two radiopaque markers 1205a, 1205b that are asymmetrical about the longitudinal axis of the first catheter to allow a user to readily determine the rotational orientation of the first catheter before the catheters are brought in close proximity and magnetically coupled. In this embodiment, the marker closest the side hole (marker 1205a) extends further proximally so that it can be readily distinguished from the opposite marker 1205b so that the rotational orientation of the first catheter and relative alignment of the catheters can be readily determined, as can be appreciated by the fluoroscopy image shown in FIG. 22B depicting a system having such markers. While the markers shown are substantially rectangular and positioned as shown, it is appreciated that various other sizes, shapes and locations of the markers can be utilized in the same manner. For example, angled lines pointing to the side hole, triangles and other shapes and sizes to help indicate direction and rotational orientation may be used. Further, it is appreciated that the magnetic heads are also fluoroscopically visible such that the second catheter may not require a separate radiopaque marker.

Figure 23:
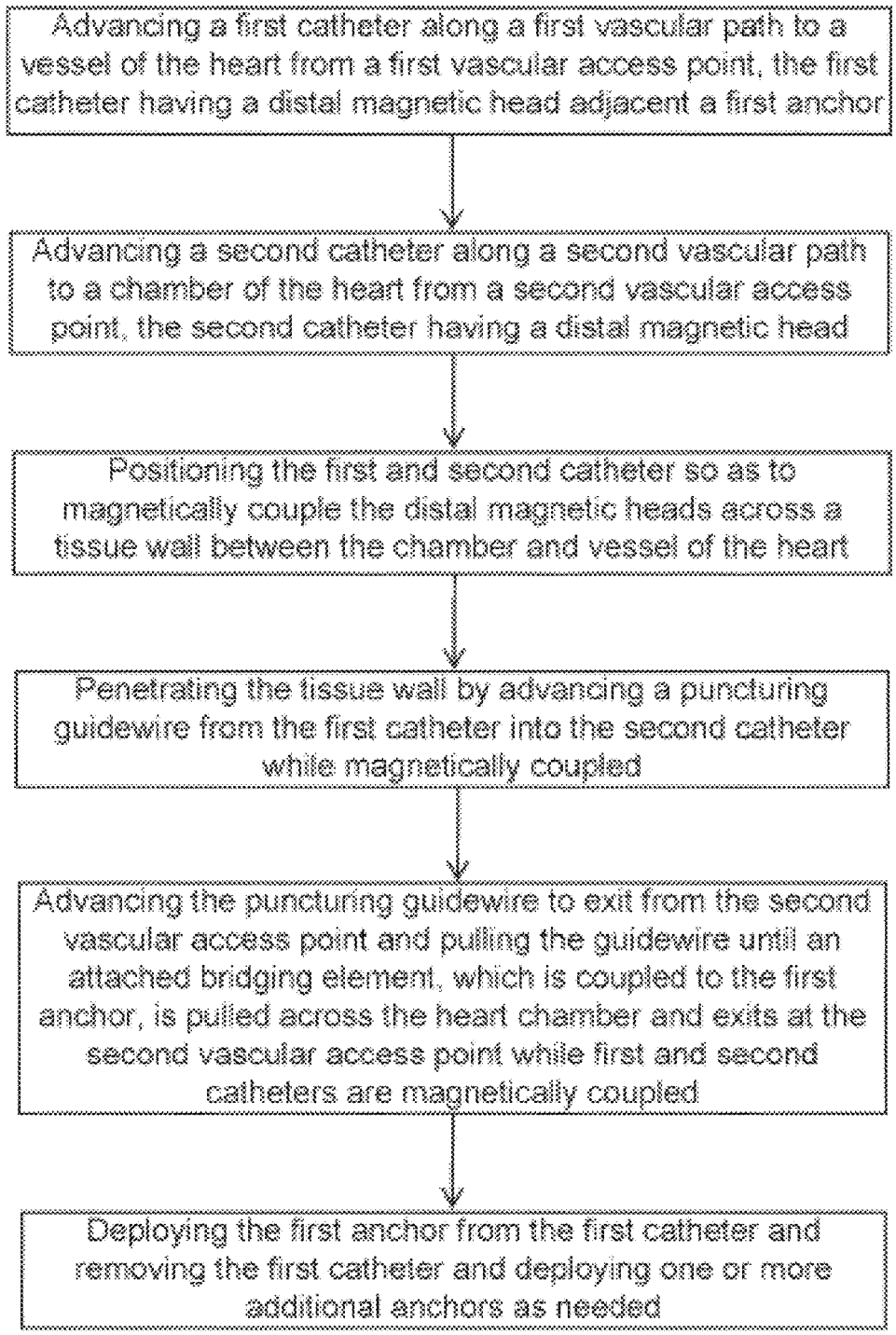
FIG. 23 depicts a method of delivering and deploying an implant system for treatment of mitral valve regurgitation, in accordance with aspects of the invention.

FIG. 23 depicts an example method of delivering and deploying an implant with a catheter system in accordance with aspects of the invention. The method includes steps of: advancing a first catheter along a first vascular path to a vessel of the heart from a first vascular access point, the first catheter having a distal magnetic head adjacent a first anchor and advancing a second catheter along a second vascular path to a chamber of the heart from a second vascular access point, the second catheter having a distal magnetic head. Next, the first and second catheter are positioned so as to magnetically couple the distal magnetic heads across a tissue wall between the chamber and vessel of the heart. Next, penetrating the tissue wall by advancing a puncturing guidewire from the first catheter into the second catheter while magnetically coupled. Advancing the puncturing guidewire to exit from the second vascular access point and pulling the guidewire until an attached bridging element coupled to the first anchor is pulled across the heart chamber and exits at the second vascular access point while first and second catheters are magnetically coupled. The first anchor is then deployed from the first catheter and the first catheter removed. Next, one or more additional anchors can be attached to one or more other portions of the bridging element extending across the heart chamber or through associated vasculature as needed for deployment of a particular type of implant.

In some embodiments, it may be desired to displace or remove the implant after deployment removing any tension and obstruction, allowing access the mitral valve and surrounding tissue. For example, in a few patients, the implant may prove ineffective or another type of implant or procedure may need to be effected (for example, intravascular valve replacement). Therefore, it would be desirable for a method and devices that allow for subsequent removal of the implant. Removal, at least partial removal, can be effected by cutting of the bridging element. The posterior anchor can be removed by use of conventional catheter techniques, or in some embodiments, can be left in place within the great cardiac vein. The septal anchor typically does not present any concern and can be left in place. Examples of such devices for cutting the bridge element of the implant are shown in FIGS. 24A-26B.

Figure 24A:
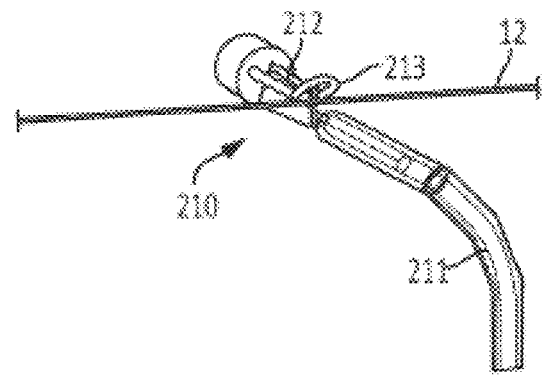
FIG. 24A depicts a step in cutting of a bridge element of an implant with a bridge cutting catheter, in accordance with aspects of the invention.
Figure 24B:
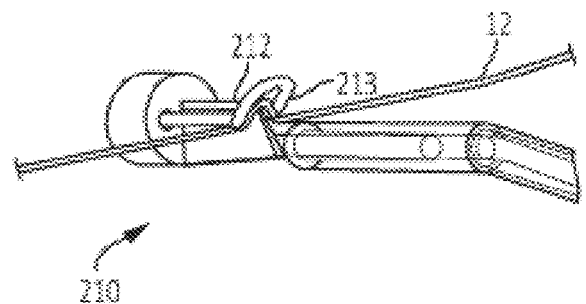
FIG. 24B depicts a step in cutting of a bridge element of an implant with a bridge cutting catheter, in accordance with aspects of the invention.
Figure 24C:
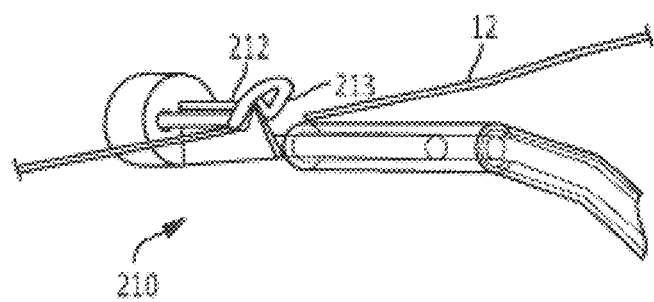
FIG. 24C depicts a step in cutting of a bridge element of an implant with a bridge cutting catheter, in accordance with aspects of the invention.

FIGS. 24A-24C shows a bridge cutting catheter 210 to facilitate removal of a deployed implant, such as any of those described herein, in accordance with aspects of the invention. Bridge cutting catheter 210 includes a curve tipped stylet 211 within an inside diameter of the catheter shaft to facilitate steering of the cutting tip to suture bridge 12. The cutting tip includes a cutting blade 212 and a capture feature 213. The cutting blade 212 includes a sharpened cutting edge along one longitudinally extending side and an angled proximal facing end surface. The capture feature 213 is a loop that is angled so as to capture the bridging element 12 and direct the bridging element to the cutting edge when the cutting catheter is proximally retracted. Since the bridging element 12 is tensioned within the deployed implant, this approach is advantageous in capturing and cutting the bridging element 12 with limited visualization. Further the shape of the loop prevents the delicate tissues of the heart from contacting the cutting edge during the procedure. In some embodiments, the cutting catheter is advanced inside a sheath. For example, the cutting catheter can be advanced inside an 8-10 F Mullins sheath that has been placed into the LA crossing the septal wall near the outer perimeter of the anterior anchor after a conventional percutaneous septodomy procedure. Some anterior anchor types will allow the delivery catheter to pass through them because of flexible or soft subcomponents or preconstructed fenestrations.

After the cutting tip is advanced from the Mullins catheter, as shown in FIG. 24A, the bridge cutting catheter 210 is positioned beyond the tensioned bridging element 12 of the deployed implant and proximally retracted so as to capture the bridging element 12 with the capture loop. As shown in FIG. 24B, once the bridging element is captured, further retraction of the bridge cutting catheter forces the bridging element upwards along the angled proximal-facing end surface of the blade and along the cutting edge, thereby cutting the bridging element, as shown in FIG. 24C.

While the presence of the cut bridging element 12 is often not of concern, there may be instances where it is desired to substantially remove any remaining bridging element 12, for example, to prevent flailing suture from entering the valve annulus and potentially interfering with placement of a valve replacement. In such instances, it may be desirable to use a tool that allow for cutting and removal of a substantial portion, or at least a majority, of the bridging element.

Figure 25:
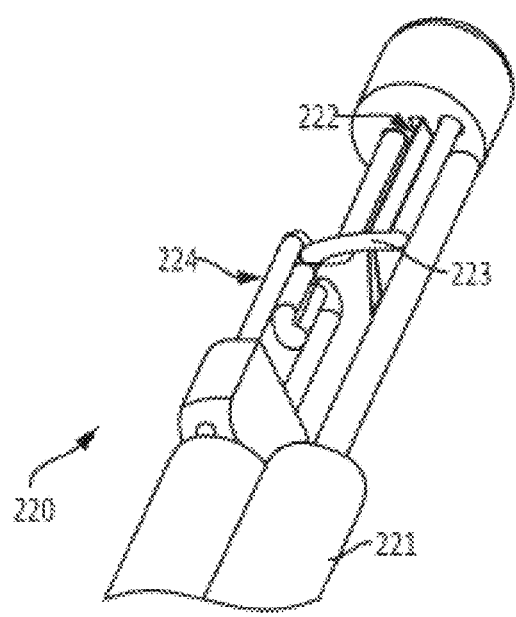
FIG. 25 depicts a bridge cutting catheter with suture grip, in accordance with aspects of the invention

FIG. 25 shows a bridging cutting catheter with suture grip 220 for cutting the bridging element and removing excess suture after cutting, in accordance with aspects of the invention. Similar to the bridge cutting catheter in FIGS. 24A-24C, the catheter includes a cutting head with a cutting blade 222 and a capture loop 223 that are configured and operate in a similar manner as described above. This catheter further includes a suture grip 224 to facilitate removal of excess suture. The catheter includes a steerable shaft 221 that allow the cutting tip to be steered to the bridge. In this embodiment, the shaft is a double shaft one shaft supporting the cutting tip while the other shaft supports a suture grip 224 that holds the bridging element during initial cutting, then operates to wind up excess suture grip, while maintaining the bridging element to allow subsequent cutting and removal of a majority of the bridging element. The suture grip 224 can be configured to hold the bridging element (for example, by friction fit, or between opposable members) and to wind up excess bridging element by rotation of an element extending through a shaft of the catheter.

Figure 26A:
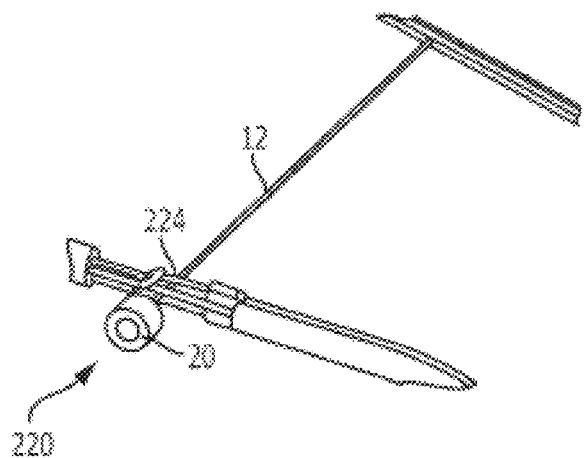
FIG. 26A depicts a step in cutting and removal of a bridge element of an implant with a bridge cutting catheter with suture grip, in accordance with aspects of the invention.
Figure 26B:
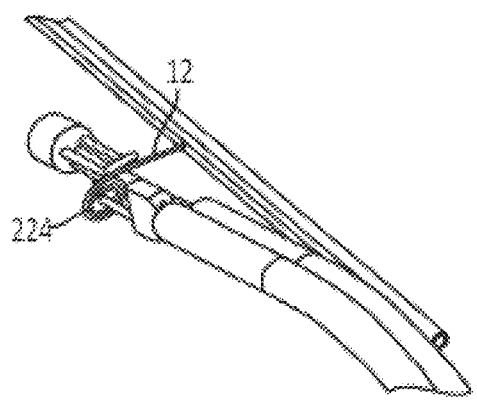
FIG. 26B depicts a step in cutting and removal of a bridge element of an implant with a bridge cutting catheter with suture grip, in accordance with aspects of the invention.

As shown in FIG. 26A, cutting catheter 220 is positioned adjacent the anterior anchor (not shown) and locking bridge stop 30 and positioned to capture tensioned bridging element 12 with capture loop 223 and hold the bridging element with the suture grip 224 (positioned further from the anterior anchor than the cutting blade 222). After initial cutting of the bridging element 12 with the cutting element, as described above, the suture grip 224 is actuated by rotation of a rotatable member extending through the shaft. This winds up excess suture and also moves the cutting catheter adjacent the posterior anchor, as shown in FIG. 26B. As the suture grip 224 holds the excess suture taut, a second cut can be made with cutting tip, similar to that previously described, thereby removing a majority of the bridging element. The excess suture is retained on the suture grip and removed upon removal of the cutting catheter.

System for Anatomical Vessel Insertion Depth

As discussed herein, insertion depth of a catheter of the invention may be determined in a number of different ways. For example, components of the system of the invention may be constructed of materials that are radiopaque or incorporate radiopaque features to facilitate fluoroscopic visualization. However, it will be appreciated that insertion depth may also be determined without the use of fluoroscopic visualization.

Figure 31:
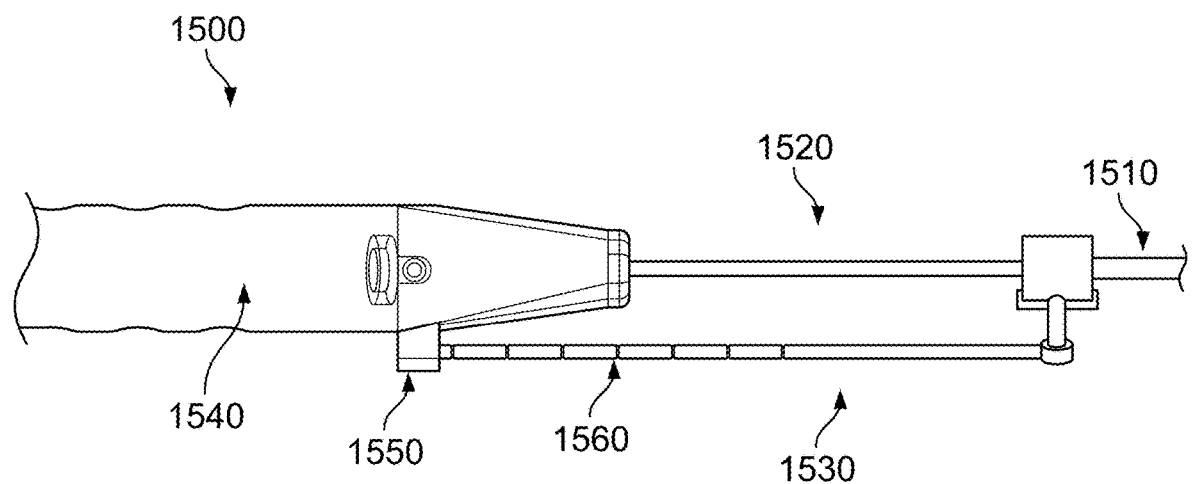
FIG. 31 shows a catheter system in accordance with aspects of the invention. Shown is the proximal end of the catheter system including portions of the overtube and handle of a catheter of the invention.
Figure 32:
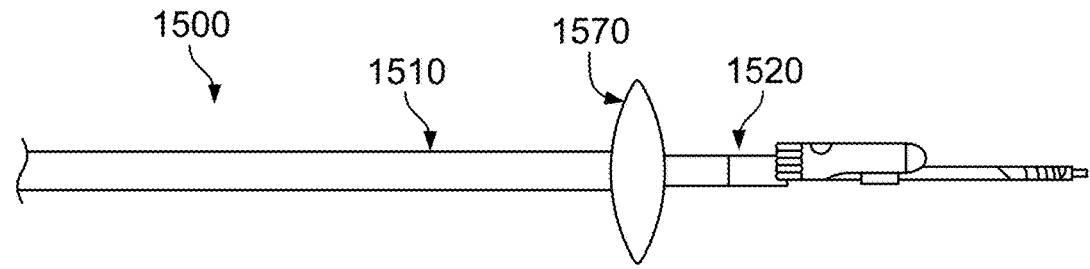
FIG. 32 shows a catheter system in accordance with aspects of the invention. Shown is the distal end of the catheter system depicted in FIG. 31 including portions of the overtube and distal end of a catheter of the invention.

Accordingly, in embodiments, the invention provides a catheter system that allows for measuring insertion depth of a catheter within an anatomical vessel. It will be appreciated that while the present disclosure illustrates use of the system in cardiac procedures, the system may be utilized in any surgical procedure in which determination of insertion depth within an anatomical vessel is desirable. With reference to FIGS. 31 and 32, the catheter system 1500 includes an elongated overtube 1510, a catheter 1520 slidably disposed within the lumen of the overtube, and a depth measurement mechanism 1530. In some aspects, the catheter 1520 includes a handle 1540 along with a coupling 1550 that engages an elongated shaft 1560 of the measurement mechanism 1530. In various aspects, the depth measurement mechanism 1530 is slidably coupled to the handle 1540 via the coupling 1550 disposed at the proximal end of the mechanism 1530 and coupled to the overtube 1510 at a distal end of the mechanism. In some aspects, the mechanism 1530 is configured to measure movement of the catheter 1520 along the lumen of the overtube 1510 when the distal end of the catheter 1520 is advanced distal to the distal end of the overtube 1510 when an expandable member 1570 of the overtube 1510 is inflated within the vessel or at the entrance point from a chamber to a vessel. As such, the elongated shaft 1560 translates movement of the catheter 1520 relative to the overtube 1510 when the catheter is advanced distally or proximally within the lumen of the overtube.

In a related embodiment, the invention provides a method for measuring insertion depth within an anatomical vessel using the catheter system of the invention. The method includes advancing the catheter system of the invention into an anatomical vessel. The inflation member is then expanded so that the overtube remains stationary within the vessel or against the entry to a vessel in an external chamber such as the right atrium. The method further includes advancing the distal end of the catheter distal to the distal end of the overtube and measuring via the measurement mechanism a distance the distal end of the catheter is advanced distal to the distal end of the overtube, thereby measuring insertion depth of the catheter within the anatomical vessel.

Figure 33:
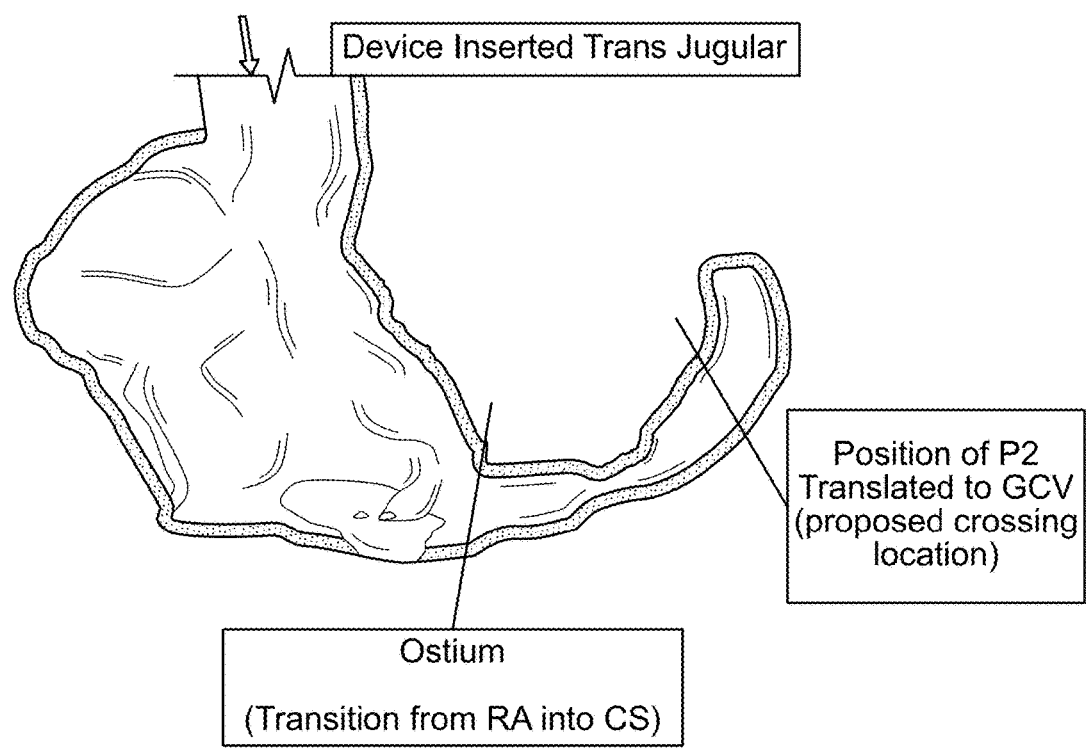
FIG. 33 is an illustration showing different positions of the heart for measuring insertion depth of a catheter of the invention.
Figure 34:
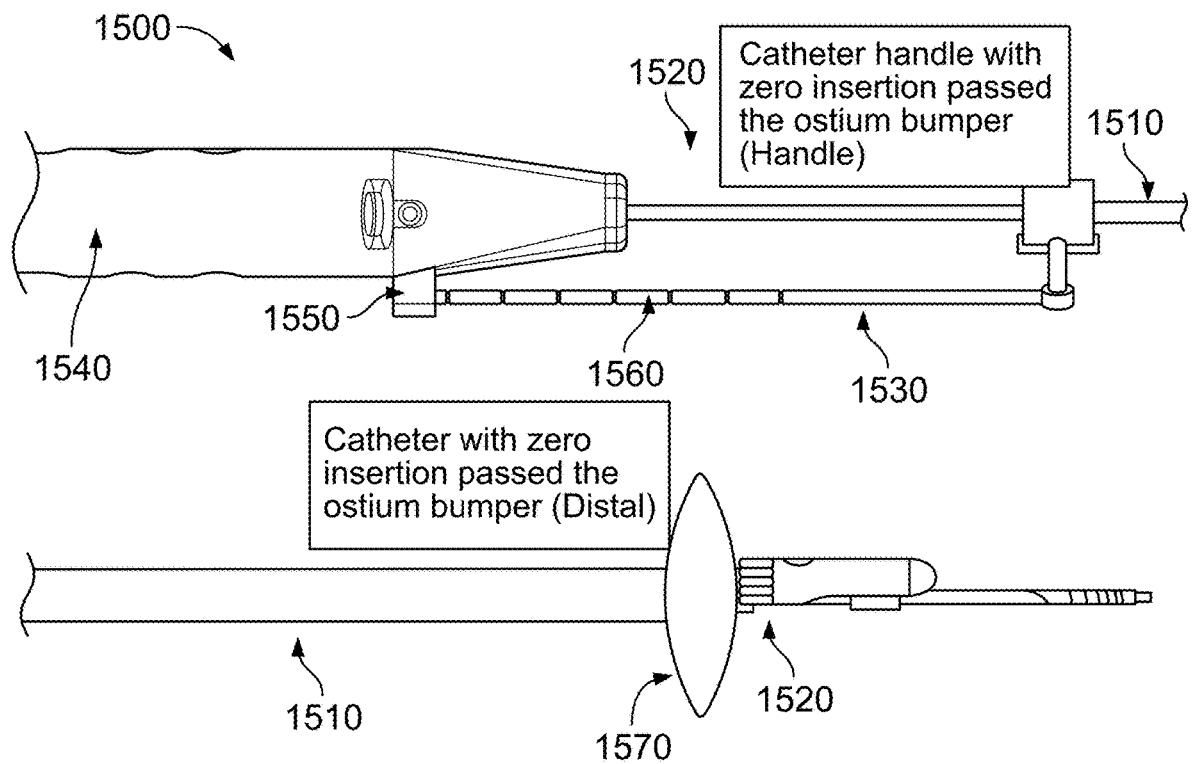
FIG. 34 shows a catheter system of the invention for measuring the depth of insertion in accordance with aspects of the invention. Shown is a catheter system having a measuring mechanism where the inflation member is expanded and the insertion depth is zero.
Figure 35:
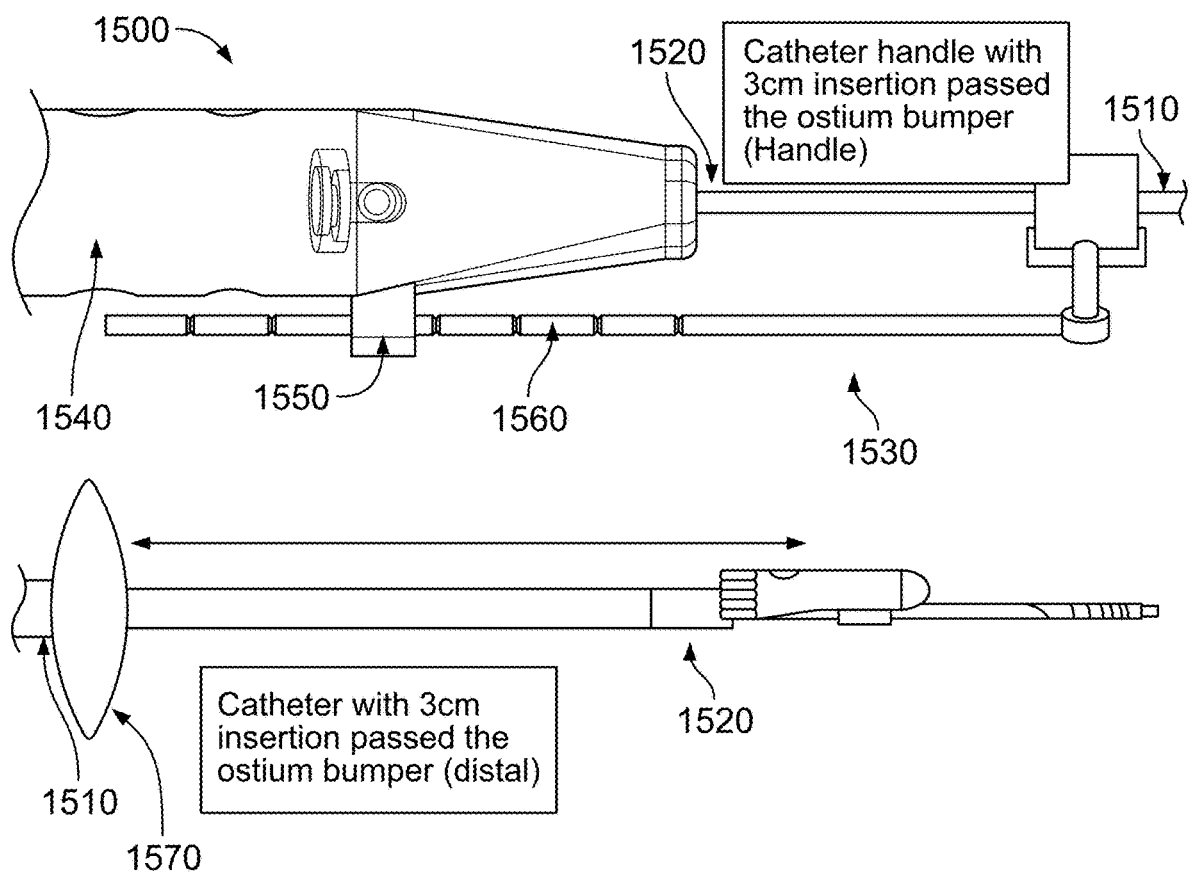
FIG. 35 shows the catheter system depicted in FIG. 34 where the inflation member is expanded and the insertion depth is measured via the measuring mechanism resulting from the distal advancement of the catheter within the overtube.

During operation of the catheter system for use in a procedure to reshape the left atrium the insertion depth of the catheter is determined by a pre-screen of the patient. During the pre-screening of the subject the distance from the ostium to the P2 location (or deeper if determined) of the mitral valve translated to the GCV is determined as shown in FIG. 33 (see distance X). The practicioner then inserts the catheter into the right atrium via the jugular vein. Once in the right atrium the practicioner will perform the fuction of expanding the expandable member 1570. As the practicioner advances the catheter into the GCV the inflation member 1570 contacts the ostium/right atrium wall and the catheter will contiune to advance into the GCV translating out the depth of insertion of the catheter into the GCV. While this is occuring, the measurement mechanism at the handle of the catheter allows the practicioner to ensure that correct positioning of the distal end of the catheter within the GCV has been achieved for the procedure and that puncturing of the wall of the left atrium is at the correct position.

Treatment of Mitral Valve Regurgitation

As discussed herein, the systems and methods described herein are particularly useful for treatment of mitral valve regurgitation by reshaping a chamber of the heart, for example by reshaping the left atrium. As such, the invention provides a method of treating mitral valve regurgitation in a subject by reshaping a heart chamber of the subject utilizing a system as described herein. In one aspect, the method utilizes the first and second catheters shown in FIG. 27. The method includes inserting, through a first vascular access site, the first catheter 1300, and advancing the first catheter 1300 to a first location in or proximate a heart of the subject. The second catheter 1310 is inserted through a second vascular access site and advanced to a second location in or proximate the heart such that the first and second locations are separated by a tissue wall of the heart. The first catheter 1300 and the second catheter 1310 are then positioned such that the first magnet 1320 and the second magnet 1370 magnetically couple across the tissue wall. The tissue wall is then penetrated with a penetrating member, such as a penetrating guidewire advanced through the first catheter 1300, across the tissue wall and through the second catheter 1310 while the first and second catheters are magnetically coupled. A posterior anchor and a bridging element coupled at a first end of the bridging element to the posterior anchor are advanced to the first location from the first vascular access site while the first magnet 1320 and second magnet 1370 are magnetically coupled. A second end of the bridging element is advanced through the penetrated tissue wall and into the second catheter 1310. An anterior anchor is advanced along the bridging element from the second vascular access site and deployed at a third location in the heart with the bridging element spanning across a chamber of the heart as shown in FIGS. 16A-16D. The length of the bridging element is then shortened to reshape the chamber of the heart and the second end of the bridging element coupled to the deployed anterior anchor while the chamber of the heart is reshaped so that the chamber of the heart remains reshaped. In some aspects, the method further includes determining the depth of insertion of the first and/or second catheter via the radiopaque markers disposed along the respective lengths of the catheters (as shown in FIG. 30) before magnetic coupling of the first magnet and the second magnet.

Although the invention has been described with reference to the above examples, it will be understood that modifications and variations are encompassed within the spirit and scope of the invention. Accordingly, the invention is limited only by the following claims.

What is claimed is:

1. A system for delivering a heart implant comprising:
a) a first catheter having a proximal end and a distal end, wherein the first catheter comprises:
 i) a first lumen extending through a length of the first catheter;
 ii) a first magnet disposed along a distal portion of the first catheter, wherein the first magnet includes a first magnetic pole and a second magnetic pole; and
 iii) a first guide channel disposed in the distal portion of the first catheter and extending along a first longitudinal axis, the first guide channel being coextensive with the first lumen and having a first side hole located proximal along the distal portion of the first catheter relative to the first magnetic pole; and
b) a second catheter having a proximal end and a distal end, wherein the second catheter comprises:
 i) a second lumen extending through a length of the second catheter;
 ii) a second magnet disposed at the distal end of the second catheter, wherein the second magnet includes a third magnetic pole and a fourth magnetic pole; and
 iii) a second guide channel disposed at the distal end of the second catheter and extending along a second longitudinal axis, the second guide channel being coextensive with the second lumen and having a second side hole on a side wall of the second catheter and adjacent the second magnet,
wherein the first side hole and the second side hole are aligned in a plane parallel to the first longitudinal axis and the second longitudinal axis, and the second side hole is oriented distal along the distal portion of the first catheter relative to the first side hole, when the first magnet and the second magnet are magnetically coupled.

2. The system of claim 1, wherein the first side hole and second side hole are at an angle of about 90 degrees with respect to one another when the first magnet and second magnet are magnetically coupled.

3. The system of claim 1, wherein the distal portion of the first catheter and the distal end of the second catheter are at an angle of about 90 degrees with respect to one another when the first magnet and second magnet are magnetically coupled.

4. The system of claim 1, wherein the first magnetic pole and the second magnetic pole are disposed perpendicular with respect to the first longitudinal axis.

5. The system of claim 1, wherein the third magnetic pole and the fourth magnetic pole are disposed parallel with respect to the second longitudinal axis with the third magnetic pole being distal to the fourth magnetic pole along the distal end of the second catheter.

6. The system of claim 1, wherein the first magnetic pole and the third magnetic pole are adjacent each other when the first magnet and the second magnet are magnetically coupled.

7. The system of claim 1, wherein the second magnet comprises a contoured recess having an arcuate or sloped surface oriented towards the second guide channel and defining a surface of the second guide channel, the surface of the second guide channel being configured to guide a guidewire extending from the first guide channel through the second guide channel when the first magnet and the second magnet are magnetically coupled.

8. The system of claim 7, wherein the contoured recess extends from a distal portion of the second magnet to a proximal portion of the second magnet.

9. The system of claim 7, further comprising a penetrating member or guidewire advanceable through the first guide channel and the second guide channel via the first side hole and the second side hole when the first magnet and second magnet are magnetically coupled, and wherein the penetrating member or guidewire has a sharpened distal end to facilitate penetration of tissue.

10. The system of claim 1, further comprising a radiopaque marker disposed at the distal end of the first catheter or the distal end of the second catheter.

11. The system of claim 10, wherein the radiopaque marker is disposed at the distal end of the first catheter distal to the first magnet.

12. The system of claim 1, wherein the first catheter comprises radiopaque markers disposed along a length of the first catheter to determine a depth of insertion.

13. The system of claim 1, wherein the second catheter comprises radiopaque markers disposed along a length of the second catheter to determine a depth of insertion.

14. The system of claim 1, wherein the first catheter includes a plurality of radiopaque markers disposed along the distal portion of the first catheter that are arranged asymmetrically about the longitudinal axis of the first guide channel to facilitate alignment of rotational orientation of the first catheter relative to the second catheter before magnetically coupling.

15. The system of claim 14, wherein the the plurality radiopaque markers comprise first and second markers, the first marker being disposed on a same side of the first catheter as the first side hole and being different than the second marker under fluoroscopy.

16. A method of performing a surgical procedure on a subject, the method comprising:

inserting, through a first vascular access site, the first catheter of the system of claim 1, and advancing the first catheter to a first location in or proximate a heart of the subject;

inserting the second catheter of the system of claim 1 through a second vascular access site and advancing the second catheter to a second location in or proximate the heart, the first and second locations being separated by a tissue wall of the heart;

positioning the first catheter and the second catheter such that the first magnet and the second magnet magnetically couple across the tissue wall; wherein the first side hole and the second side hole are aligned in a plane parallel to the first longitudinal axis and the second longitudinal axis, and the second side hole is oriented distal along the distal portion of the first catheter relative to the first side hole; and penetrating the tissue wall with a penetrating member advanced through the first catheter or the second catheter and across the tissue wall while the first and second catheters are magnetically coupled, thereby performing a surgical procedure on the subject.

17. The method of claim 16, further comprising: determining a depth of insertion of the first catheter via radiopaque markers disposed along the length of the first catheter before magnetic coupling of the first magnet and the second magnet.

18. The method of claim 16, further comprising: determining a depth of insertion of the second catheter via radiopaque markers disposed along the length of the second catheter before magnetic coupling of the first magnet and the second magnet.

19. The method of claim 16, further comprising: determining proper alignment of the first catheter and the second catheter via one or more radiopaque markers disposed along the distal portion of the first catheter before the first magnet and the second magnet are magnetically coupled.

20. The method of claim 16, further comprising:

advancing a posterior anchor and a bridging element coupled at a first end of the bridging element to the posterior anchor to the first location from the first vascular access site while the first magnet and the second magnet are magnetically coupled;

advancing a second end of the bridging element through the penetrated tissue wall and into the second catheter; and advancing an anterior anchor along the bridging element from the second vascular access site and deploying the anterior anchor at a third location in the heart, the bridging element spanning across a chamber of the heart.

21. The method of claim 20, wherein the posterior anchor is an elongate member having strain relief portions that flex during advancement to the first location so as to accommodate curvature of the vasculature and avoid crimping of the posterior anchor.

22. The method of claim 20, further comprising shortening a length of the bridging element thereby reshaping the chamber of the heart.

23. The method of claim 22, wherein shortening the length of the bridging element comprises advancing the second end of the bridging element through or across the deployed anterior anchor.

24. The method of claim 22, further comprising: coupling the bridging element to the deployed anterior anchor while the chamber of the heart is reshaped so that the chamber of the heart remains reshaped.

25. The method of claim 24, wherein the bridging element is attached to the posterior anchor at the first end of the bridging element and attached to the anterior anchor at the second end of the bridging element.

26. The method of claim 20, wherein the chamber of the heart is the left atrium.

27. The method of claim 16, wherein the subject has, or is at risk of, mitral valve regurgitation.

28. The method of claim 27, wherein the subject has congestive heart failure.

29. A method of treating mitral valve regurgitation in a subject by reshaping a heart chamber of a subject comprising:

inserting, through a first vascular access site, the first catheter of the system of claim 1, and advancing the first catheter to a first location in or proximate a heart of the subject;

inserting the second catheter of the system of claim 1 through a second vascular access site and advancing the second catheter to a second location in or proximate the heart, the first and second locations being separated by a tissue wall of the heart;

positioning the first catheter and the second catheter such that the first magnet and the second magnet magnetically couple across the tissue wall;

wherein the first side hole and the second side hole are aligned in a plane parallel to the first longitudinal axis and the second longitudinal axis, and the second side hole is oriented distal along the distal portion of the first catheter relative to the first side hole;

penetrating the tissue wall with a penetrating member advanced through the first catheter or the second catheter and across the tissue wall while the first and second catheters are magnetically coupled;

advancing a posterior anchor and a bridging element coupled at a first end of the bridging element to the posterior anchor to the first location while the first magnet and the second magnet are magnetically coupled;

advancing a second end of the bridging element through the penetrated tissue wall when the posterior anchor is advanced through the first catheter; advancing an anterior anchor along the bridging element and deploying the anterior anchor at a third location in the heart, the bridging element spanning across a chamber of the heart;

and shortening a length of the bridging element thereby reshaping the chamber of the heart and coupling the second end of the bridging element to the deployed anterior anchor while the chamber of the heart is reshaped so that the chamber of the heart remains reshaped, thereby treating mitral valve regurgitation in the subject.

30. The method of claim 29, wherein shortening the length of the bridging element comprises advancing the second end of the bridging element through or across the deployed anterior anchor.

31. The method of claim 29, further comprising: determining a depth of insertion of the first catheter via radiopaque markers disposed along the length of the first catheter before magnetic coupling of the first magnet and the second magnet.

32. The method of claim 29, further comprising: determining a depth of insertion of the second catheter via radiopaque markers disposed along the length of the second catheter before magnetic coupling of the first magnet and the second magnet.

33. The method of claim 29, further comprising: determining proper alignment of the first catheter and the second catheter via one or more radiopaque markers disposed along the distal portion of the first catheter before the first magnet and the second magnet are magnetically coupled.

34. The method of claim 29, wherein the chamber of the heart is the left atrium.

\* \* \* \* \*